United States Patent
Galan et al.

(10) Patent No.: US 11,440,918 B2
(45) Date of Patent: Sep. 13, 2022

(54) P38α MITOGEN-ACTIVATED PROTEIN KINASE INHIBITORS

(71) Applicant: GEN1E LIFESCIENCES INC., Palo Alto, CA (US)

(72) Inventors: Adam Galan, Alameda, CA (US); Wendy Luo, Sunnyvale, CA (US); Ritu Lal, Palo Alto, CA (US)

(73) Assignee: GEN1E LIFESCIENCES INC., Palo Alto, CA (US)

( * ) Notice: Subject to any disclaimer, the term of this patent is extended or adjusted under 35 U.S.C. 154(b) by 0 days.

(21) Appl. No.: 17/667,898

(22) Filed: Feb. 9, 2022

(65) Prior Publication Data

US 2022/0162224 A1    May 26, 2022

Related U.S. Application Data

(63) Continuation of application No. 17/320,874, filed on May 14, 2021, now Pat. No. 11,286,260.

(60) Provisional application No. 63/026,466, filed on May 18, 2020.

(51) Int. Cl.
| | | |
|---|---|---|
| C07D 491/107 | (2006.01) | |
| A61P 31/14 | (2006.01) | |
| C07D 207/12 | (2006.01) | |
| C07D 211/42 | (2006.01) | |
| C07D 211/46 | (2006.01) | |
| C07D 239/30 | (2006.01) | |
| C07D 241/08 | (2006.01) | |
| C07D 265/30 | (2006.01) | |
| C07D 267/10 | (2006.01) | |
| C07D 491/048 | (2006.01) | |
| C07D 498/18 | (2006.01) | |

(52) U.S. Cl.
CPC .......... *C07D 491/107* (2013.01); *A61P 31/14* (2018.01); *C07D 207/12* (2013.01); *C07D 211/42* (2013.01); *C07D 211/46* (2013.01); *C07D 239/30* (2013.01); *C07D 241/08* (2013.01); *C07D 265/30* (2013.01); *C07D 267/10* (2013.01); *C07D 491/048* (2013.01); *C07D 498/18* (2013.01)

(58) Field of Classification Search
CPC ............. C07D 491/107; C07D 207/12; C07D 211/42; C07D 211/46; C07D 239/30; C07D 241/08; C07D 265/30; C07D 267/10; C07D 491/048; C07D 498/18
See application file for complete search history.

(56) References Cited

U.S. PATENT DOCUMENTS

| | | | |
|---|---|---|---|
| 3,594,386 A | 7/1971 | Regnier et al. | |
| 6,462,074 B1 | 10/2002 | Stolle et al. | |
| 8,173,684 B2 | 5/2012 | Kasahara et al. | |
| 11,286,260 B2* | 3/2022 | Galan | A61P 31/12 |
| 2005/0256133 A1* | 11/2005 | Lesur | A61P 25/26 564/162 |
| 2007/0066616 A1 | 3/2007 | Shapiro et al. | |
| 2007/0208015 A1 | 9/2007 | Gill et al. | |
| 2010/0215618 A1 | 8/2010 | Carter et al. | |
| 2015/0357549 A1 | 12/2015 | Muller et al. | |
| 2019/0151324 A1 | 5/2019 | Shapiro et al. | |

FOREIGN PATENT DOCUMENTS

| | | |
|---|---|---|
| CN | 101675034 | 3/2010 |
| CN | 105308004 | 2/2016 |
| CN | 109640970 A | 4/2019 |
| DE | 19801646 A1 | 7/1999 |
| EP | 3474835 A1 | 5/2019 |
| WO | 2004/065351 A1 | 8/2004 |
| WO | 2004/072077 A1 | 8/2004 |
| WO | 2005/100338 A1 | 10/2005 |
| WO | 2009/106844 A1 | 9/2009 |
| WO | 2010/082912 | 7/2010 |
| WO | 2010/094977 | 8/2010 |
| WO | 2015/121660 A1 | 8/2015 |
| WO | 2016/051155 | 4/2016 |
| WO | 2016/073633 | 5/2016 |
| WO | 2017/223284 A1 | 12/2017 |
| WO | 2020/118194 | 6/2020 |
| WO | 2021/183970 A2 | 9/2021 |

OTHER PUBLICATIONS

Cheng; Journal of Medicinal Chemistry 2014, 57, 2692-2703. (Year: 2014).*
Wang; Methods in Enzymology 2014, 548, 23-67. (Year: 2014).*
Chemical Abstracts STN Registry Database, Record for RN 1587574-74-0, "N-[4-[(4-Chlorobenzoyl)amino]phenyl]-2-oxo-1-piperazineacetamide hydrochloride", Entered STN Apr. 21, 2014. (Year: 2014).*
Chemical Abstracts STN Registry Database, Record for RN 851167-79-8, Entered STN May 26, 2005. (Year: 2005).*
Chemical Abstracts STN Registry Database, Record for RN 2331174-12-8, Entered STN Jun. 12, 2019. (Year: 2019).*
Chemical Abstracts STN Registry Database, Record for RN 2338713-47-4, Entered STN Jun. 18, 2019. (Year: 2019).*
Chemical Abstracts STN Registry Database, Record for RN 2347052-15-5, Entered STN Jun. 27, 2019. (Year: 2019).*
International Search Report and Written Opinion for Application No. PCT/US2019/064960, dated Feb. 25, 2020, 7 pages.
International Search Report and Written Opinion for Application No. PCT/US2017/038697, dated Oct. 31, 2017, 12 pages.
International Search Report and Written Opinion for Application No. PCT/US2021/032487, dated Sep. 22, 2021, 19 pages.

(Continued)

*Primary Examiner* — Daniel R Carcanague

(57) ABSTRACT

Disclosed herein are p38α mitogen-activated protein kinase inhibitors, pharmaceutical compositions thereof, and therapeutic methods of using the p38α mitogen-activated protein kinase inhibitors.

29 Claims, No Drawings

Specification includes a Sequence Listing.

(56) References Cited

OTHER PUBLICATIONS

Extended European Search Report for Application No. EP 17816192, dated Mar. 30, 2020, 5 pages.
Non-Final Office Action for U.S. Appl. No. 16/312,499, dated Feb. 13, 2020, 8 pages.
Final Office Action for U.S. Appl. No. 16/312,499, dated May 21, 2020, 11 pages.
Non-Final Office Action for U.S. Appl. No. 17/231,598, dated Jun. 29, 2021, 9 pages.
Non-Final Office Action for U.S. Appl. No. 16/872,114, dated Dec. 7, 2020, 7 pages.
Biava et al., "Synthesis and Antimycobacterial Activity of New Amidoderivatives of Ortho-, Meta- and Para-Toluidine", Medicinal Chemistry Research, Jan. 1998, vol. 8, No. 9, pp. 523-541.
Biava et al., "Antimycobacterial activity of new ortho-, meta- and para-toluidine derivatives", Il Farmaco, 1999, vol. 54, pp. 721-727.
Chemical Abstract STN Registry Database record for RN 2337349-33-2, entered into STN Jun. 17, 2019.
Chemical Abstract STN Registry Database Record for RN 1293859-67-2, STN Entered May 12, 2011.
CAS 2337349-33-2 retrieved on Jun. 17, 2019.
CAS 255713-96-3 retrieved on Feb. 10, 2000.
CAS 697229-25-7 retrieved on Jun. 22, 2004.
Haller et al., "An updated patent review of p38 MAP kinase inhibitors (2014-2019)", Expert Opinion on Therapeutics Patents, 2020, vol. 30, No. 6, p. 453-466.
Koroleva et al., "Synthesis of new amides of the N-methylpiperazine series", Russian Journal of Organic Chemistry, Nauka/Interperiodica, Nov. 2011, vol. 47, No. 10, pp. 1556-1563.
Lee et al., "Docketing-based 3D-QSAR study for 11β-HSD1 inhibitors", Bioorganic & Medicinal Chemistry Letters, 2008, vol. 18, pp. 2479-2490.
Pubchem CID 899207 created Jul. 9, 2005, accessed on Feb. 5, 2020, 9 pages.
Pubchem, Substance Database SID 105140242, available on Feb. 22, 2011, retrieved on Aug. 8, 2017, retrieved from https://pubchem.ncbi.nlm.nih.gov/substance/105140242.
Sasindran et al., "*Mycobacterium tuberculosis* Infection and Inflammation: what is Beneficial for the Host and for the Bacterium?", Frontiers in Microbiology, Jan. 2011, vol. 2, Article 2, 33 pages.
Shah et al., "Novel Noncatalytic Substrate-Selective p38[alpha]-Specific MAPK Inhibitors with Endothelial-Stabilizing and Anti-Inflammatory Activity", The Journal of Immunology, Mar. 2017, vol. 198, No. 8, pp. 3296-3306.
Yong et al., "The p38 MAPK inhibitors for the treatment of inflammatory diseases and cancer", Expert Opinion on Investigational Drugs, Oct. 2009, ISSN 1354-3784, vol. 18, No. 12, pp. 1893-1905.
International Search Report and Written Opinion for Application No. PCT/US2021/055950, dated Dec. 14, 2021, 14 pages.
Caira, Mino R. "Crystalline Polymorphism of Organic Compounds", Topics in Current Chemistry, Jan. 1998, vol. 198, pp. 163-208.
Kheiri et al., "Role pf p38/MAPKs in Alzheimer's disease: implications for amyloid beta toxicity targeted therapy", Reviews in Neuroscience, 2018, vol. 30, No. 1, pp. 9-30.
Mavropoulos et al., "p38 mitogen-activated protein kinase (p38 MAPK)-mediated autoimmunity: Lessons to learn from ANCA vasculitis and pemphigus vulgaris", Autoimmunity Reviews, Mar. 2013, vol. 12, Issue 5, pp. 580-590.
Nagao et al., "Synthesis and structure-activity relationships of novel, potent, orally active hypoxia-inducible factor-1 inhibitors", Bioorganic & Medicinal Chemistry, Jul. 2014, vol. 22, No. 19, pp. 5513-5529.
Segales et al., "Regulation of Muscle Stem Cell Functions: A Focus on the p38 MAPK Signaling Pathway", Frontiers in Cell and Developmental Biology, Aug. 2016, vol. 4, Article 91, 15 pages.

\* cited by examiner

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
taatcagaca aggaactgat ta                                              22

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgaaggtgtg acttccatg                                                  19
```

P38α MITOGEN-ACTIVATED PROTEIN KINASE INHIBITORS

This application is a continuation of U.S. application Ser. No. 17/320,874, filed on May 14, 2021, now allowed, which claims the benefit under 35 U.S.C. § 119(e) of U.S. Provisional Application No. 63/026,466 filed on May 18, 2020, which is incorporated by reference in its entirety.

SEQUENCE LISTING

The instant application contains a Sequence Listing which has been submitted electronically in ASCII format and is hereby incorporated by reference in its entirety. Said ASCII copy, created on May 27, 2021, is named 67LZ-000410US-332037_SL.txt and is 747 bytes in size.

FIELD

The present disclosure relates to p38α mitogen-activated protein kinase inhibitors, pharmaceutical compositions thereof, and the use of the p38α mitogen-activated protein kinase inhibitors and pharmaceutical compositions thereof for threating a disease.

BACKGROUND

MAPKs are serine/threonine protein kinases that process and regulate cellular properties in response to a wide range of extracellular stimuli. p38 MAPK comprises four isoforms (α, β, γ and δ). p38α MAPK was the first isoform of p38 MAPK to be identified and was first recognized as a stress-induced kinase that can be activated by lipopolysaccharide (LPS) and inflammatory cytokines. These enzymes phosphorylate the OH group of serine or threonine in proteins and play important roles in the regulation of cell proliferation, differentiation, survival and apoptosis. In mammalian cells, several distinct MAPKs have been identified, including p38 MAPK.

p38 MAPK is a class of MAPKs responsive to stress stimuli such as inflammatory cytokines and reactive oxygen species (ROS) and is involved in a wide range of signaling pathways that stimulate different biological functions. For example, p38 MAPK has been found to play an essential role in the regulation of pro-inflammatory signaling networks and in the biosynthesis of cytokines, including tumor necrosis factor-α (TNF-α) and interleukin-1β (IL-1β) in immune cells Studies have shown that p38 MAPKs contribute to the pathogenesis of chronic inflammation, thereby motivating preclinical and clinical trials for the application of p38 MAPK inhibitors in inflammatory diseases such as rheumatoid arthritis and asthma.

Many p38 MAPK catalytic inhibitors are poorly effective and cause toxicity possibly due to activity against non-inflammatory p38 and loss of p38α-dependent counterregulatory responses. p38α MAPK inhibitors that can selectively inhibit certain p38α MAPK functions and preserve critical counterregulatory and homeostatic functions with application for the treatment of inflammatory and oncologic diseases are desired. Inhibition of p38 MAPKs has been shown to effectively alleviate inflammatory diseases such as rheumatoid arthritis, cardiovascular disease and inflammatory pain.

SUMMARY

According to the present invention, compounds have the structure of Formula (1):

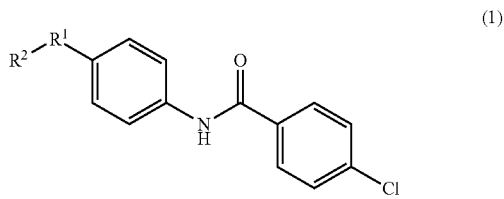

or a pharmaceutically acceptable salt thereof, wherein,
$R^1$ is selected from $C_{1-4}$ alkanediyl, $C_{1-4}$ heteroalkanediyl, substituted $C_{1-4}$ alkanediyl, and substituted $C_{1-4}$ heteroalkanediyl; and
$R^2$ is selected from a moiety of Formula (2a), a moiety of Formula (2b), a moiety of Formula (2c), $C_{8-16}$ heterobicycloalkyl, and substituted $C_{8-16}$ heterobicycloalkyl:

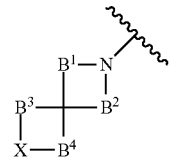

(2a)

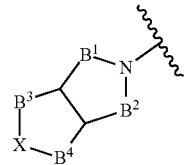

(2b)

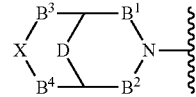

(2c)

wherein,
each of $B^1$, $B^2$, $B^3$, and $B^4$ is independently selected from $-(CH(-R^4))_n-$, wherein,
each n is independently selected from, 0, 1, 2, 3, and 4;
both $B^1$ and $B^2$ are not 0;
both $B^3$ and $B^4$ are not 0; and
each $R^4$ is independently selected from hydrogen, $-OH$, $-NH_2$, $-NO_2$, $C_{1-3}$ alkyl, $C_{1-3}$ heteroalkyl, substituted $C_{1-3}$ alkyl, and substituted $C_{1-3}$ heteroalkyl;
D is selected from methane-diyl and ethane-diyl; and
X is selected from $-O-$, $-CH(-OH)-$, $-NR^3-$, and $-SO_2-$, wherein $R^3$ is selected from hydrogen, $C_{1-6}$ alkyl, $C_{1-6}$ cycloalkyl, $C_6$ aryl, $C_{1-6}$ heteroalkyl, $C_{1-6}$ heterocycloalkyl, $C_{5-6}$ heteroaryl, substituted $C_{1-6}$ alkyl, substituted $C_{1-6}$ cycloalkyl, substituted $C_6$ aryl, substituted $C_{1-6}$ heteroalkyl, substituted $C_{1-6}$ heterocycloalkyl, and substituted $C_{5-6}$ heteroaryl.

According to the present invention, compounds have the structure of Formula (1):

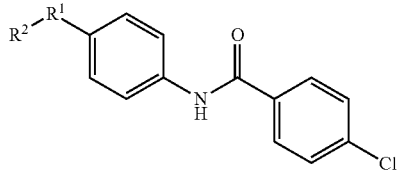

(1)

or a pharmaceutically acceptable salt thereof, wherein,
$R^1$ is selected from $C_{1-4}$ alkanediyl, $C_{1-4}$ heteroalkanediyl, substituted $C_{1-4}$ alkanediyl, and substituted $C_{1-4}$ heteroalkanediyl; and
$R^2$ is a moiety of Formula (2d):

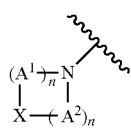

(2d)

wherein,
each $A^1$ and $A^2$ is independently selected from —$CH_2$—, —$CH(-R^5)$—, and —$C(=O)$—, wherein, each $R^5$ is independently selected from —OH, —$NH_2$, —$NO_2$, $C_{1-6}$ alkyl, $C_{1-6}$ cycloalkyl, $C_6$ aryl, $C_{1-6}$ heteroalkyl, $C_{1-6}$ heterocycloalkyl, $C_{5-6}$ heteroaryl, substituted $C_{1-6}$ alkyl, substituted $C_{1-6}$ cycloalkyl, substituted $C_6$ aryl, substituted $C_{1-6}$ heteroalkyl, substituted $C_{1-6}$ heterocycloalkyl, and substituted $C_{5-6}$ heteroaryl;
one or more of $A^1$ and $A^2$ is independently selected from —$CH(-R^5)$— and —$C(=O)$—;
each n is independently selected from, 1, 2, 3, and 4; and
X is selected from —O—, —CH(—OH)—, —$NR^3$—, and —$SO_2$—, wherein $R^3$ is selected from hydrogen, $C_{1-6}$ alkyl, $C_{5-8}$ cycloalkyl, $C_6$ aryl, $C_{6-12}$ cycloalkylalkyl, $C_{7-10}$ arylalkyl, $C_{1-6}$ heteroalkyl, $C_{5-8}$ heterocycloalkyl, $C_{5-6}$ heteroaryl, $C_{6-12}$ heterocycloalkylalkyl, $C_{7-10}$ heteroarylalkyl, substituted $C_{1-6}$ alkyl, substituted $C_{5-8}$ cycloalkyl, substituted $C_6$ aryl, substituted $C_{6-12}$ cycloalkylalkyl, substituted $C_{7-10}$ arylalkyl, substituted $C_{1-6}$ heteroalkyl, substituted $C_{5-8}$ heterocycloalkyl, substituted $C_{5-6}$ heteroaryl, substituted $C_{6-12}$ heterocycloalkylalkyl, and substituted $C_{7-10}$ heteroarylalkyl.

According to the present invention, pharmaceutical compositions comprise a compound according to the present invention or a pharmaceutically acceptable salt thereof.

According to the present invention, methods of treating a disease in a patient comprise administering to a patient in need thereof a therapeutically effective amount of the compound of a compound according to the present invention or a pharmaceutically acceptable salt thereof, wherein the disease is cancer such as melanoma; an inflammatory disease such as acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes, rheumatoid arthritis, amyotrophic lateral sclerosis, cystic fibrosis; an autoimmune disease; an age-related disease such as hearing loss, muscle degeneration, Werner's syndrome, cellular aging, and Alzheimer's disease, or a viral disease such as a coronavirus infection, pneumonia associated with a coronavirus infection, and a Human Respiratory Syndical infection.

DETAILED DESCRIPTION

A dash ("-") that is not between two letters or symbols is used to indicate a point of attachment for a moiety or substituent. For example, —$CONH_2$ is attached through the carbon atom.

"Alkyl" refers to a saturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like. The term "alkyl" includes groups having any degree or level of saturation, i.e., groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. An alkyl group can be $C_{1-6}$ alkyl, $C_{1-5}$ alkyl, $C_{1-4}$ alkyl, $C_{1-3}$ alkyl, ethyl or methyl.

"Alkoxy" refers to a radical —OR where R is alkyl as defined herein. Examples of alkoxy groups include methoxy, ethoxy, propoxy, and butoxy. An alkoxy group can be $C_{1-6}$ alkoxy, $C_{1-5}$ alkoxy, $C_{1-4}$ alkoxy, $C_{1-3}$ alkoxy, ethoxy, or methoxy.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms selected from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, and triphenylene, trinaphthalene. An aryl group can be $C_{6-10}$ aryl, $C_{6-9}$ aryl, $C_{6-8}$ aryl, or phenyl. Aryl, however, does not encompass or overlap in any way with heteroaryl, separately defined herein.

"Arylalkyl" refers to an acyclic alkyl radical in which one of the hydrogen atoms bonded to a carbon atom is replaced with an aryl group. Examples of arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. An arylalkyl group can be $C_{7-16}$ arylalkyl, e.g., the alkanyl, alkenyl or alkynyl moiety of the arylalkyl group is $C_{1-6}$ and the aryl moiety is $C_{6-10}$. An arylalkyl group can be $C_{7-16}$ arylalkyl, e.g., the alkanyl, alkenyl or alkynyl moiety of the arylalkyl group is $C_{1-6}$ and the aryl moiety is $C_{6-10}$. An arylalkyl group can be $C_{7-9}$ arylalkyl, wherein the alkyl moiety is $C_{1-3}$ alkyl and the aryl moiety is phenyl. An arylalkyl group can be $C_{7-16}$ arylalkyl, $C_{7-14}$ arylalkyl, $C_{7-12}$ arylalkyl, $C_{7-10}$ arylalkyl, $C_{7-8}$ arylalkyl, or benzyl.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"Oral bioavailability" (F %) refers to the fraction of an orally administered drug that reaches the systemic circulation. Oral bioavailability is a product of fraction absorbed, fraction escaping gut-wall elimination, and fraction escaping hepatic elimination; and the factors that influence bioavailability can be divided into physiological, physicochemical, and biopharmaceutical factors.

"Compounds" disclosed herein include any specific compounds within the disclosed formula. Compounds may be identified either by chemical structure and/or by chemical name. Compounds are named using the ChemBioDraw Ultra 14.0.0.117 (CambridgeSoft, Cambridge, Mass.) nomenclature program. When the chemical structure and chemical name conflict, the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled in the art.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example, a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

"Cycloalkyl" refers to a saturated or partially unsaturated cyclic alkyl radical. A cycloalkyl group can be $C_{3-8}$ cycloalkyl, $C_{3-5}$ cycloalkyl, $C_{5-6}$ cycloalkyl, cyclopropyl, cyclopentyl, or cyclohexyl. A cycloalkyl can be selected from cyclopropyl, cyclobutyl, cyclopentyl, cyclohexyl, cycloseptyl, and cyclooctyl.

"Cycloalkylalkyl" refers to an acyclic alkyl radical in which one of the hydrogen atoms bonded to a carbon atom is replaced with a cycloalkyl group as defined herein. Where specific alkyl moieties are intended, the nomenclature cycloalkylalkyl, cycloalkylalkenyl, or cycloalkylalkynyl is used. A cycloalkylalkyl group can be $C_{4-30}$ cycloalkylalkyl, e.g., the alkanyl, alkenyl, or alkynyl moiety of the cycloalkylalkyl group is $C_{1-10}$ and the cycloalkyl moiety of the cycloalkylalkyl moiety is $C_{3-20}$. A cycloalkylalkyl group can be $C_{4-20}$ cycloalkylalkyl, e.g., the alkanyl, alkenyl, or alkynyl moiety of the cycloalkylalkyl group is $C_{1-8}$ and the cycloalkyl moiety of the cycloalkylalkyl group is $C_{3-12}$. A cycloalkylalkyl can be $C_{4-9}$ cycloalkylalkyl, wherein the alkyl moiety of the cycloalkylalkyl group is $C_{1-3}$ alkyl, and the cycloalkyl moiety of the cycloalkylalkyl group is $C_{3-6}$ cycloalkyl. A cycloalkylalkyl group can be $C_{4-12}$ cycloalkylalkyl, $C_{4-10}$ cycloalkylalkyl, $C_{4-8}$ cycloalkylalkyl, and $C_{4-6}$ cycloalkylalkyl. A cycloalkylalkyl group can be cyclopropylmethyl (—CH$_2$-cyclo-C$_3$H$_5$), cyclopentylmethyl (—CH$_2$-cyclo-C$_5$H$_9$), or cyclohexylmethyl (—CH$_2$-cyclo-C$_6$H$_{11}$). A cycloalkylalkyl group can be cyclopropylethenyl (—CH═CH-cyclo-C$_3$H$_5$), cyclopentylethynyl (—C≡C-cyclo-C$_5$H$_9$), or the like.

"Cycloalkylheteroalkyl" by itself or as part of another substituent refers to a heteroalkyl group in which one or more of the carbon atoms (and certain associated hydrogen atoms) of an alkyl group are independently replaced with the same or different heteroatomic group or groups and in which one of the hydrogen atoms bonded to a carbon atom is replaced with a cycloalkyl group. Where specific alkyl moieties are intended, the nomenclature cycloalkylheteroalkanyl, cycloalkylheteroalkenyl, and cycloalkylheteroalkynyl is used. In a cycloalkylheteroalkyl, the heteroatomic group can be selected from —O—, —S—, —NH—, —N(—CH$_3$)—, —SO—, —SO$_2$—, —Si—, —B—, or the heteroatomic group can be selected from —O— and —NH—, or the heteroatomic group is —O— or —NH—.

"Cycloalkyloxy" refers to a radical —OR where R is cycloalkyl as defined herein. Examples of cycloalkyloxy groups include cyclopropyloxy, cyclobutyloxy, cyclopentyloxy, and cyclohexyloxy. A cycloalkyloxy group can be $C_{3-6}$ cycloalkyloxy, $C_{3-5}$ cycloalkyloxy, $C_{5-6}$ cycloalkyloxy, cyclopropyloxy, cyclobutyloxy, cyclopentyloxy, or cyclohexyloxy.

"Disease" refers to a disease, disorder, condition, or symptom of any of the foregoing.

"Drug" as defined under 21 U.S.C. § 321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ".

"Fluoroalkyl" refers to an alkyl group as defined herein in which one or more of the hydrogen atoms is replaced with a fluoro. A fluoroalkyl group can be $C_{1-6}$ fluoroalkyl, $C_{1-5}$ fluoroalkyl, $C_{1-4}$ fluoroalkyl, or $C_{1-3}$ fluoroalkyl. A fluoroalkyl group can be pentafluoroethyl (—$CF_2CF_3$), or trifluoromethyl (—$CF_3$).

"Fluoroalkoxy" refers to an alkoxy group as defined herein in which one or more of the hydrogen atoms is replaced with a fluoro. A fluoroalkoxy group can be $C_{1-6}$ fluoroalkoxy, $C_{1-5}$ fluoroalkoxy, $C_{1-4}$ fluoroalkoxy $C_{1-3}$, fluoroalkoxy, —$OCF_2CF_3$ or —$OCF_3$.

"Halogen" refers to a fluoro, chloro, bromo, or iodo group.

"Heteroalkoxy" refers to an alkoxy group in which one or more of the carbon atoms are replaced with a heteroatom. A heteroalkoxy group can be $C_{1-6}$ heteroalkoxy, $C_{1-5}$ heteroalkoxy, $C_{1-4}$ heteroalkoxy, or $C_{1-3}$ heteroalkoxy. In a heteroalkoxy, the heteroatomic group can be selected from —O—, —S—, —NH—, —NR— where R is $C_{1-6}$ alkyl, —SO—, —$SO_2$—, —Si—, and —B—, or the heteroatomic group can be selected from —O— and —NH—, or the heteroatomic group is —O— and —NH—. A heteroalkoxy group can be $C_{1-6}$ heteroalkoxy, $C_{1-5}$ heteroalkoxy, $C_{1-4}$ heteroalkoxy, or $C_{1-3}$ heteroalkoxy.

"Heteroalkyl" by itself or as part of another substituent refer to an alkyl group in which one or more of the carbon atoms (and certain associated hydrogen atoms) are independently replaced with the same or different heteroatomic group or groups. Examples of heteroatomic groups include —O—, —S—, —Si—, —B—, —NH—, —NR—, —O—O—, —S—S—, =N—N=, —N=N—, —N=N—NR—, —PR—, —P(O)OR—, —P(O)R—, —POR—, —SO—, —$SO_2$—, and —$Sn(R)_2$—, where each R is independently selected from hydrogen, $C_{1-6}$ alkyl, substituted $C_{1-6}$ alkyl, $C_{6-12}$ aryl, substituted $C_{6-12}$ aryl, $C_{7-18}$ arylalkyl, substituted $C_{7-18}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-18}$ heteroarylalkyl, and substituted $C_{7-18}$ heteroarylalkyl. Each R can be independently selected from hydrogen and $C_{1-3}$ alkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example, $C_{1-6}$ heteroalkyl includes groups having five carbon atoms and one heteroatom, groups having four carbon atoms and two heteroatoms, etc. In a heteroalkyl, the heteroatomic group can be selected from —O—, —S—, —NH—, —N(—$CH_3$)—, —SO—, —$SO_2$—, —Si—, and —B—, or the heteroatomic group can be selected from —O— and —NH—, or the heteroatomic group can be —O— or —NH—. A heteroalkyl group can be $C_{1-6}$ heteroalkyl, $C_{1-5}$ heteroalkyl, or $C_{1-4}$ heteroalkyl, or $C_{1-3}$ heteroalkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. When the total number of N, S, and O atoms in the heteroaryl group exceeds one, the heteroatoms may or may not be adjacent to one another. The total number of heteroatoms in the heteroaryl group is not more than two. In a heteroaryl, the heteroatomic group can be selected from —O—, —S—, —NH—, —N(—$CH_3$)—, —SO—, —$SO_2$—, —Si—, and —B—, or the heteroatomic group can be selected from —O— and —NH—, or the heteroatomic group can be —O— or —NH—. A heteroaryl group can be selected from, for example, $C_{5-10}$ heteroaryl, $C_{5-9}$ heteroaryl, $C_{5-8}$ heteroaryl, $C_{5-7}$ heteroaryl, $C_{5-6}$ heteroaryl, $C_5$ heteroaryl or $C_6$ heteroaryl.

Examples of heteroaryl groups include groups derived from acridine, arsindole, carbazole, α-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, and oxazolidine. A heteroaryl groups can be derived, for example, from thiophene, pyrrole, benzothiophene, benzofuran, indole, pyridine, quinoline, imidazole, oxazole, or pyrazine. For example, a heteroaryl can be $C_5$ heteroaryl and can be selected from furyl, thienyl, pyrrolyl, imidazolyl, pyrazolyl, isothiazolyl, or isoxazolyl. A heteroaryl can be $C_6$ heteroaryl, and can be selected from pyridinyl, pyrazinyl, pyrimidinyl, and pyridazinyl.

"Heteroarylalkyl" refers to an arylalkyl group in which one of the carbon atoms (and certain associated hydrogen atoms) is replaced with a heteroatom. A heteroarylalkyl group can be $C_{6-16}$ heteroarylalkyl, $C_{6-14}$ heteroarylalkyl, $C_{6-12}$ heteroarylalkyl, $C_{6-10}$ heteroarylalkyl, $C_{6-8}$ heteroarylalkyl, or $C_7$ heteroarylalkyl, or $C_6$ heteroarylalkyl. In a heteroarylalkyl, the heteroatomic group can be selected from —O—, —S—, —NH—, —N(—$CH_3$)—, —SO—, —$SO_2$—, —Si—, and —B—, or the heteroatomic group can be selected from —O— and —NH—, or the heteroatomic group can be —O— or —NH—.

"Heterobicycloalkyl" refers to a moiety having two heterocycloalkyl groups. A heterobicyccloalkyl group can be a fused ring or spiro compound.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system violates the Hückel-rule. Examples of heteroatoms to replace the carbon atom(s) include N, P, O, S, B, and Si. Examples of heterocycloalkyl groups include groups derived from epoxides, azetidines, azirines, thiiranes, imidazolidine, morpholine, piperazine, piperidine, pyrazolidine, pyrrolidine, and quinuclidine. A heterocycloalkyl can be $C_5$ heterocycloalkyl and is selected from pyrrolidinyl, tetrahydrofuranyl, tetrahydrothiophenyl, imidazolidinyl, oxazolidinyl, thiazolidinyl, doxolanyl, and dithiolanyl. A heterocycloalkyl can be $C_6$ heterocycloalkyl and can be selected from piperidinyl, tetrahydropyranyl, piperizinyl, oxazinyl, dithianyl, and dioxanyl. A heterocycloalkyl group can be $C_{3-8}$ heterocycloalkyl, $C_{3-8}$ heterocycloalkyl, $C_{3-5}$ heterocycloalkyl, $C_{5-6}$ heterocycloalkyl, $C_5$ heterocycloalkyl or $C_6$ heterocycloalkyl. In a heterocycloalkyl, the heteroatomic group can be selected from —O—, —S—, —NH—, —N(—CH$_3$)—, —SO—, —SO$_2$—, —Si—, —B—, or the heteroatomic group can be selected from —O— and —NH—, or the heteroatomic group can be —O— or —NH—.

"Heterocycloalkylalkyl" refers to a cycloalkylalkyl group in which one or more carbon atoms (and certain associated hydrogen atoms) of the cycloalkyl ring are independently replaced with the same or different heteroatom. A heterocycloalkylalkyl can be $C_{4-12}$ heterocycloalkylalkyl, $C_{4-10}$ heterocycloalkylalkyl, $C_{4-8}$ heterocycloalkylalkyl, $C_{4-6}$ heterocycloalkylalkyl, $C_{6-7}$ heterocycloalkylalkyl, or $C_6$ heterocycloalkylalkyl or $C_7$ heterocycloalkylalkyl. In a heterocycloalkylalkyl, the heteroatomic group can be selected from —O—, —S—, —NH—, —N(—CH$_3$)—, —SO—, —SO$_2$—, —Si—, —B—, or the heteroatomic group can be selected from —O— and —NH—, or the heteroatomic group can be —O— or —NH—.

"Parent aromatic ring system" refers to an unsaturated cyclic or polycyclic ring system having a cyclic conjugated π (pi) electron system with 4n+2 electrons (Hückel rule). Included within the definition of "parent aromatic ring system" are fused ring systems in which one or more of the rings are aromatic and one or more of the rings are saturated or unsaturated, such as, for example, fluorene, indane, indene, and phenalene. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, and trinaphthalene.

"Hydrates" refers to incorporation of water into to the crystal lattice of a compound described herein, in stoichiometric proportions, resulting in the formation of an adduct. Methods of making hydrates include, for example, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism.

"Parent aromatic ring system" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, and phenalene. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of π-electrons corresponding to the Hückel rule (4n+2). Examples of heteroatoms to replace the carbon atoms include N, P, O, S, Si, and B. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, and xanthene. Examples of parent heteroaromatic ring systems include arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, and oxazolidine.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of suitable inorganic acids include hydrochloric acid, hydrobromic acid, sulfuric acid, nitric acid, and phosphoric acid. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, and N-methylglucamine. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (1) or a pharmaceutically acceptable salt thereof and at least one pharmaceutically acceptable vehicle, with which the compound of Formula (1) or a pharmaceutically acceptable salt thereof is administered to a patient. Pharmaceutically acceptable vehicles are known in the art.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by administering a compound provided by the present disclosure in a preventative fashion. The application of a therapeutic agent for preventing or prevention of a disease of disorder is known as prophylaxis. Compounds provided by the present disclosure can provide superior prophylaxis because of lower long-term side effects over long time periods.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, such as water or ethanol. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water. "Solvate" refers to incorporation of solvents into to the crystal lattice of a compound described herein, in stoichiometric proportions, resulting in the formation of an adduct. Methods of making solvates include, for example, storage in an atmosphere containing a solvent, dosage forms that include the solvent, or routine pharmaceutical processing steps such as, for example, crystallization (i.e., from solvent or mixed solvents) vapor diffusion. A solvate may also be formed, under certain circumstances, from other crystalline solvates or hydrates upon exposure to the solvent or upon suspension material in solvent. A solvate may crystallize in more than one form resulting in solvate polymorphism.

"A compound provided by the present disclosure" refers to a compound encompassed by Formula (1) and pharmaceutically salts thereof. A compound provided by the present disclosure can further include a compound encompassed by Formula (1) such as a pharmaceutically acceptable salt, a solvate, a hydrate, and/or a prodrug of any of the foregoing.

Compounds provided by the present disclosure also include crystalline and amorphous forms of the compounds including, for example, polymorphs, pseudopolymorphs, solvates, hydrates, unsolvated polymorphs (including anhydrates), conformational polymorphs, and amorphous forms of the compounds, as well as mixtures thereof "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

"Substituted" refers to a group in which one or more hydrogen atoms are independently replaced with the same or different substituent(s). Each substituent can be independently selected, for example, from deuterio, halogen, —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R is independently selected from hydrogen and C$_{1-6}$ alkyl. Each substituent can be independently selected, for example, from deuterio, halogen, —NH$_2$, —OH, C$_{1-3}$ alkoxy, and C$_{1-3}$ alkyl, trifluoromethoxy, and trifluoromethyl. Each substituent can be independently selected from deuterio, —OH, methyl, ethyl, trifluoromethyl, methoxy, ethoxy, and trifluoromethoxy. Each substituent can be selected from deuterio, C$_{1-3}$ alkyl, =O, C$_{1-3}$ alkyl, C$_{1-3}$ alkoxy, and phenyl. Each substituent can be selected from, for example, deuterio, —OH, —NH$_2$, C$_{1-3}$ alkyl, and C$_{1-3}$ alkoxy.

"Sustained release" refers to release of a compound from a dosage form of a pharmaceutical composition at a rate effective to achieve a therapeutic or prophylactic concentration of the compound or active metabolite thereof, in the systemic circulation of a patient over a prolonged period of time relative to that achieved by administration of an immediate release formulation of the same compound by the same route of administration. In some embodiments, release of a compound occurs over a time period of at least about 4 hours, such as at least about 8 hours, at least about 12 hours, at least about 16 hours, at least about 20 hours, and in some embodiments, at least about 24 hours.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also refers to delaying the onset of the disease or delaying the onset of at least one or more symptoms thereof in a patient who may be exposed to or predisposed to a disease or disorder even though that patient does not yet experience or display symptoms of the disease.

"Therapeutically effective amount" refers to the amount of a compound that, when administered to a patient for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

"Binding affinity" refers to the strength of the binding interaction between a single biomolecule and its ligand/binding partner. Binding affinity is expressed as the $IC_{50}$ value. Binding affinity can be determined by phage ELISA competition assays.

"Modulate" and "modulation" refer to a change in biological activity for a biological molecule such as, for example, a protein, gene, peptide, or antibody, where such change may relate to an increase in biological activity such as, for example, increased activity, agonism, activation, expression, upregulation, and/or increased expression, or decrease in biological activity such as, for example, decreased activity, antagonism, suppression, deactivation, downregulation, and/or decreased expression, for the biological molecule.

For example, the compounds described herein can modulate such as inhibit the p38α MAPK protein. Compounds provided by the preset disclosure can selectively inhibit p38α MAPK protein as compared to other MAPK or p38 MAPK isoforms. Compounds provided by the present disclosure can selectively modulate such as selectively inhibit p38α MAPK protein as compared to other MAPK or p38 MAPK proteins.

"Moiety" refers to a specific segment or functional group of a molecule. Chemical moieties are often recognized chemical entities embedded in or appended to a molecule.

Reference is now made in detail to certain embodiments of compounds, compositions, and methods. The disclosed embodiments are not intended to be limiting of the claims. To the contrary, the claims are intended to cover all alternatives, modifications, and equivalents.

Compounds provided by the present disclosure are selective inhibitors of the p38α MAPK protein. Pharmaceutical compositions provided by the present disclosure include compounds provided by the present disclosure. Compounds and pharmaceutical compositions provided by the present disclosure can be used to treat diseases in which the disease is treated by inhibiting the p38α MAPK protein.

Inhibitors of catalytic activity associated with p38α MAPK can not only block expression of proinflammatory cytokines but can also block other p38α MAPK signaling pathways that are important for establishing and maintaining homeostasis.

The compounds provided by the present disclosure can target the substrate binding groove of p38α MAPK, which extends between two acidic patches, the CD and ED domains, and is distinct from the DEF substrate-binding pocket. Downstream substrates, upstream activating kinases, and possibly scaffolding molecules interact with p38 MAPK through the CD and ED domains. Compounds provided by the present disclosure can bind in a selective manner to p38α MAPK and not to p38β MAPK, can stabilize endothelial barrier function in human lung microvascular endothelial cells (HMVECLs), and can inhibit LPS-induced proinflammatory gene expression in THP1 cells.

Compounds provided by the present disclosure include compounds of Formula (1) in which $R^2$ comprises a fused ring, and compounds of Formula (1) in which $R^2$ comprises a monocyclic ring.

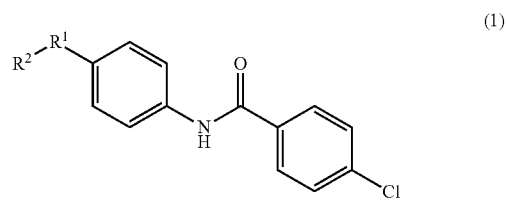

(1)

A compound provided by the present disclosure can have the structure of Formula (1):

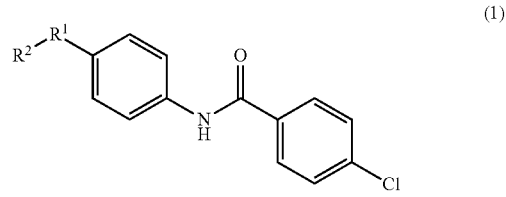

(1)

or a pharmaceutically acceptable salt thereof, wherein, $R^1$ can be selected from $C_{1-4}$ alkanediyl, $C_{1-4}$ heteroalkanediyl, substituted $C_{1-4}$ alkanediyl, and substituted $C_{1-4}$ heteroalkanediyl; and $R^2$ can be selected from a moiety of Formula (2a), a moiety of Formula (2b), a moiety of Formula (2c), $C_{8-16}$ heterobicycloalkyl, and substituted $C_{8-16}$ heterobicycloalkyl:

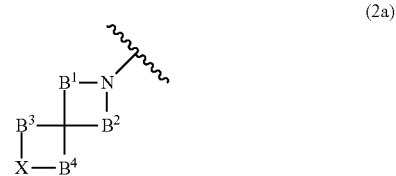

(2a)

-continued

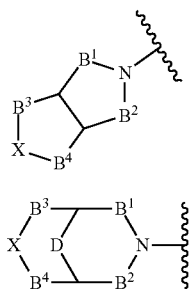

(2b)

(2c)

wherein,
each of $B^1$, $B^2$, $B^3$, and $B^4$ can be independently selected from —(CH(—$R^4$))$_n$—, wherein,
each n can be independently selected from, 0, 1, 2, 3, and 4;
both $B^1$ and $B^2$ are not 0;
both $B^3$ and $B^4$ are not 0; and
each $R^4$ can be independently selected from hydrogen, —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl;
D can be selected from methane-diyl and ethane-diyl; and
X can be selected from —O—, —CH(—OH)—, —$NR^3$—, and —$SO_2$—, wherein $R^3$ can be selected from hydrogen, $C_{1-6}$ alkyl, $C_{1-6}$ cycloalkyl, $C_6$ aryl, $C_{1-6}$ heteroalkyl, $C_{1-6}$ heterocycloalkyl, $C_{5-6}$ heteroaryl, substituted $C_{1-6}$ alkyl, substituted $C_{1-6}$ cycloalkyl, substituted $C_6$ aryl, substituted $C_{1-6}$ heteroalkyl, substituted $C_{1-6}$ heterocycloalkyl, and substituted $C_{5-6}$ heteroaryl.

In a compound of Formula (1), each of the one or more substituents can be independently selected from —OH, =O, —$NH_2$, —$NO_2$, $C_{1-6}$ alkyl, $C_{1-6}$ cycloalkyl, $C_6$ aryl, $C_{1-6}$ heteroalkyl, $C_{1-6}$ heterocycloalkyl, $C_{5-6}$ heteroaryl, substituted $C_{1-6}$ alkyl, substituted $C_{1-6}$ cycloalkyl, substituted $C_6$ aryl, substituted $C_{1-6}$ heteroalkyl, substituted $C_{1-6}$ heterocycloalkyl, and substituted $C_{5-6}$ heteroaryl.

In a compound of Formula (1), each of the one or more substituents can be independently selected from —OH, =O, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

In a compound of Formula (1), each of the one or more substituents can be independently selected from —OH, =O, and $C_{1-3}$ alkyl.

In a compound of Formula (1), $R^1$ can be $C_{1-4}$ alkanediyl.
In a compound of Formula (1), $R^1$ can be ethanediyl.
In a compound of Formula (1), $R^1$ can be methanediyl.
In a compound of Formula (1), $R^2$ can be a moiety of Formula (2a):

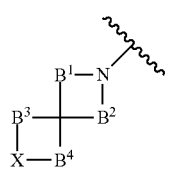

(2a)

In a moiety of Formula (2a), each of $B^1$, $B^2$, $B^3$, and $B^4$ can be independently selected from —(CH$_2$)$_n$—.

In a moiety of Formula (2a), each of $B^1$ and $B^2$ can be independently selected from —(CH$_2$)$_n$—.

In a moiety of Formula (2a), each of $B^1$, $B^2$, and $B^3$ can be independently selected from —(CH$_2$)$_n$—.

In a moiety of Formula (2a), each of $B^1$, $B^2$, and $B^4$ can be independently selected from —(CH$_2$)$_n$—.

In a moiety of Formula (2a), one of $B^1$, $B^2$, $B^3$, and $B^4$ comprises —CH(—$R^4$)—, wherein $R^4$ can be selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

In a moiety of Formula (2a), two of $B^1$, $B^2$, $B^3$, and $B^4$ independently comprise —CH(—$R^4$)—, wherein $R^4$ can be selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

In a moiety of Formula (2a), three of $B^1$, $B^2$, $B^3$, and $B^4$ independently comprise —CH(—$R^4$)—, wherein $R^4$ can be selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

In a moiety of Formula (2a), each of $B^1$, $B^2$, $B^3$, and $B^4$ independently comprises —CH(—$R^4$)—, wherein $R^4$ can be selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

In a moiety of Formula (2a), each n can be independently selected from 0, 1, 2, and 3.

In a moiety of Formula (2a), each n can be independently selected from 1, 2, and 3.

In a moiety of Formula (2a), n in each of $B^1$ and $B^2$ can be independently selected from 1 and 2; and n in each of $B^3$ and $B^4$ can be 2.

In a moiety of Formula (2a), n in each of $B^1$ and $B^2$ can be 1; and n in each of $B^3$ and $B^4$ can be 2.

In a moiety of Formula (2a), n in each of $B^1$ and $B^2$ can be 2; and n in each of $B^3$ and $B^4$ can be 1.

In a moiety of Formula (2a), n in each of $B^1$ and $B^2$ can be 2; and n in each of $B^3$ and $B^4$ can be 2.

In a moiety of Formula (2a), n in each of $B^1$ and $B^2$ can be 1; and n in each of $B^3$ and $B^4$ can be 1.

In a moiety of Formula (2a), X can be —O—.
In a moiety of Formula (2a), X can be —CH(—OH)—.
In a moiety of Formula (2a), X can be —$SO_2$—.
In a moiety of Formula (2a), X can be —$NR^3$—.
In a moiety of Formula (2a), X can be —$NR^3$—, and $R^3$ can be selected from hydrogen, $C_{1-3}$ alkyl, $C_{1-3}$ heteroalkyl, substituted $C_{1-3}$ alkyl, and substituted $C_{1-3}$ heteroalkyl.

In a moiety of Formula (2a), X can be —$NR^3$—, and $R^3$ can be —C(=O)—$CH_3$.

In a moiety of Formula (2a), X can be —$NR^3$—, and $R^3$ can be —$CH_3$.

In a moiety of Formula (2a), $B^1$ can be —(CH$_2$)$_2$—; $B^2$ can be —CH$_2$—; $B^3$ can be —(CH$_2$)$_n$— wherein n is selected from 0, 1, 2, and 3; $B^3$ can be —(CH$_2$)$_{3n}$—; and X is O.

A moiety of Formula (2a) can be selected from a moiety of Formula (2a.1) to (2a.4):

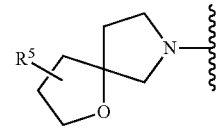

(2d.1)

(2d.2)

(2d.3)

(2d.4)

where $R^5$ is selected from hydrogen (unsubstituted), —OH, —NH$_2$, —NR$_2$ wherein each R is independently selected from hydrogen and C$_{1-3}$ alkyl, —NO$_2$, =O, C$_{1-3}$ alkoxy, and C(=O)—R where R is C$_{1-3}$ alkyl.

In a compound of Formula (1), $R^2$ can be a moiety of Formula (2b):

(2b)

In a moiety of Formula (2b), each of $B^1$, $B^2$, $B^3$, and $B^4$ can be independently selected from —(CH$_2$)$_n$—.

In a moiety of Formula (2b), each of $B^1$ and $B^2$ can be independently selected from —(CH$_2$)$_n$—.

In a moiety of Formula (2b), each of $B^1$, $B^2$, and $B^3$ can be independently selected from —(CH$_2$)$_n$—.

In a moiety of Formula (2b), each of $B^1$, $B^2$, and $B^4$ can be independently selected from —(CH$_2$)$_n$—.

In a moiety of Formula (2b), one of $B^1$, $B^2$, $B^3$, and $B^4$ comprises —CH(—R$^4$)—, wherein $R^4$ can be selected from —OH, —NH$_2$, —NO$_2$, C$_{1-3}$ alkyl, C$_{1-3}$ heteroalkyl, substituted C$_{1-3}$ alkyl, and substituted C$_{1-3}$ heteroalkyl.

In a moiety of Formula (2b), two of $B^1$, $B^2$, $B^3$, and $B^4$ independently comprise —CH(—R$^4$)—, wherein $R^4$ can be selected from —OH, —NH$_2$, —NO$_2$, C$_{1-3}$ alkyl, C$_{1-3}$ heteroalkyl, substituted C$_{1-3}$ alkyl, and substituted C$_{1-3}$ heteroalkyl.

In a moiety of Formula (2b), three of $B^1$, $B^2$, $B^3$, and $B^4$ independently comprise —CH(—R$^4$)—, wherein $R^4$ can be selected from —OH, —NH$_2$, —NO$_2$, C$_{1-3}$ alkyl, C$_{1-3}$ heteroalkyl, substituted C$_{1-3}$ alkyl, and substituted C$_{1-3}$ heteroalkyl.

In a moiety of Formula (2b), each of $B^1$, $B^2$, $B^3$, and $B^4$ independently comprises —CH(—R$^4$)—, wherein $R^4$ can be selected from —OH, —NH$_2$, —NO$_2$, C$_{1-3}$ alkyl, C$_{1-3}$ heteroalkyl, substituted C$_{1-3}$ alkyl, and substituted C$_{1-3}$ heteroalkyl.

In a moiety of Formula (2b), each n can be independently selected from 1 and 2.

In a moiety of Formula (2b), each n can be 1.

In a moiety of Formula (2b), n in each of $B^1$ and $B^2$ can be 1; and n in each of $B^3$ and $B^4$ can be 2.

In a moiety of Formula (2b), n in each of $B^1$ and $B^2$ can be 2; and n in each of $B^3$ and $B^4$ can be 1.

In a moiety of Formula (2b), n in each of $B^1$, $B^2$, and $B^3$ can be 1, and n in $B^4$ can be 2.

In a moiety of Formula (2b), n in each of $B^1$, $B^2$, and $B^3$ can be 2, and n in $B^4$ can be 1.

In a moiety of Formula (2b), X can be —O—.

In a moiety of Formula (2b), X can be —CH(—OH)—.

In a moiety of Formula (2b), X can be —SO$_2$—.

In a moiety of Formula (2b), X can be —NR$^3$—.

In a moiety of Formula (2b), X can be —NR$^3$—, and $R^3$ can be selected from hydrogen, C$_{1-3}$ alkyl, C$_{1-3}$ heteroalkyl, substituted C$_{1-3}$ alkyl, and substituted C$_{1-3}$ heteroalkyl.

In a moiety of Formula (2b), X can be —NR$^3$—, and $R^3$ can be —C(=O)—CH$_3$.

In a moiety of Formula (2b), X can be —NR$^3$—, and $R^3$ can be —CH$_3$.

In a compound of Formula (1), $R^2$ can be a moiety of Formula (2c):

(2c)

In a moiety of Formula (2c), each of $B^1$, $B^2$, $B^3$, and $B^4$ can be independently selected from —(CH$_2$)$_n$—.

In a moiety of Formula (2c), each of $B^1$ and $B^2$ can be independently selected from —(CH$_2$)$_n$—.

In a moiety of Formula (2c), each of $B^1$, $B^2$, and $B^3$ can be independently selected from —(CH$_2$)$_n$—.

In a moiety of Formula (2c), each of $B^1$, $B^2$, and $B^4$ can be independently selected from —(CH$_2$)$_n$—.

In a moiety of Formula (2c), one of $B^1$, $B^2$, $B^3$, and $B^4$ comprises —CH(—R$^4$)—, wherein $R^4$ can be selected from —OH, —NH$_2$, —NO$_2$, C$_{1-3}$ alkyl, C$_{1-3}$ heteroalkyl, substituted C$_{1-3}$ alkyl, and substituted C$_{1-3}$ heteroalkyl.

In a moiety of Formula (2c), two of $B^1$, $B^2$, $B^3$, and $B^4$ independently comprise —CH(—R$^4$)—, wherein $R^4$ can be selected from —OH, —NH$_2$, —NO$_2$, C$_{1-3}$ alkyl, C$_{1-3}$ heteroalkyl, substituted C$_{1-3}$ alkyl, and substituted C$_{1-3}$ heteroalkyl.

In a moiety of Formula (2c), three of $B^1$, $B^2$, $B^3$, and $B^4$ independently comprise —CH(—R$^4$)—, wherein $R^4$ can be selected from —OH, —NH$_2$, —NO$_2$, C$_{1-3}$ alkyl, C$_{1-3}$ heteroalkyl, substituted C$_{1-3}$ alkyl, and substituted C$_{1-3}$ heteroalkyl.

In a moiety of Formula (2c), each of $B^1$, $B^2$, $B^3$, and $B^4$ independently comprise —CH(—R$^4$)—, wherein $R^4$ can be selected from —OH, —NH$_2$, —NO$_2$, C$_{1-3}$ alkyl, C$_{1-3}$ heteroalkyl, substituted C$_{1-3}$ alkyl, and substituted C$_{1-3}$ heteroalkyl.

In a moiety of Formula (2c), each n can be independently selected from 1 and 2.

In a moiety of Formula (2c), each n can be 1.

In a moiety of Formula (2c),
n in each of $B^1$ and $B^2$ can be 1; and
n in each of $B^3$ and $B^4$ can be 2.

In a moiety of Formula (2c),
n in each of $B^1$ and $B^2$ can be 2; and
n in each of $B^3$ and $B^4$ can be 1.

In a moiety of Formula (2c), each n can be 2.

In a moiety of Formula (2c), D can be methanediyl.
In a moiety of Formula (2c), D can be ethanediyl.
In a moiety of Formula (2c), X can be —O—.
In a moiety of Formula (2c), X can be —CH(—OH)—.
In a moiety of Formula (2c), X can be —SO$_2$—.
In a moiety of Formula (2c), X can be —NR$^3$—.
In a moiety of Formula (2c), X can be —NR$^3$—, and R$^3$ can be selected from hydrogen, C$_{1-3}$ alkyl, C1-3 heteroalkyl, substituted C$_{1-3}$ alkyl, and substituted C$_{1-3}$ heteroalkyl.
In a moiety of Formula (2c), X can be —NR$^3$—, and R$^3$ can be —C(═O)—CH$_3$.
In a moiety of Formula (2c), X can be —NR$^3$—, and R$^3$ can be —CH$_3$.

A compound of Formula (1) can be selected from:
N-(4-((2-oxa-6-azaspiro[3.3]heptan-6-yl)methyl)phenyl)-4-chlorobenzamide (3);
N-(4-((7-oxa-2-azaspiro[3.5]nonan-2-yl)methyl)phenyl)-4-chlorobenzamide (4);
N-(4-((8-oxa-2-azaspiro[4.5]decan-2-yl)methyl)phenyl)-4-chlorobenzamide (5);
N-(4-((1-oxa-7-azaspiro[4.4]nonan-7-yl)methyl)phenyl)-4-chlorobenzamide (6);
N-(4-(((1R,5S)-3-oxa-7-azabicyclo[3.3.1]nonan-7-yl)methyl)phenyl-4-chlorobenzamide (9); and
4-chloro-N-(4-(((3aR,6aS)-tetrahydro-1H-furo[3,4-c]pyrrol-5(3H)-yl)methyl)phenyl)benzamide (10);
or a pharmaceutically acceptable salt of any of the foregoing.

A compound provided by the present disclosure can have the structure of Formula (1):

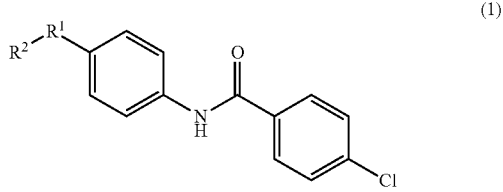

(1)

or a pharmaceutically acceptable salt thereof, wherein,
R$^1$ can be selected from C$_{1-4}$ alkanediyl, C$_{1-4}$ heteroalkanediyl, substituted C$_{1-4}$ alkanediyl, and substituted C$_{1-4}$ heteroalkanediyl; and
R$^2$ can be a moiety of Formula (2d):

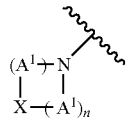

(2d)

wherein,
each A$^1$ and A$^2$ can be independently selected from —CH$_2$—, —CH(—R$^5$)—, and —C(═O)—, wherein, each R$^5$ can be independently selected from —OH, —NH$_2$, —NO$_2$, C$_{1-6}$ alkyl, C$_{1-6}$ cycloalkyl, C$_6$ aryl, C$_{1-6}$ heteroalkyl, C$_{1-6}$ heterocycloalkyl, C$_{5-6}$ heteroaryl, substituted C$_{1-6}$ alkyl, substituted C$_{1-6}$ cycloalkyl, substituted C$_6$ aryl, substituted C$_{1-6}$ heteroalkyl, substituted C$_{1-6}$ heterocycloalkyl, and substituted C$_{5-6}$ heteroaryl;
one or more of A$^1$ and A$^2$ can be independently selected from —CH(—R$^5$)— and —C(═O)—;
each n can be independently selected from, 1, 2, 3, and 4; and
X can be selected from —O—, —CH(—OH)—, —NR$^3$—, and —SO$_2$—, wherein R$^3$ can be selected from hydrogen, C$_{1-6}$ alkyl, C$_{5-8}$ cycloalkyl, C$_6$ aryl, C$_{6-12}$ cycloalkylalkyl, C$_{7-10}$ arylalkyl, C$_{1-6}$ heteroalkyl, C$_{5-8}$ heterocycloalkyl, C$_{5-6}$ heteroaryl, C$_{6-12}$ heterocycloalkylalkyl, C$_{7-10}$ heteroarylalkyl, substituted C$_{1-6}$ alkyl, substituted C$_{5-8}$ cycloalkyl, substituted C$_6$ aryl, substituted C$_{6-12}$ cycloalkylalkyl, substituted C$_{7-10}$ arylalkyl, substituted C$_{1-6}$ heteroalkyl, substituted C$_{5-8}$ heterocycloalkyl, substituted C$_{5-6}$ heteroaryl, substituted C$_{6-12}$ heterocycloalkylalkyl, and substituted C$_{7-10}$ heteroarylalkyl.

In a moiety of Formula (2d), R$^1$ can be C$_{1-4}$ alkanediyl.
In a moiety of Formula (2d), R$^1$ can be ethanediyl.
In a moiety of Formula (2d), R$^1$ can be methanediyl.
In a moiety of Formula (2d), each n can be independently selected from 1, 2, and 3.
In a moiety of Formula (2d), each n can be 2.
In a moiety of Formula (2d), each n can be 3.
In a moiety of Formula (2d), each n can be 4.
In a moiety of Formula (2d), one or more of A$^1$ and A$^2$ can be independently selected from —CH(—R$^5$)—, wherein R$^5$ can be C$_{1-3}$ alkyl; and —C(═O)—.
In a moiety of Formula (2d), one or more of A$^1$ and A$^2$ can be independently selected from —CH(—R$^5$)—, wherein R$^5$ can be C$_{1-3}$ alkyl.
In a moiety of Formula (2d), one or more of A$^1$ and A$^2$ can be —C(═O)—.
In a moiety of Formula (2d), X can be —O—.
In a moiety of Formula (2d), X can be —CH(—OH)—.
In a moiety of Formula (2d), X can be —SO$_2$—.
In a moiety of Formula (2d), X can be —NR$^3$—.
In a moiety of Formula (2d), X can be —NR$^3$—, and R$^3$ can be selected from hydrogen, C$_{1-3}$ alkyl, C$_{1-3}$ heteroalkyl, substituted C$_{1-3}$ alkyl, and substituted C$_{1-3}$ heteroalkyl.
In a moiety of Formula (2d), X can be —NR$^3$—, and R$^3$ can be —C(═O)—CH$_3$.
In a moiety of Formula (2d), X can be —NR$^3$—, and R$^3$ can be —CH$_3$.

A compound of Formula (1) can be selected from:
2-chloro-N-(4-(morpholinomethyl)phenyl)pyrimidine-5-carboxamide (1);
N-(4-((1,4-oxazepan-4-yl)methyl)phenyl)-4-chlorobenzamide (2);
4-chloro-N-(4-(((2S,6R)-2,6-dimethylmorpholino)methyl)phenyl)benzamide (7);
4-chloro-N-(4-(((2S,6S)-2,6-dimethylmorpholino)methyl)phenyl)benzamide (8);
4-chloro-N-(4-((4-hydroxypiperidin-1-yl)methyl)phenyl)benzamide (11);
4-chloro-N-(4-((3-hydroxypiperidin-1-yl)methyl)phenyl)benzamide (12);
4-chloro-N-(4-((3-hydroxypyrrolidin-1-yl)methyl)phenyl)benzamide (13);
N-(4-((4-acetylpiperazin-1-yl)methyl)phenyl)-4-chlorobenzamide (14);
4-chloro-N-(4-((3-oxopiperazin-1-yl)methyl)phenyl)benzamide (15);
4-chloro-N-(4-((4-methyl-3-oxopiperazin-1-yl)methyl)phenyl)benzamide (16); and
4-chloro-N-(4-((4-methylpiperazin-1-yl)methyl)phenyl)benzamide (17);
or a pharmaceutically acceptable salt of any of the foregoing.

In a moiety of Formula (2d), $A^1$ can be —$(CH_2)_n$— where n can be an integer from 1 to 4; $A^2$ can be —$(CH_2)_{5-n}$—; and X is O.

A moiety of Formula (2d) can have the structure of Formula (2d.1) or Formula (2d.2):

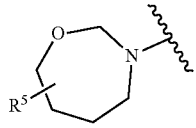

(2d.1)

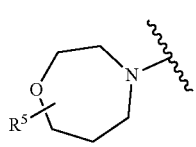

(2d.2)

where $R^5$ is selected from hydrogen (unsubstituted), —OH, —$NH_2$, —$NR_2$ wherein each R is independently selected from hydrogen and $C_{1-3}$ alkyl, —$NO_2$, =O, $C_{1-3}$ alkoxy, and C(=O)—R where R is $C_{1-3}$ alkyl.

In a moiety of Formula (2d), $A^1$ can be —$(CH_2)_n$— where n is 1 or 2; $A^2$ can be —$(CH_2)_{3-n}$—; and X is —N(—C(=O)—$R^6$)— where $R^6$ is selected from.

A moiety of Formula (2d) can be selected from a moiety of Formula (2d.3) and Formula (2d.4):

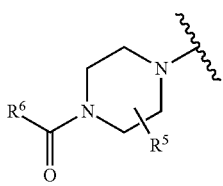

(2d.3)

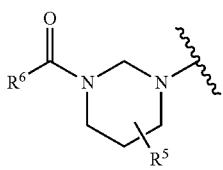

(2d.4)

wherein, $R^5$ is selected from hydrogen (unsubstituted), —OH, —$NH_2$, —$NR_2$ wherein each R is independently selected from hydrogen and $C_{1-3}$ alkyl, —$NO_2$, =O, $C_{1-3}$ alkoxy, and C(=O)—R where R is $C_{1-3}$ alkyl; and $R^6$ is selected from $C_{1-6}$ alkyl and $C_{1-6}$ alkoxy.

In a moiety of Formula (2d), $A^1$ can be —$(CH_2)_n$— where n is 1 or 2; $A^2$ can be —$(CH_2)_{3-n}$—; and X can be O, and can be comprise one or two —$CH_3$ substituents.

A moiety of Formula (2d) can have the structure of Formula (2d.5):

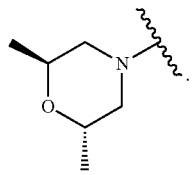

(2d.5)

A compound provided by the present disclosure can have the structure of Formula (1):

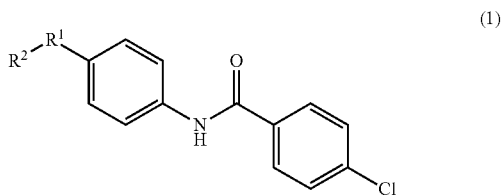

(1)

or a pharmaceutically acceptable salt thereof, where, $R^1$ can be selected from $C_{1-4}$ alkanediyl; and $R^2$ is selected from a substituted or unsubstituted moiety of any one of Formula (2a.1) to (2a.4) and (2d.1) to (2d.5):

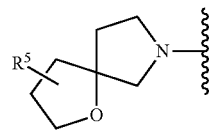

(2a.1)

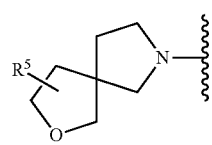

(2a.2)

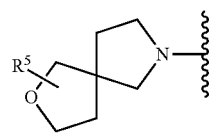

(2a.3)

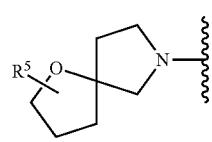

(2a.4)

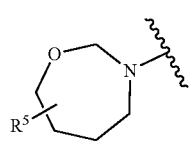

(2d.1)

-continued (2d.2)

(2d.3)

(2d.4)

(2d.5)

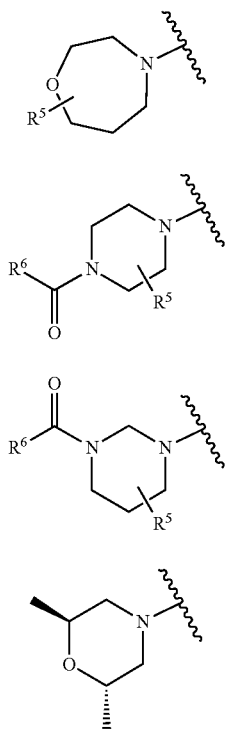

wherein,

R⁵ is selected from hydrogen (unsubstituted), —OH, —NH₂, —NR₂ wherein each R is independently selected from hydrogen and $C_{1-3}$ alkyl, —NO₂, =O, $C_{1-3}$ alkoxy, and C(=O)—R where R is $C_{1-3}$ alkyl; and R⁶ is selected from $C_{1-6}$ alkyl and $C_{1-6}$ alkoxy.

In a compound of Formula (1), R¹ is selected from methane-diyl, ethane-diyl, and n-propane-diyl.

In a compound of Formula (1), R¹ is methane-diyl.

In a compound of Formula (1), R² is selected from an unsubstituted moiety of any one of (2a.1) to (2a.4) and (2d.1) to (2d.5).

In a compound of Formula (1), R² is selected from a substituted moiety of any one of Formula ((2a.1) to (2a.4) and (2d.1) to (2d.5).

In a compound of Formula (1), the substituted moiety can have the structure of any one of Formula (2a.1) to (2a.4) and (2d.1) to (2d.5):

(2a.1)

(2a.2)

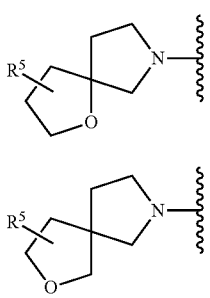

-continued (2a.3)
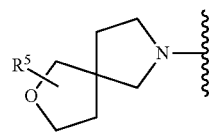

(2a.4)
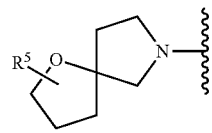

(2d.1)
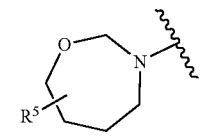

(2d.2)
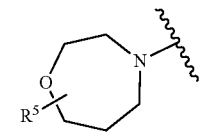

(2d.3)
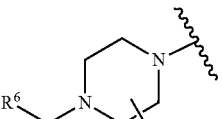

(2d.4)
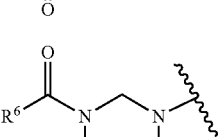

(2d.5)
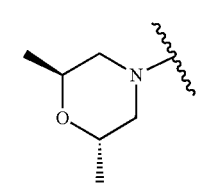

wherein,

R⁵ is selected from hydrogen (unsubstituted), —OH, —NH₂, —NR₂ wherein each R is independently selected from hydrogen and C1-3 alkyl, —NO₂, =O, $C_{1-3}$ alkoxy, and C(=O)—R where R is $C_{1-3}$ alkyl; and R⁶ is selected from $C_{1-6}$ alkyl and $C_{1-6}$ alkoxy.

A compound of Formula (1) can be a solvate, a pharmaceutically acceptable salt, or a combination thereof.

In a compound of Formula (1), a pharmaceutically acceptable salt can be the hydrochloride salt.

In a compound of Formula (1), a pharmaceutically acceptable salt can be the dihydrochloride salt.

A compound of Formula (1) can be a pharmaceutically acceptable salt of a compound of Formula (1), a hydrate thereof, or a solvate of any of the foregoing.

A compound provided by the present disclosure can be a p38 MAPK inhibitor and/or a modulator of p38α MAPK protein activity.

A compound provided by the present disclosure can bind to p38α MAPK in a selective manner. A selective p38α

MAPK inhibitor provided by the present disclosure can have a higher binding affinity to the target pocket of p38α MAPK than to p38β MAPK. A compound provided by the preset disclosure can selectively inhibit p38α MAPK. The p38α MAPK inhibitor can bind to p38α MAPK near the substrate binding groove of p38α MAPK, which extends between two acidic patches referred to as the CD and ED domains. The binding pocket can be defined at least by residues R49, H107, L108, and K165 of p38α MAPK. The binding pocket can be defined at least by residues R49, H107, L108, M109, G110, A157, V158, E163, L164, and K165 of p38α MAPK.

Selective binding of a compound provided by the present disclosure to p38α MAPK can be confirmed using complementary technologies. For example, a selective p38α MAPK inhibitor can show a concentration-dependent increase in melting temperature of p38α but not p38β as determined using differential scanning fluorimetry (DSF), which detects ligand-induced protein stabilization. STD-NMR, which measures low affinity protein/ligand binding via non-scalar magnetization transfer from protein to ligand protons, can be used to confirm specific compound binding to p38α and localized the interaction to its aromatic rings. A p38α MAPK inhibitor can cause a concentration-dependent increase in melting temperature of p38α MAPK. The difference in melting temperature $T_m$ can be measured at a p38α MAPK inhibitor concentration of between 1 nM and 1,000 μM such as at a concentration of 100 μM. For example, the difference in the melting temperature can be from 0.1° C. and about 2° C.

A compound provided by the present disclosure can interact with a pocket near the ED substrate docking site of p38 α MAPK.

A compound provided by the present disclosure can bind to p38α MAPK near the substrate binding groove of p38α MAPK, which extends between the CD and ED domains.

A compound provided by the present disclosure can inhibit MK2 phosphorylation through interaction with p38α MAPK.

A compound provided by the present disclosure can competitively bind to p38α MAPK with 4-chloro-N-(4-((1,1-dioxidothiomorpholino)methyl)phenyl)benzamide.

A compound provided by the present disclosure can bind to the p38α MAPK subunit with an $IC_{50}$ that is less than the $IC_{50}$ for binding to the p38β MAPK subunit.

A p38α MAPK inhibitor provided by the present disclosure can have a log P, for example, from −5 to 10, from −3 to 8, from 0 to 5, 0.1 to 3, from 0.1 to 1, from 0.5 to 1.5, from 0.75 to 2, from 1 to 2.5, or from 1.75 to 3. Log P is a measure of drug solubility and is defined as the logarithm of the octanol/water partition coefficient of the compound.

Phosphorylation of MK2 requires binding to the ED site adjacent to the target pocket in p38α MAPK. The target pocket can be defined by amino acids R49, H107, L108, and K165 in p38α MAPK. The target pocket can be defined by amino acids selected from R49, H107, L108, M109, G110, A157, V158, E163, L164, and K165 in p38α MAPK. The target pocket can be defined by the amino acids R49, H107, L108, M109, G110, A157, V158, E163, L164, and K165 in p38α MAPK.

p38α MAPK inhibitors provided by the present disclosure can at least partially inhibit MK2 phosphorylation. For example, Western blotting can be used to measure inhibition of MK2 phosphorylation in anisomycin-stimulated HeLa cells by a compound provided by the present disclosure.

A p38α MAPK inhibitor provided by the present disclosure can stabilize an endothelial or epithelial barrier function. Endothelial barrier permeability can be measured by separate or combined exposure to TNFa and hyperthermia, followed by measurement of permeably for 10 kDa dextran. For example, endothelial barrier stabilization can be assessed by pretreating with a compound provided by the present disclosure, preceded and followed by permeability measurements, where stabilization can be expressed as a percent reduction in the before and after pretreatment permeability increase. A permeability increase for 10 kDa dextran can be reduced by between 5% to by more than 100% such as, for example, by greater than 5%, greater than 10%, greater than 20%, greater than 40%, greater than 60%, greater than 80%, or greater than 100%.

A p38α MAPK inhibitor provided by the present disclosure can modulate TNFa-induced gene expression in human lung microvascular endothelial cells (HMVECLs) as determined using, for example, RNASeq. For example, HMVECLs can be pretreated for a period of time with a p38α MAPK inhibitor at an appropriate concentration and then stimulated with TNFa for a period of time. A p38α MAPK inhibitor provided by the present disclosure can inhibit genes such as PRRG4, TSLP, CCLI 7, EXOC3L4, MMP9, IDOI, CXCL1O, CD200, SLCI5A3, VDR, ILIB, GPR88, CD207, TCHH, HAS3, GBPIPI, MUC4, ELOVL7, CXCL11, GBP4, PLAIA, and/or CXCL5.

The effects of a p38α MAPK inhibitor on inflammatory cytokine expression can be determined by pretreating PMA-differentiated THPI cells with a p38α MAPK inhibitor, then stimulating with LPS, and harvesting RNA a period of time later for analysis by PCR-based cytokine array. A p38α MAPK inhibitor can inhibit expression of various genes, such as IL-IA, IL-8, TNFSF8, CXCL5, CCL7, CCLI 7, TNFSF9, IL-IB, CXCLI, TNFSFI5, CCL5, CCL4, CCL20, CXCL2, TNF, or BMP6. A p38α MAPK inhibitor can inhibit expression of Smad3, which drives differentiation of Foxp3 T regulatory cells and suppresses interferon-γ. Inflammation reduction can be measured by comparing the fold change mRNA levels vs. unstimulated PMA-differentiated THPI cells at various concentrations of p38α MAPK inhibitor.

Compounds of Formula (1) can be synthesized using methods known in the art.

To prepare the synthetic precursor 4-chloro-N-(4-(chloromethyl)phenyl)benzamide (B), 4-chlorobenzoyl chloride can be added to a stirred solution of (4-aminophenyl) methanol and sodium acetate in THF (100 mL) at room temperature (23° C.) and reacted at room temperature for 1.5 h.

The reaction mixture can be extracted, and the organic extracts dried filtered and concentrated to provide 4-chloro-N-(4-(hydroxymethyl)phenyl)benzamide (A). Methanesulfonyl chloride can be added to a stirred a solution of 4-chloro-N-(4-(hydroxymethyl)phenyl)benzamide (A) in DCM at room temperature and the reaction mixture stirred at room temperature for 2 h. The reaction mixture can be extracted, washed, dried and filtered to provide the precursor 4-chloro-N-(4-(chloromethyl)phenyl)benzamide (B).

A compound of Formula (1) can be prepared by adding anhydrous potassium carbonate to a stirred mixture of compound (A) (200 mg, 0.714 mmol) and a heterocyclic moiety ($R^2$ in compounds of Formula (1)) in DMF and reacted while stirring at 50° C. for 2 h. The reaction mixture can be filtered and purified to provide a compound of Formula (1).

A compound of Formula (1) provided by the present disclosure can be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. A pharmaceutical composition provided by the present disclosure can be an injectable formulation. Pharmaceutical compositions provided by the present disclosure can be injectable intravenous formulations. Pharmaceutical compositions provided by the present disclosure can be oral formulations. Oral formulations may be oral dosage forms. A pharmaceutical composition may be formulated for intravenous administration or for subcutaneous administration.

Pharmaceutical compositions provided by the present disclosure may comprise a therapeutically effective amount of a compound of Formula (1) together with a suitable amount of one or more pharmaceutically acceptable vehicles so as to provide a composition for proper administration to a patient. Suitable pharmaceutical vehicles and methods of preparing pharmaceutical compositions are described in the art.

Assessing single patient response to therapy and qualifying a patient for optimal therapy are among the greatest challenges of modern healthcare and relate to trends in personalized medicine. A compound of Formula (1) can have target selectivity, for example, for certain cancers and immune cells. A compound of Formula (1) radiolabeled for positron emission tomography (PET) or Single Photon Emission Computed Tomography (SPECT) can be used to predict the targeting of the treatment based on a single-study, case-by-case patient analysis thus excluding patients that are expected not to benefit from treatment. PET/SPECT scans using a compound of Formula (1), once correlated to the concentration can provide a three-dimensional distribution map, which can then be used for macroscopic dose calculations.

Accordingly, it is within the capability of those of skill in the art to assay and use a compound of Formula (1) and/or pharmaceutical compositions thereof for therapy.

A compound of Formula (1) and/or pharmaceutical composition thereof can generally be used in an amount effective to achieve the intended purpose. For use to treat a disease such as cancer, an autoimmune disease or an inflammatory disease, a compound of Formula (1) and/or pharmaceutical composition thereof, may be administered or applied in a therapeutically effective amount.

The amount of a compound of Formula (1) and/or pharmaceutical composition of any of the foregoing that will be effective in the treatment of a particular disorder or condition disclosed herein will depend in part on the nature of the disorder or condition, and can be determined by standard clinical techniques known in the art. In addition, in vitro or in vivo assays may optionally be employed to help identify optimal dosage ranges. The amount of a compound of Formula (1), and/or pharmaceutical composition of any of the foregoing administered will depend on, among other factors, the patient being treated, the weight of the patient, the severity of the affliction, the manner of administration and the judgment of the prescribing physician.

A compound of Formula (1) can be assayed in vitro and in vivo, for the desired therapeutic activity, prior to use in humans. For example, in vitro assays may be used to determine whether administration of a specific compound or a combination of compounds is preferred. The compounds can also be demonstrated to be effective and safe using animal model systems.

In certain embodiments, a therapeutically effective dose of a compound of Formula (1) and/or pharmaceutical composition of any of the foregoing will provide therapeutic benefit without causing substantial toxicity. Toxicity of a compound of Formula (1) and/or pharmaceutical compositions of any of the foregoing may be determined using standard pharmaceutical procedures and may be readily ascertained by the skilled artisan. The dose ratio between toxic and therapeutic effect is the therapeutic index. A compound of Formula (1) and/or pharmaceutical composition of any of the foregoing exhibits a particularly high therapeutic index in treating disease and disorders. A dose of a compound of Formula (1) compound, and/or pharmaceutical composition of any of the foregoing will be within a range of circulating concentrations that include an effective dose with minimal toxicity.

Compounds and pharmaceutical compositions provided by the present disclosure may be included in a kit that may be used to administer the compound to a patient for therapeutic purposes. A kit may include a pharmaceutical composition comprising a compound provided by the present disclosure suitable for administration to a patient and instructions for administering the pharmaceutical composition to the patient. The kit can be suitable for treating cancer, for treating an autoimmune disease, or for treating an inflammatory disease. A kit for use in treating cancer, for treating an autoimmune disease, or for treating an inflammatory disease can comprise a compound or a pharmaceutical composition provided by the present disclosure, and instructions for administering the compound to a patient.

Compounds and pharmaceutical compositions provided by the present disclosure can be included in a container, pack, or dispenser together with instructions for administration.

Instructions supplied with a kit may be printed and/or supplied, for example, as an electronic-readable medium, a video cassette, an audiotape, a flash memory device, or may be published on an internet web site or distributed to a patient and/or health care provider as an electronic communication.

Compounds and pharmaceutical compositions provided by the present disclosure can be used to treat a disease in a patient.

Compounds and pharmaceutical compositions provided by the present disclosure can be used to treat a disease in which the etiology of the disease is associated with up-regulation and/or down-regulation of the p38α MAPK protein.

Methods provided by the present disclosure include treating a disease in a patient comprising administering to a patient in need thereof a therapeutically effective amount of a compound or composition provided by the present disclosure, wherein the disease is treated by inhibiting the p38α MAPK protein.

The p38 mitogen-activated protein kinase (MAPK) family of stress- and cytokine-activated kinases are associated with the pathogenesis of many human diseases, including, for example, cancer, rheumatoid arthritis, amyotrophic lateral sclerosis, cystic fibrosis, cardiovascular disease, multiple sclerosis, inflammatory bowel disease, chronic obstructive pulmonary disease (COPD), asthma, acute respiratory distress syndrome (ARDS), and acute lung injury (ALI). Among the many important biological processes regulated by p38 MAPK, regulation of endothelial and epithelial barrier function, leukocyte trafficking, and cytokine expression are central to the pathogenesis of acute and chronic inflammatory disorders.

Compounds and pharmaceutical compositions provided by the present disclosure may be used for treating cancer in a patient. The cancer can be, for example, a solid tumor or a metastasis.

Methods provided by the present disclosure include methods of treating cancer in a patient comprising administering to a patient in need thereof a therapeutically effective amount of a compound or pharmaceutical composition provided by the present disclosure.

Examples of suitable cancers include acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilms tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease.

Examples of suitable cancers include pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, or retinoblastoma, and the like. In other embodiments, the cancer is acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rhabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilms tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, or Waldenstorm's macroglobulinemia.

Compounds and pharmaceutical compositions provided by the present disclosure can be used to treat, for example, one or more of the following cancers: acute lymphoblastic leukemia, acute myeloid leukemia, adrenocortical carcinoma, appendix cancer, astrocytoma, atypical teratoid/rhabdoid tumor, basal cell carcinoma (nonmelanoma), B-cell lymphoma, bladder cancer, bone cancer, brain and spinal cord tumors, brain stem cancer, brain tumor, breast cancer, bronchial tumors, Burkitt lymphoma, carcinoid tumor, carcinoma of head and neck, central nervous system embryonal tumors, cerebellar astrocytoma, cerebral astrocytoma/malignant glioma, cervical cancer, chordoma, chronic lymphocytic leukemia, chronic myelogenous leukemia, colorectal cancer, craniopharyngioma, cutaneous T-cell lymphoma, desmoplastic small round cell tumor, ductal carcinoma, dye cancer, endocrine pancreas tumors (islet cell tumors), endometrial cancer, ependymoblastoma, esophageal cancer, esthesioneuroblastoma, Ewing family of tumors, extracranial germ cell tumor, extrahepatic bile duct cancer, gallbladder cancer, gastric cancer, gastrointestinal carcinoid tumor, gastrointestinal stromal tumor, gestational trophoblastic tumor, glioblastoma, glioma, hairy cell leukemia, head and neck cancer, heart cancer, hematopoetic tumors of the lymphoid lineage, hepatocellular cancer, Hodgkin lymphoma, hypopharyngeal cancer, hypothalamic and visual pathway glioma, IDs-related lymphoma, intraocular melanoma, islet cell tumors, Kaposi sarcoma, kidney cancer, Langerhans cell histiocytosis, laryngeal cancer, leukemia, lip and oral cavity cancer, male breast cancer, malignant fibrous histiocytoma, malignant germ cell tumors, malignant mesothelioma, medulloblastoma, melanoma, Merkel cell carcinoma, mesothelioma, mouth cancer, multiple endocrine neoplasia syndrome, multiple myeloma, mycosis fungoides, myelodysplastic, myeloproliferative neoplasms, nasal cavity and paranasal sinus cancer, nasopharyngeal cancer, neuroblastoma, non-Hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, pregnancy and breast cancer, primary central nervous system lymphoma, primary liver cancer, primary metastatic squamous neck cancer with occult, prostate cancer, rectal cancer, renal cell cancer, renal pelvis and ureter, respiratory tract carcinoma, retinoblastoma, rhabdomyosarcoma, salivary gland cancer, sarcoma, Sézary syndrome, skin cancer, small intestine cancer, soft tissue sarcoma, squamous cell carcinoma (nonmelanoma), stomach cancer, supratentorial primitive neuroectodermal tumors, T-cell lymphoma, testicular cancer, throat cancer, thymoma and thymic carcinoma, thyroid cancer, transitional cell cancer, urethral cancer, uterine sarcoma, vaginal cancer, visual pathway and hypothalamic glioma, vulvar cancer, Waldenstorm's macroglobulinemia, Wilms tumor, and systemic and central metastases of any of the foregoing.

Methods provided by the present disclosure include methods of treating cancer, where the cancer is selected from breast cancer and melanoma.

Methods provided by the present disclosure include methods of treating an inflammatory disease in a patient comprising administering to a patient in need thereof a therapeutically effective amount of a compound or pharmaceutical composition provided by the present disclosure.

Examples of inflammatory diseases include allergy, Alzheimer's disease, anemia, ankylosing spondylitis, arthritis, atherosclerosis, asthma, autism, arthritis, carpal tunnel syndrome, celiac disease, colitis, Crohn's disease, congestive heart failure, dermatitis, diabetes, diverticulitis, eczema, fibromyalgia, fibrosis, gall bladder disease gastroesophageal reflux disease, Hashimoto's thyroiditis, heart attack, hepatitis, irritable bowel syndrome, kidney failure, lupus, multiple sclerosis, nephritis, neuropathy, pancreatitis, Parkinson's disease, psoriasis, polymyalgia rheumatica, rheumatoid arthritis, scleroderma, stroke, surgical complications, and ulcerative colitis.

Methods provided by the present disclosure include methods of treating an inflammatory disease in a patient, where the inflammatory disease is selected from, for example, acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes, and rheumatoid arthritis.

Methods provided by the present disclosure include methods of treating an autoimmune disease in a patient comprising administering to a patient in need thereof a therapeutically effective amount of a compound or pharmaceutical composition provided by the present disclosure.

A compound or a pharmaceutical composition provided by the present disclosure can be useful in treating autoimmune diseases. Autoimmune diseases can be defined as human diseases in which the immune system attacks its own proteins, cells, and/or tissues. A comprehensive listing and review of autoimmune diseases can be found, for example, in *The Autoimmune Diseases*, Rose and Mackay, 2014, Academic Press.

Examples of autoimmune diseases include Addison's disease, agammaglobulinemia, alopecia areata, amyloidosis, ankylosing spondylitis, anti-GBM/anti-TBN nephritis, antiphospholipid syndrome, autoimmune angioedema, autoimmune dysautonomia, autoimmune encephalomyelitis, autoimmune hepatitis, autoimmune inner ear disease, autoimmune myocarditis, autoimmune pancreatitis, autoimmune retinopathy, autoimmune urticaria, axonal and neuronal neuropathy, Balo disease, Bechet's disease, benign mucosal pemphigoid, bullous pemphigoid, Castleman disease, celiac disease, Chagas disease, chronic inflammatory demyelinating polyneuropathy, chronic recurrent multifocal osteomyelitis, Churg-Strauss, cicatricial pemphigoid, Cogan' syndrome, cold agglutinin disease, congenital heart block, Coxsackie myocarditits, CREST syndrome, Crohn's disease, dermatitis herpetiformis, dermatomyositis, Devic's disease, discoid lupus, Dressler's syndrome, endometriosis, eosinophilic esophagitis, eosinophilic fasciitis, erythema nodosum, essential mixed cryoglobulinemia, Evans syndrome, fibromyalgia, fibrosing alveolitis, giant cell arteritis, giant cell myocarditis, glomerulonephritis, Goodpasture's syndrome, granulomatosis with polyangiitis, Graves' disease, Guillain-Barre syndrome, Hashimoto's thyroiditis, hemolytic anemia, Henoch-Schonlein purpura, herpes gestationis or pemphigoid gestationis, hypogammaglobulinemia, IgA nephropathy, IgG4-related sclerosing disease, immune thrombocytopenic purpura, inclusion body myositis, interstitial cystitis, juvenile arthritis, juvenile diabetes, juvenile myositis, Kawasaki disease, Lambert-Eaton syndrome, leukocytoclastic vasculitis, lichen planus, lichen sclerosis, ligneous conjunctivitis, linear IgA disease, lupus, Lyme disease chronic, Meniere's diseases, microscopic polyangiitis, mixed connective tissue disease, Mooren's ulcer, Mucha-Habermann disease, multiple sclerosis, myasthenia gravis, myositis, narcolepsy, neuromyelitis, optica, neutropenia, ocular cicatricial pemphigoid, optic neuritis, palindromic rheumatism, PANDAS, paraneoplastic cerebellar degeneration, paroxysmal nocturnal hemoglobinuria, Parry Romberg syndrome, pars planitis, Parsonage-Turner syndrome, pemphigus, peripheral neuropathy, perivenous encephalomyelitis, pernicious anemia, POEMS syndrome, polyarteritis nodosa, polyglandular syndromes, polymyalgia rheumatica, polymyositis, post-myocardial infarction syndrome, post-pericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, Takayasu's arteritis, temporal arteritis, thrombocytopenic purpura, Tolosa-Hunt syndrome, transverse myelitis, type 1 diabetes, ulcerative colitis, undifferentiated connective tissue disease, uveitis, vaculitis, vitiligo, and Wegener's granulomatosis.

A compound or a pharmaceutical composition provided by the present disclosure can be used to treat autoimmune disorders such as, for example, lupus, graft-versus-host disease, hepatitis C-induced vasculitis, Type I diabetes, multiple sclerosis, spontaneous loss of pregnancy, atopic diseases, and inflammatory bowel diseases.

A compound or a pharmaceutical composition provided by the present disclosure can be administered with one or more additional therapeutic agents for treating an autoimmune disease. A compound of Formula (1) or a pharmaceutical composition thereof may be administered in conjunction with one or more immunosuppressants including, for example, corticosteroids such as prednisone, budesonide, and prednisolone; Janus kinase inhibitors such as tofacitinib; calcineurin inhibitors such as cyclosporine and tacrolimus; mTOR inhibitors such as sirolimus and everolimus; IMDH inhibitors such as azathioprine, leflunomide, and mycophenolate; biologics such as abatacept adalimumab, anakinra, certolizumab, etanercept, golimumab, infliximab, ixekizumab, natalizumab, rituximab, secukinumab, tocilizumab, ustekinumab, and vedolizumab; and monoclonal antibodies such as basiliximab and daclizumab.

Methods provided by the present disclosure include methods of treating a disease in a patient comprising administering to a patient in need thereof a therapeutically effective amount of a compound or pharmaceutical composition provided by the present disclosure, wherein the disease is selected from acute coronary syndrome, acute lung injury, acute respiratory distress syndrome (ARDS), Alzheimer's disease, asthma, a cardiovascular disease, chronic obstructive pulmonary disease (COPD), inflammatory bowel disease, major depressive disorder, multiple sclerosis, neuropathic pain, and rheumatoid arthritis.

Methods provided by the present disclosure include methods of treating a disease in a patient comprising administering to a patient in need thereof a therapeutically effective amount of a compound or pharmaceutical composition provided by the present disclosure, wherein the disease is an age-related disease such as, for example, hearing loss, muscle degeneration, Werner's syndrome, cellular aging, or Alzheimer's disease.

Methods provided by the present disclosure include methods of treating a disease in a patient comprising administering to a patient in need thereof a therapeutically effective amount of a compound or pharmaceutical composition provided by the present disclosure, wherein the disease is selected from sudden idiopathic hearing loss, drug induced hearing loss, age-related hearing loss, and Duchenne muscular dystrophy.

A compound of Formula (1) or a pharmaceutical composition thereof may be administered to a patient to treat a viral disease.

Examples of suitable viral diseases include *Acinetobacter* infections, actinomycosis, African sleeping sickness (African trypanosomiasis), AIDS (acquired immunodeficiency syndrome), amoebiasis, anaplasmosis, angiostrongyliasis, anisakiasis, anthrax, *Arcanobacterium haemolyticum* infection, Argentine hemorrhagic fever, ascariasis, aspergillosis, astrovirus infection, babesiosis, *Bacillus cereus* infection, bacterial meningitis, bacterial pneumonia, bacterial vaginosis, *Bacteroides* infection, balantidiasis, bartonellosis, *Baylisascaris* infection, Bejel, syphilis, yaws, BK virus infection, black piedra, blastocystosis, blastomycosis, Bolivian hemorrhagic fever, botulism (and Infant botulism), Brazilian hemorrhagic fever, brucellosis, bubonic plague, *Burkholderia* infection, buruli ulcer, calicivirus infection (Norovirus and Sapovirus), campylobacteriosis, candidiasis (Moniliasis; Thrush), capillariasis, carrion's disease, cat-scratch disease, cellulitis, Chagas disease (American trypanosomiasis), chancroid, chickenpox, chikungunya, chlamydia, *Chlamydophila pneumoniae* infection (Taiwan acute respiratory agent or TWAR), cholera, chromoblastomycosis, Chytridiomycosis, clonorchiasis, *Clostridium difficile* colitis, coccidioidomycosis, Colorado tick fever (CTF), common cold (acute viral rhinopharyngitis; Acute coryza), a coronavirus infection such as a MERS-CoV infection, a SARS-CoV infection, or a SARS-CoV-2 infection. Coronavirus disease 2019 (COVID-19), pneumonia associated with a coronavirus infection, a Human Respiratory Syndical infection, Creutzfeldt-Jakob disease (CJD), Crimean-Congo hemorrhagic fever (CCHF), cryptococcosis, cryptosporidiosis, cutaneous larva migrans (CLM), cyclosporiasis, cysticercosis, cytomegalovirus infection, Dengue fever, desmodesmus infection, dientamoebiasis, diphtheria, diphyllobothriasis, dracunculiasis, Ebola hemorrhagic fever, echinococcosis, Ehrlichiosis, enterobiasis (pinworm infection), *Enterococcus* infection, enterovirus infection, epidemic typhus, Epstein-Barr virus infectious mononucleosis (Mono), erythema infectiosum (Fifth disease), fxanthem subitum (Sixth disease), fasciolosis, fasciolopsiasis, fatal familial insomnia (FFI), filariasis, food poisoning by *Clostridium perfringens*, free-living amebic infection, *Fusobacterium* infection, gas gangrene (Clostridial myonecrosis), geotrichosis, Gerstmann-Straussler-Scheinker syndrome (GSS), giardiasis, glanders, gnathostomiasis, gonorrhea, granuloma inguinale (Donovanosis), Group A streptococcal infection, Group B streptococcal infection, *Haemophilus influenzae* infection, hand, foot and mouth disease (HFMD), Hantavirus Pulmonary Syndrome (HPS), Heartland virus disease, *Helicobacter pylori* infection, hemolytic-uremic syndrome (HUS), hemorrhagic fever with renal syndrome (HFRS), Hendra virus infection, Hepatitis A, Hepatitis B, Hepatitis C, Hepatitis D, Hepatitis E, *Herpes* simplex, histoplasmosis, hookworm infection, human bocavirus infection, human *Ewingii ehrlichiosis*, human granulocytic anaplasmosis (HGA), human metapneumovirus infection, human monocytic ehrlichiosis, human papillomavirus (HPV) infection, human parainfluenza virus infection, hymenolepiasis, influenza (flu), isosporiasis, Kawasaki disease, keratitis, Kingella kingae infection, Kuru, Lassa fever, Legionellosis (Legionnaires' disease), leishmaniasis, leprosy, leptospirosis, listeriosis, Lyme disease (Lyme borreliosis), lymphatic filariasis (elephantiasis), lymphocytic choriomeningitis, malaria, Marburg hemorrhagic fever (MHF), measles, melioidosis (Whitmore's disease), meningitis, meningococcal disease, metagonimiasis, microsporidiosis, Middle East respiratory syndrome (MERS), molluscum contagiosum (MC), monkeypox, mumps, murine typhus (Endemic typhus), mycetoma, *Mycoplasma genitalium* infection, *Mycoplasma* pneumonia, myiasis, neonatal conjunctivitis (Ophthalmia neonatorum), Nipah virus infection, nocardiosis, Norovirus (children and babies), onchocerciasis (River blindness), opisthorchiasis, paracoccidioidomycosis (South American blastomycosis), paragonimiasis, pasteurellosis, pediculosis capitis (Head lice), pediculosis corporis (Body lice), pediculosis pubis (pubic lice, crab lice), pelvic inflammatory disease (PID), pertussis (whooping cough), plague, pneumococcal infection, *Pneumocystis* pneumonia (PCP), pneumonia, poliomyelitis, Pontiac fever, *Prevotella* infection, primary amoebic meningoencephalitis (PAM), progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley fever (RVF), Rocky Mountain spotted fever (RMSF), rotavirus infection, rubella, *Salmonellosis*, SARS (severe acute respiratory syndrome), MERS-CoV, SARS-CoV, SARS-CoV-2, scabies, scarlet fever, schistosomiasis, sepsis, shigellosis (bacillary dysentery), shingles (Herpes zoster), smallpox (variola), sporotrichosis, staphylococcal food poisoning, staphylococcal infection, strongyloidiasis, subacute sclerosing panencephalitis, taeniasis, tetanus (lockjaw), tinea barbae (barber's itch), tinea capitis (ringworm of the scalp), tinea corporis (ringworm of the body), tinea cruris (Jock itch), tinea manum (ringworm of the hand), tinea nigra, tinea pedis (athlete's foot), tinea unguium (onychomycosis), tinea *versicolor* (*Pityriasis versicolor*), toxocariasis (ocular larva migrans (OLM)), toxocariasis (visceral larva migrans (VLM)), toxoplasmosis, trachoma, trichinosis, trichomoniasis, trichuriasis (whipworm infection), tuberculosis, tularemia, typhoid fever, typhus fever, *Ureaplasma urealyticum* infection, valley fever, Venezuelan equine encephalitis, Venezuelan hemorrhagic fever, *Vibrio parahaemolyticus* enteritis, *Vibrio vulnificus* infection, viral pneumonia, West Nile fever, white *Piedra* (tinea blanca), yellow fever, *Yersinia pseudotuberculosis* infection, yersiniosis, zeaspora, Zika fever, and zygomycosis.

The amount of a compound of Formula (1) provided by the present disclosure, or pharmaceutical composition thereof that will be effective in the treatment of a cancer can depend, at least in part, on the nature of the disease, and may be determined by standard clinical techniques known in the art. In addition, in vitro or in vivo assays may be employed to help identify optimal dosing ranges. Dosing regimens and dosing intervals may also be determined by methods known to those skilled in the art. The amount of a compound of Formula (1) provided by the present disclosure administered may depend on, among other factors, the patient being treated, the weight of the patient, the severity of the disease, the route of administration, and the judgment of the prescribing physician.

For systemic administration, a therapeutically effective dose may be estimated initially from in vitro assays. Initial doses may also be estimated from in vivo data, e.g., animal models, using techniques that are known in the art. Such information may be used to more accurately determine useful doses in humans. One having ordinary skill in the art may optimize administration to humans based on animal data.

A dose of a compound of Formula (1) provided by the present disclosure and appropriate dosing intervals may be selected to maintain a sustained therapeutically effective concentration of a compound of Formula (1) provided by the present disclosure in the blood of a patient, and in certain embodiments, without exceeding a minimum adverse concentration.

A pharmaceutical composition comprising a compound of Formula (1) provided by the present disclosure may be administered, for example once per week, every 2 weeks, every 3 weeks, every 4 weeks, every 5 weeks, or every 6 weeks. Dosing may be provided alone or in combination with other drugs and may continue as long as required for effective treatment of the disease. Dosing may also be undertaken using continuous or semi-continuous administration over a period of time. Dosing includes administering a pharmaceutical composition to a mammal, such as a human, in a fed or fasted state.

A pharmaceutical composition may be administered in a single dosage form or in multiple dosage forms or as a continuous or an accumulated dose over a period of time. When multiple dosage forms are used the amount of a compound of Formula (1) provided by the present disclosure contained within each of the multiple dosage forms may be the same or different.

Suitable daily dosage ranges for administration can range, for example, from about 2 µg to about 200 mg of a compound of Formula (1) provided by the present disclosure per kilogram body weight.

Suitable daily dosage ranges for administration may range, for example, from about 1 µg to about 50 mg of a compound of Formula (1) provided by the present disclosure per square meter ($m^2$) of body surface.

A compound of Formula (1) provided by the present disclosure may be administered to treat cancer in a patient in an amount, for example, from 0.001 mg/day to 100 mg/day, or in any other appropriate daily dose. A dose can be, for example, from 0.01 µg/kg body weight/week to 100 µg/kg body weight/week or any other suitable dose.

A pharmaceutical composition comprising a compound of Formula (1) provided by the present disclosure may be administered to treat cancer in a patient so as to provide a therapeutically effective concentration of a compound of Formula (1) provided by the present disclosure in the blood or plasma of the patient. A therapeutically effective concentration of a compound of a compound of Formula (1) provided by the present disclosure in the blood of a patient can be, for example, from 0.01 µg/L to 1,000 g/L, from 0.1 µg/L to 500 µg/L, from 1 µg/L to 250 µg/L, or from about 10 µg/L to about 100 µg/L. A therapeutically effective concentration of a compound of Formula (1) provided by the present disclosure in the blood of a patient can be, for example, at least 0.01 µg/L, at least 0.1 µg/L, at least 1 µg/L, at least about 10 µg/L, or at least 100 µg/L. A therapeutically effective concentration of a compound of Formula (1) in the blood of a patient can be, for example, less than an amount that causes unacceptable adverse effects including adverse effects to homeostasis. A therapeutically effective concentration of a compound of Formula (1) in the blood of a patient can be an amount sufficient to restore and/or maintain homeostasis in the patient.

Pharmaceutical compositions provided by the present disclosure may be administered to treat a disease in a patient so as to provide a therapeutically effective concentration of a compound of Formula (1) in the blood of a patient for a period of time such as, for example, for 4 hours, 8 hours, 12 hours, 16 hours, 20 hours, 1 day, or 2 days.

The amount of a compound of Formula (1) administered may vary during a treatment regimen.

Pharmaceutical compositions provided by the present disclosure may further comprise one or more pharmaceutically active compounds in addition to a compound of Formula (1). Such compounds may be provided, for example, to treat the cancer being treated with the compound of Formula (1) or to treat a disease, disorder, or condition other than the cancer being treated with the compound of Formula (1), to treat a side-effect caused by administering the compound of Formula (1), to augment the efficacy of the compound of Formula (1), and/or to modulate the activity of the compound of Formula (1).

A compound of Formula (1) provided by the present disclosure may be administered in combination with at least one other therapeutic agent. A compound of Formula (1) may be administered to a patient together with another compound for treating cancer in the patient. The at least one other therapeutic agent can be a second, different compound of Formula (1). A compound of Formula (1) and the at least one other therapeutic agent may act additively or, and in certain embodiments, synergistically with another compound of Formula (1). The at least one additional therapeutic agent may be included in the same pharmaceutical composition or vehicle comprising the compound of Formula (1) or may be in a separate pharmaceutical composition or vehicle. Accordingly, methods provided by the present disclosure further include, in addition to administering a compound of Formula (1), administering one or more therapeutic agents effective for treating cancer or a different disease, disorder or condition than cancer. Methods provided by the present disclosure include administration of a compound of Formula (1) and one or more other therapeutic agents provided that the combined administration does not inhibit the therapeutic efficacy of the compound of Formula (1) and/or does not produce adverse combination effects.

A pharmaceutical composition comprising a compound of Formula (1) may be administered concurrently with the administration of another therapeutic agent, which may be part of the same pharmaceutical composition as, or in a different pharmaceutical composition than that comprising a compound of Formula (1). A compound of Formula (1) may be administered prior or subsequent to administration of another therapeutic agent. In certain combination therapies, the combination therapy may comprise alternating between administering a compound of Formula (1) and a composition comprising another therapeutic agent, e.g., to minimize adverse drug effects associated with a particular drug. When a compound of Formula (1) is administered concurrently with another therapeutic agent that potentially may produce an adverse drug effect including, for example, toxicity, the other therapeutic agent may be administered at a dose that falls below the threshold at which the adverse drug reaction is elicited.

A pharmaceutical composition comprising a compound of Formula (1) provided by the present disclosure may be administered with one or more substances, for example, to enhance, modulate and/or control release, bioavailability, therapeutic efficacy, therapeutic potency, and/or stability, of the compound of Formula (1). For example, a pharmaceutical composition comprising a compound of Formula (1) can be co-administered with an active agent having pharmacological effects that enhance the therapeutic efficacy of the compound of Formula (1).

A compound of Formula (1), or a pharmaceutical composition thereof may be administered in conjunction with an agent known or believed to be effective in treating a disease such as cancer, an autoimmune disease or an inflammatory disease in a patient, such as the same disease being treated with the compound of Formula (1).

A compound of Formula (1), or a pharmaceutical composition thereof may be administered in conjunction with an agent known or believed to interfere with cell proliferation.

A compound of Formula (1), or a pharmaceutical composition thereof may be administered in conjunction with an agent known or believed to interfere with cellular metabolism, to be an anti-metabolite, to interfere with RNA transcription, to interfere with RNA translation, to interfere with cellular protein synthesis, to interfere with synthesis of precursors for DNA synthesis and replication, to interfere with purine synthesis, to interfere with nucleoside synthesis, to interact with mTOR, to be an mTOR inhibitor, to interfere with cell cycle checkpoints.

A compound of Formula (1) or a pharmaceutical composition thereof may be administered in conjunction with a checkpoint inhibitor including a CTLA-4 inhibitor such as ipilimumab, a PD-1 inhibitor such as pembrolizumab and nivolumab, and/or a PD-LI inhibitor such as atezolizumab, avelumab, and durvalumab. A compound of Formula (1) or a pharmaceutical composition thereof may be administered in conjunction with an immunomodulator such as CD137/ 4-1BB, CD27, GIYR, and/or OC40.

A compound of Formula (1) or a pharmaceutical composition thereof may be administered in conjunction with an agent known or believed to be cytotoxic, to cause DNA damage, to cause cell cycle arrest, or to cause mitotic catastrophe.

A compound of Formula (1) or a pharmaceutical composition thereof may be administered in conjunction with an agent known or believed to modulate glutathione concentration, to modulate glutathione concentration within cells, to decrease glutathione concentration within cells, to reduce glutathione uptake into cells, to reduce glutathione synthesis, or to reduce glutathione synthesis within cells.

A compound of Formula (1) or a pharmaceutical composition thereof may be administered in conjunction with an agent known or believed to interfere with neovascularization, to reduce neovascularization, or to promote neovascularization.

A compound of Formula (1) or a pharmaceutical composition thereof may be administered in conjunction with an agent known or believed to interfere with hormone homeostasis, to interfere with hormone synthesis, to interfere with hormone receptor binding, or to interfere with hormone signal transduction.

A compound of Formula (1) or a pharmaceutical composition thereof may be administered in conjunction with an agent known or believed to interfere with growth factor homeostasis, to interfere with growth factor receptor expression, to interfere with growth factor binding to growth factor receptors, to interfere with growth factor receptor signal transduction, to interfere with the Hedgehog (Hh) signaling, to inhibit the Hedgehog pathway signaling, to inhibit ALK (anaplastic lymphoma kinase) pathway signaling, or to inhibit the non-homologous end joining (NHEJ) pathway.

A compound of Formula (1) or a pharmaceutical composition thereof may be administered in conjunction with one or more agents known or believed to be a VEGFR (vascular endothelial growth factor receptor) inhibitor, a RTK (receptor tyrosine kinase) inhibitor, a sodium channel current blocker, aFAK (focal adhesion kinase) inhibitor, a GLI (glioma-associated oncogene) inhibitor, a GLI1 inhibitor, a GLI2 inhibitor, a GLI3 inhibitor, a MAPK (mitogen-activated protein kinase) inhibitor, a MAPK/ERK pathway (also known as Ras-Raf-MEK-ERK pathways) inhibitor, a MEK1 inhibitor, a MEK2 inhibitor, a MEK5 inhibitor, a MEK5/ ERK5 inhibitor, aRTA (renal tubular acidosis) inhibitor, a ALK (anaplastic lymphoma kinase) inhibitor, Aa LK kinase inhibitor, a nuclear translocation inhibitor, a PORCN (porcupine) inhibitor, a 5-ARI (5α-reductase inhibitor), topoisomerase inhibitor, a Ras (rat sarcoma) inhibitor, a K-ras inhibitor, a CERK (ceramide kinase) inhibitor, a PKB (protein kinase B, also known as AKT) inhibitor, a AKT1 inhibitor, EZH2 (enhancer of zeste homolog 2) inhibitor, a BET (bromodomain and extraterminal domain motif) inhibitor, a SYK (spleen tyrosine kinase) inhibitor, JAK (janus kinase) inhibitors, a SYK/JAK inhibitor, a IDO (indoleamine-pyrrole 2,3-dioxygenase) inhibitor, a IDO1 inhibitor, a RXR (retinoic X receptors) activating agent, a selective RXR activating agent, a p-glycoprotein inhibitor, a ERK inhibitor, a PI3K (phosphatidylinositol-4,5-bisphosphate 3-kinase) inhibitor, a BRD (bromodomain-containing protein) inhibitor, a BRD2 inhibitor, a BRD3 inhibitor, a BRD4 inhibitor, a BRDT (bromodomain testis-specific protein) inhibitor, a reverse transcriptase inhibitor, a NRT (nucleoside analog reverse-transcriptase) inhibitor, a PIM (proviral integrations of moloney virus) inhibitor, a EGFR (epidermal growth factor receptor) inhibitor, a photosensitizer, a radiosensitizer, a ROS (proto-oncogene, receptor tyrosine kinase) inhibitor, a ROS1 (proto-oncogene 1) inhibitor, a CK (casein kinase) inhibitor, a CK2 inhibitor, a Bcr-Abl (breakpoint cluster region—Abelson proto-oncogene) tyrosine-kinase inhibitor such as dasatinib, a microtubule stabilizing agent, a microtubule depolymerization/disassembly inhibitor, a DNA intercalator, an androgen receptor antagonist, a chemoprotective agents, a HDAC (histone deacetylase) inhibitor, a DPP (dipeptidyl peptidase) inhibitor, a DPP-4 inhibitor, BTK (Bruton's tyrosine kinase) inhibitor, a kinase inhibitor such as imatinib, a tyrosine kinase inhibitor such as nilotinib, a ARP (poly (ADP-ribose) polymerase) inhibitor, a CDK (cyclin-dependent kinase) inhibitor, a CDK4 inhibitor, a CDK6 inhibitor, a CDK4/6 inhibitor, a HIF1α (hypoxia-inducible factor 1-α) inhibitor, a DNA ligase inhibitor, a DNA ligase IV inhibitor, a NHEJ (non-homologous end joining) inhibitor, a DNA ligase IV, a NHEJ inhibitor and a RAF inhibitor, a TKI and a RAF inhibitor, a TKI and RAF inhibitor such as sorafenib, a PDT (photodynamic therapy) sensitizer, an ATR (ataxia telangiectasia- and Rad3-related protein kinase) inhibitor, or a combination of any of the foregoing.

A compound of Formula (1) or a pharmaceutical composition thereof may be administered in conjunction with one or more chemotherapeutic agents, such as, for example, a VEGFR inhibitor such as fruquintinib, motesanib/AMG-706, vatalanib; a RTK inhibitor such as ponatinib; a sodium channel blocker such as GS967; a FAK inhibitor such as TAE226; a GLI1 and GLI2 inhibitor such as GANT61, a MEK inhibitor such as binimetinib; a RTA inhibitor such as linifanib; an ALK inhibitor such as brigstinib; bromopyruvic acid; a DNA alkylating agent such as thiotepa; nuclear translocations factors such as JSH-23; a PORCn inhibitor such as Wnt-C59; a 5α-reductase inhibitor such as dutasteride; a topoisomerase inhibitor such as carubicin; a RAS inhibitor such as Kobe0065; a CerK inhibitor such as NVP-231; an AKT inhibitor such as uprosertib; a EZH2 inhibitor such as GSK-503; a BET bromodomain inhibitor such as OTX015; a MEK5/ERK5 inhibitor such as BIX02189; a Syl/JAK inhibitor such as cerdulatinib; an IDO1 inhibitor such as NLG919; a retinoic X receptor activating agent such as bexsrotene; a PGP inhibitor such as acotiamide or actotiamide HCl; an Erk inhibitor such SCH772984; a PI3K inhibitor such as gedatolisib; a JAK inhibitor such as ruxolitinib; an AKT inhibitor such as afuresertib or afuresertib HCl; an ALK1 inhibitor such as ceritinib; an HDAC inhibitor such as abexinostat; a DPP inhibitor such as oamarigliptin; an EGFR inhibitor such as gefittinib; an EZH2 inhibitor such as GSK126; a BTK inhibitor such as ibrutinib; a kinase inhibitor such as imatinin HCl; an IDO inhibitor such as INCB024360; a DNA crosslinker such as mitomycin C; a tyrosine kinase inhibitor such as nilotinib, a PARP inhibitor such as olaparib; a tubulin stabilization promoter such as paclitaxel; a CDK4/6 inhibitor such as palbociclib; a RTK inhibitor such as sunitinib; a PDT sensitizer such as tslsporfin; a p-glycoprotein inhibitor such as tariquidar; an ATR inhibitor such as VE-822; an HDAC inhibitor such as PCI-24781; a DPP inhibitor such as omarigliptin; an EGFR inhibitor such as gefinib; an EZH2 inhibitor such as GSK126; a BTK inhibitor such as irbrutinib; an IDO inhibitor such as INCB024360; or a combination of any of the foregoing.

A compound of Formula (1) or a pharmaceutical composition thereof may be administered in conjunction with another chemotherapeutic agent, such as, for example, N-acetyl cysteine (NAC), adriamycin, alemtuzumab, amifostine, arsenic trioxide, ascorbic acid, bendamustine, bevacizumab, bortezomib, busulfan, buthionine sulfoxime, carfilzomib, carmustine, clofarabine, cyclophosphamide, cyclosporine, cytarabine, dasatinib, datinomycin, defibrotide, dexamethasone, docetaxel, doxorubicin, etoposide, filgrastim, floxuridine, fludarabine, gemcitabine, interferon alpha, ipilimumab, lenalidomide, leucovorin, melphalan, mycofenolate mofetil, paclitaxel, palifermin, panobinostat, pegfilrastim, prednisolone, prednisone, revlimid, rituximab, sirolimus, sodium 2-mercaptoethane sulfonate (MESNA), sodium thiosulfate, tacrolimus, temozolomide, thalidomide, thioguanine, thiotepa, topotecan, velcade, or a combination of any of the foregoing.

A compound of Formula (1) or a pharmaceutical compositions thereof can be used in combination therapy with other chemotherapeutic agents including one or more antimetabolites such as folic acid analogs; pyrimidine analogs such as fluorouracil, floxuridine, and cytosine arabinoside; purine analogs such as mercaptopurine, thiogunaine, and pentostatin; natural products such as vinblastine, vincristine, etoposide, tertiposide, dactinomycin, daunorubicin, doxorubicin, bleomycin, mithamycin, mitomycin C, L-asparaginase, and interferon alpha; platinum coordination complexes such as cis-platinum, and carboplatin; mitoxantrone; hydroxyurea; procarbazine; hormones and antagonists such as prednisone, hydroxyprogesterone caproate, medroxyprogesterone acetate, megestrol acetate, diethylstilbestrol, ethinyl estradiol, tamoxifen, testosterone propionate, fluoxymesterone, flutamide, and leuprolide, anti-angiogenesis agents or inhibitors such as angiostatin, retinoic acids, paclitaxel, estradiol derivatives, and thiazolopyrimidine derivatives; apoptosis prevention agents; triptolide; colchicine; luliconazole; and radiation therapy.

A compound of Formula (1) or a pharmaceutical composition thereof may be co-administered with a compound that inhibits DNA repair such as, for example, O6-benzylguanine (O6-BG).

A compound of Formula (1) or a pharmaceutical composition thereof may be administered in conjunction with one or more chemotherapeutic agents such as, for example, abarelix, abemaciclib, abiraterone, abiraterone acetate, ABVD, ABVE, AC, acalabrutinib, aclarubicin hydrochloride, AC-T, ADE, adenine, ado-trastuzumab emtansine, adriamycin, afatinib, aldesleukin, alectinib, alemtuzumab, alendronate sodium, alitretinoin, allopurinol sodium, alpelisib, altretamine, amifostine, aminoglutethimide, aminolevulinic acid, amrubicin, amsacrine, anastrozole, zoledronic acid. Angiostatin, apalutamide, apremilast, aprepitant, arsenic trioxide, ascorbic acid, asparaginase *Erwinia chrysanthemi*, atezolizumab, avelumab, axicabtagene ciloleucel, axitinib, azacitidine, azathioprine sodium, bazedoxifene (serm), BEACOPP, belinostat, bendamustine hydrochloride, BEP, bevacizumab, bexarotene, bicalutamide, binimetinib, biricodar, bleomycin sulfate, blinatumomab, bortezomib, bosutinib, brentuximab vedotin, brigatinib, brivudine, BuMel, Buserelin, busulfan, buthionine sulfoxime, cabazitaxel, cabozantinib, CAF, calaspargase pegol-mknl, capecitabine, caplacizumab-yhdp, CAPOX, carboplatin, carboquone, carfilzomib, carmofur, carmustine, CEM, cemiplimab-rwlc, ceritinib, cetuximab, CEV, Chlorambucil, Cisplatin, cladribine, clodronate disodium, clofarabine, CMF, cobimetinib, copanlisib hydrochloride, COPDAC, COPP, Crizotinib, CVP, Cyclophosphamide, cyclosporine, cytarabine, cytosine arabinoside, dabrafenib, dacarbazine, dacomitinib, dactinomycin, daratumumab, darbepoetin a, dasatinib, datinomycin, daunorubicin, decitabine, defribrotide, degarelix, denileukin diftitox, denosumab, dexamethasone, dexrazoxane hydrochloride, diaziquone, diethyl stilbestrol, dinutuximab, docetaxel, doxifluridine, doxorubicin, dromostanolone propionate, durvalumab, dutasteride, duvelisib, elotuzumab, eltrombopag, emapalumab-lzsg, enasidenib mesylate, encorafenib, enzalutamide, epirubicin hydrochloride, EPOCH, epoetin a, erdafitinib, eribulin mesylate, erlotinib hydrochloride, estramustine phosphate sodium, ethinyl estradiol, etoposide, everolimus, exemestane, fee, fentanyl, filgrastim, fingolimod, floxuridine, fludarabine phosphate, fluorouracil, fluoxymesterone, flutamide, folfiri, folfirinox, folfox, formestane, formylmelphalan, fosaprepitant, fostamatinib disodium, fotemustine, FU-LV, fulvestrant, gefitinib, gemcitabine, gemtuzumab ozogamicin, gilteritinib fumarate, glasdegib maleate, glucarpidase, glutathione, glyciphosphoramide, glyfosfin, goserelin acetate, granisetron, heptaplatin, hexyl 5-aminolevulinate, histrelin acetate, HPV bivalent vaccine, hydroxyprogesterone caproate, hydroxyurea, hyper-CVAD, ibandronate sodium, ibrutinib, ICE, Icotinib, idarubicin hydrochloride, idelalisib, idoxuridine, ifosfamide, imatinib mesylate, imiquimod, ingenol mebutate, inotuzumab ozogamicin, interferon alpha, iobenguane, ipilimumab, irinotecan hydrochloride, ivosidenib, ixabepilone, ixazomib citrate, JEB, lanreotide acetate, lapatinib, larotrectinib sulfate, lasofoxifene, 1-asparaginase, lenalidomide, lenvatinib mesylate, letrozole, leucovorin calcium, leuprolide acetate, levamisole hydrochloride, levoleucovorin calcium, lobaplatin, lomustine, lorlatinib, lutetium Lu 177-dotatate, maropitant, masoprocol, mechlorethamine hydrochloride, medroxyprogesterone acetate, megestrol acetate, melphalan, mercaptoethane sulfonate sodium, mercaptopurine, mesna, methotrexate, methoxsalen, methyl aminolevulinate, methylene blue, methylisoindigotin, methylnaltrexone bromide, midostaurin, mifamurtide, miltefosine, miriplatin, mithamycin, mitobronitol, mitomycin C, mitotane, mitoxantrone hydrochloride, mogamulizumab-kpkc, moxetumomab pasudotox-tdfk, MVAC, mycophenolate mofetil, nabiximols, n-acetyl cysteine, nafarelin, nandrolone, necitumumab, nedaplatin, nelarabine, neratinib maleate, netupitant, nilotinib, nilutamide, nimustine, nintedanib, niraparib tosylate monohydrate, nivolumab, nocodazole, O6-benzylguanine, obinutuzumab, octreotide, OEPA, ofatumumab, OFF, Olaparib, olaratumab, omacetaxine mepesuccinate, ondansetron hydrochloride, OPPA, osimertinib mesylate, oxaliplatin, paclitaxel, PAD, Palbociclib, palifermin, palonosetron hydrochloride, pamidronate disodium, panitumumab, panobinostat, pasireotide, pazopanib hydrochloride, PCV, PEB, pegaspargase, pegfilrastim, peginterferon α-2b, pembrolizumab, pemetrexed disodium, pentostatin, peplomycin, pertuzumab, pipobroman, pirarubicin, plerixafor, plicamycin, polatuzumab vedotin-piiq, pomalidomide, ponatinib, ponatinib hydrochloride, porfimer sodium, porfiromycin, pralatrexate, prednimustine, prednisolone, prednisone, procarbazine hydrochloride, propranolol hydrochloride, quinagolide hydrochloride, radium 223 dichloride, radotinib, raloxifene, raloxifene hydrochloride, raltitrexed, ramucirumab, ranimustine, rasburicase, ravulizumab-cwvz, R-CHOP, R-CVP, recombinant HPV bivalent vaccine, regorafenib, R-EPOCH, retinoic acids, revlimide, ribociclib, R-ICE, rituximab, rolapitant hydrochloride, romidepsin, romiplostim, rucaparib camsylate, ruxolitinib, semustine, siltuximab, sipuleucel-t, sirolimus, sodium thiosulfate, sonidegib, sorafenib free, STANFORD V, Streptozocin, sufentanil, sunitinib, TAC, Tacrolimus, tagraxofusp-erzs, talaporfin sodium, talazoparib tosylate, talc, talimogene, aherparepvec, tamibarotene, tamoxifen, citrate, tapentadol, temoporfin, temozolomide, temsirolimus, teniposide, teriflunomide, tertiposide, testolactone, testosterone propionate, thalidomide, thioguanine, thiotepa, thymalfasin, tisagenlecleucel, toceranib phosphate, tocilizumab, topotecan, hydrochloride, toremifene, TPF, trabectedin, trametinib, trastuzumab, trastuzumab, tretinoin, trifluridine, ipiracil, ydrochloride, trilostane, triptorelin, tropisetron, uramustine, uridine, riacetate, VAC, valrubicin, VAMP, vandetanib, vedotin, VeIP, vemurafenib, venetoclax, verteporfin, vinblastine, vincristine, vindesine, vinorelbine tartrate, vip, vismodegib, vorinostat, vorinostat, XELIRI, XELOX, Ziv-aflibercept, zoledronic acid, or a combination of any of the foregoing.

The efficacy of administering a compound of Formula (1) or a pharmaceutical composition thereof for treating cancer, an inflammatory disease, or an autoimmune disease may be assessed using in vitro and animal studies and in clinical trials.

Methods of inhibiting p38α MAPK provided by the present disclosure include contacting p38α MAPK with a compound provided by the present disclosure to a pocket near the ED substrate-docking site of p38α MAPK.

Methods of inhibiting p38α MAPK provided by the present disclosure do not result in loss of p38α-dependent counterregulatory responses. The p38α-dependent counterregulatory response relates to mitogen- and stress-activated protein kinase-I (MSK1), or MSK2. In targeting a pocket near the ED substrate-docking site of p38α, the inhibitors provided by the present disclosure avoid interfering with CD-specific substrates, including MSK1/2, thus limiting inflammation through expression of IL-10 and DUSP2.

ASPECTS OF THE INVENTION

The invention is further defined by the following aspects.
Aspect 1. A compound having the structure of Formula (1):

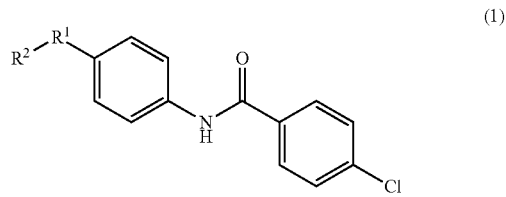

or a pharmaceutically acceptable salt thereof, wherein,
$R^1$ is selected from $C_{1-4}$ alkanediyl, $C_{1-4}$ heteroalkanediyl, substituted $C_{1-4}$ alkanediyl, and substituted $C_{1-4}$ heteroalkanediyl; and
$R^2$ is selected from a moiety of Formula (2a), a moiety of Formula (2b), a moiety of Formula (2c), $C_{8-16}$ heterobicycloalkyl, and substituted $C_{8-16}$ heterobicycloalkyl:

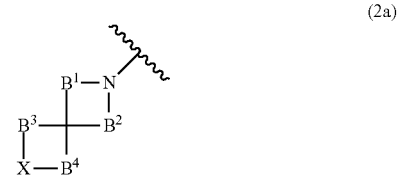

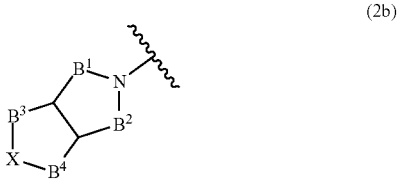

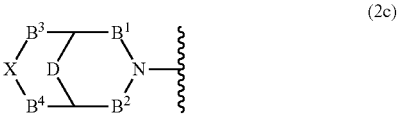

wherein, each of $B^1$, $B^2$, $B^3$, and $B^4$ is independently selected from —(CH(—$R^4$))$_n$—, wherein, each n is independently selected from, 0, 1, 2, 3, and 4;

both $B^1$ and $B^2$ are not 0;

both $B^3$ and $B^4$ are not 0; and each $R^4$ is independently selected from hydrogen, —OH, —NH$_2$, —NO$_2$, $C_{1-3}$ alkyl, $C_{1-3}$ heteroalkyl, substituted $C_{1-3}$ alkyl, and substituted $C_{1-3}$ heteroalkyl;

D is selected from methane-diyl and ethane-diyl; and

X is selected from —O—, —CH(—OH)—, —NR—, and —SO$_2$—, wherein $R^3$ is selected from hydrogen, $C_{1-6}$ alkyl, $C_{1-6}$ cycloalkyl, $C_6$ aryl, $C_{1-6}$ heteroalkyl, $C_{1-6}$ heterocycloalkyl, $C_{5-6}$ heteroaryl, substituted $C_{1-6}$ alkyl, substituted $C_{1-6}$ cycloalkyl, substituted $C_6$ aryl, substituted $C_{1-6}$ heteroalkyl, substituted $C_{1-6}$ heterocycloalkyl, and substituted $C_{5-6}$ heteroaryl.

Aspect 2. The compound of aspect 1, wherein each of the one or more substituents is independently selected from —OH, =O, —NH$_2$, —NO$_2$, $C_{1-6}$ alkyl, $C_{1-6}$ cycloalkyl, $C_6$ aryl, $C_{1-6}$ heteroalkyl, $C_{1-6}$ heterocycloalkyl, $C_{5-6}$ heteroaryl, substituted $C_{1-6}$ alkyl, substituted $C_{1-6}$ cycloalkyl, substituted $C_6$ aryl, substituted $C_{1-6}$ heteroalkyl, substituted $C_{1-6}$ heterocycloalkyl, and substituted $C_{5-6}$ heteroaryl.

Aspect 3. The compound of aspect 1, wherein each of the one or more substituents is independently selected from —OH, =O, —NH$_2$, —NO$_2$, $C_{1-3}$ alkyl, $C_{1-3}$ heteroalkyl, substituted $C_{1-3}$ alkyl, and substituted $C_{1-3}$ heteroalkyl.

Aspect 4. The compound of aspect 1, wherein each of the one or more substituents is independently selected from —OH, =O, and $C_{1-3}$ alkyl.

Aspect 5. The compound of any one of aspects 1 to 4, wherein $R^1$ is $C_{1-4}$ alkanediyl.

Aspect 6. The compound of any one of aspects 1 to 4, wherein $R^1$ is ethanediyl.

Aspect 7. The compound of any one of aspects 1 to 4, wherein $R^1$ is methanediyl.

Aspect 8. The compound of any one of aspects 1 to 7, wherein $R^2$ is a moiety of Formula (2a):

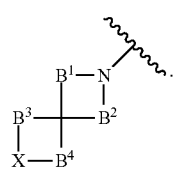

(2a)

Aspect 9. The compound of aspect 8, wherein each of $B^1$, $B^2$, $B^3$, and $B^4$ is independently selected from —(CH$_2$)$_n$—.

Aspect 10. The compound of aspect 8, wherein each of $B^1$ and $B^2$ is independently selected from —(CH$_2$)$_n$—.

Aspect 11. The compound of aspect 8, wherein each of $B^1$, $B^2$, and $B^3$ is independently selected from —(CH$_2$)$_n$—.

Aspect 12. The compound of aspect 8, wherein each of $B^1$, $B^2$, and $B^4$ is independently selected from —(CH$_2$)$_n$—.

Aspect 13. The compound of any one of aspects 8 to 12, wherein one of $B^1$, $B^2$, $B^3$, and $B^4$ comprises —CH(—$R^4$)—, wherein $R^4$ is selected from —OH, —NH$_2$, —NO$_2$, $C_{1-3}$ alkyl, $C_{1-3}$ heteroalkyl, substituted $C_{1-3}$ alkyl, and substituted $C_{1-3}$ heteroalkyl.

Aspect 14. The compound of any one of aspects 8 to 12, wherein two of $B^1$, $B^2$, $B^3$, and $B^4$ independently comprise —CH(—$R^4$)—, wherein $R^4$ is selected from —OH, —NH$_2$, —NO$_2$, $C_{1-3}$ alkyl, $C_{1-3}$ heteroalkyl, substituted $C_{1-3}$ alkyl, and substituted $C_{1-3}$ heteroalkyl.

Aspect 15. The compound of any one of aspects 8 to 12, wherein three of $B^1$, $B^2$, $B^3$, and $B^4$ independently comprise —CH(—$R^4$)—, wherein $R^4$ is selected from —OH, —NH$_2$, —NO$_2$, $C_{1-3}$ alkyl, $C_{1-3}$ heteroalkyl, substituted $C_{1-3}$ alkyl, and substituted $C_{1-3}$ heteroalkyl.

Aspect 16. The compound of any one of aspects 8 to 12, wherein each of $B^1$, $B^2$, $B^3$, and $B^4$ independently comprises —CH(—$R^4$)—, wherein $R^4$ is selected from —OH, —NH$_2$, —NO$_2$, $C_{1-3}$ alkyl, $C_{1-3}$ heteroalkyl, substituted $C_{1-3}$ alkyl, and substituted $C_{1-3}$ heteroalkyl.

Aspect 17. The compound of any one of aspects 8 to 16, wherein each n is independently selected from 0, 1, 2, and 3.

Aspect 18. The compound of any one of aspects 8 to 16, wherein each n is independently selected from 1, 2, and 3.

Aspect 19. The compound of any one of aspects 8 to 16, wherein, n in each of $B^1$ and $B^2$ is independently selected from 1 and 2; and n in each of $B^3$ and $B^4$ is 2.

Aspect 20. The compound of any one of aspects 8 to 16, wherein, n in each of $B^1$ and $B^2$ is 1; and n in each of $B^3$ and $B^4$ is 2.

Aspect 21. The compound of any one of aspects 8 to 16, wherein, n in each of $B^1$ and $B^2$ is 2; and n in each of $B^3$ and $B^4$ is 1.

Aspect 22. The compound of any one of aspects 8 to 16, wherein, n in each of $B^1$ and $B^2$ is 2; and n in each of $B^3$ and $B^4$ is 2.

Aspect 23. The compound of any one of aspects 8 to 16, wherein, n in each of $B^1$ and $B^2$ is 1; and n in each of $B^3$ and $B^4$ is 1.

Aspect 24. The compound of any one of aspects 8 to 24, wherein X is —O—.

Aspect 25. The compound of any one of aspects 8 to 24, wherein X is —CH(—OH)—.

Aspect 26. The compound of any one of aspects 8 to 24, wherein X is —SO$_2$—.

Aspect 27. The compound of any one of aspects 8 to 24, wherein X is —NR$^3$—.

Aspect 28. The compound of any one of aspects 8 to 24, wherein X is —NR$^3$—, and $R^3$ is selected from hydrogen, $C_{1-3}$ alkyl, $C_{1-3}$ heteroalkyl, substituted $C_{1-3}$ alkyl, and substituted $C_{1-3}$ heteroalkyl.

Aspect 29. The compound of any one of aspects 8 to 24, wherein X is —NR$^3$—, and $R^3$ is —C(=O)—CH$_3$.

Aspect 30. The compound of any one of aspects 8 to 24, wherein X is —NR$^3$—, and $R^3$ is —CH$_3$.

Aspect 31. The compound of any one of aspects 1 to 7, wherein $R^2$ is a moiety of Formula (2b):

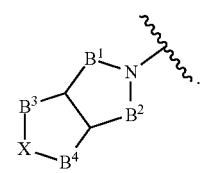

(2b)

Aspect 32. The compound of aspect 31, wherein each of $B^1$, $B^2$, $B^3$, and $B^4$ is independently selected from —(CH$_2$)$_n$—.

Aspect 33. The compound of aspect 31, wherein each of $B^1$ and $B^2$ is independently selected from —(CH$_2$)$_n$—.

Aspect 34. The compound of aspect 31, wherein each of $B^1$, $B^2$, and $B^3$ is independently selected from —$(CH_2)_n$—.

Aspect 35. The compound of aspect 31, wherein each of $B^1$, $B^2$, and $B^4$ is independently selected from —$(CH_2)_n$—.

Aspect 36. The compound of any one of aspects 31 to 35, wherein one of $B^1$, $B^2$, $B^3$, and $B^4$ comprises —CH(—$R^4$)—, wherein $R^4$ is selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

Aspect 37. The compound of any one of aspects 31 to 35, wherein two of $B^1$, $B^2$, $B^3$, and $B^4$ independently comprise —CH(—$R^4$)—, wherein $R^4$ is selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

Aspect 38. The compound of any one of aspects 31 to 35, wherein three of $B^1$, $B^2$, $B^3$, and $B^4$ independently comprise —CH(—$R^4$)—, wherein $R^4$ is selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

Aspect 39. The compound of any one of aspects 31 to 35, wherein each of $B^1$, $B^2$, $B^3$, and $B^4$ independently comprises —CH(—$R^4$)—, wherein $R^4$ is selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

Aspect 40. The compound of any one of aspects 31 to 39, wherein each n is independently selected from 1 and 2.

Aspect 41. The compound of any one of aspects 31 to 39, wherein each n is 1.

Aspect 42. The compound of any one of aspects 31 to 39, wherein, n in each of $B^1$ and $B^2$ is 1; and n in each of $B^3$ and $B^4$ is 2.

Aspect 43. The compound of any one of aspects 31 to 39, wherein, n in each of $B^1$ and $B^2$ is 2; and n in each of $B^3$ and $B^4$ is 1.

Aspect 44. The compound of any one of aspects 31 to 39, wherein, n in each of $B^1$, $B^2$, and $B^3$ is 1, and n in $B^4$ is 2.

Aspect 45. The compound of aspect 21, wherein, n in each of $B^1$, $B^2$, and $B^3$ is 2, and n in $B^4$ is 1.

Aspect 46. The compound of any one of aspects 31 to 45, wherein X is —O—.

Aspect 47. The compound of any one of aspects 31 to 45, wherein X is —CH(—OH)—.

Aspect 48. The compound of any one of aspects 31 to 45, wherein X is —$SO_2$—.

Aspect 49. The compound of any one of aspects 31 to 45, wherein X is —$NR^3$—.

Aspect 50. The compound of any one of aspects 31 to 45, wherein X is —$NR^3$—, and $R^3$ is selected from hydrogen, $C_{1-3}$ alkyl, $C_{1-3}$ heteroalkyl, substituted $C_{1-3}$ alkyl, and substituted $C_{1-3}$ heteroalkyl.

Aspect 51. The compound of any one of aspects 31 to 45, wherein X is —$NR^3$—, and $R^3$ is —C(=O)—$CH_3$.

Aspect 52. The compound of any one of aspects 31 to 45, wherein X is —$NR^3$—, and $R^3$ is —$CH_3$.

Aspect 53. The compound of any one of aspects 1 to 7, wherein $R^2$ is a moiety of Formula (2c).

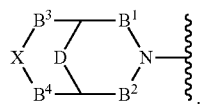

(2c)

Aspect 54. The compound of aspect 53, wherein each of $B^1$, $B^2$, $B^3$, and $B^4$ is independently selected from —$(CH_2)_n$—.

Aspect 55. The compound of aspect 53, wherein each of $B^1$ and $B^2$ is independently selected from —$(CH_2)_n$—.

Aspect 56. The compound of aspect 53, wherein each of $B^1$, $B^2$, and $B^3$ is independently selected from —$(CH_2)_n$—.

Aspect 57. The compound of aspect 53, wherein each of $B^1$, $B^2$, and $B^4$ is independently selected from —$(CH_2)_n$—.

Aspect 58. The compound of any one of aspects 53 to 57, wherein one of $B^1$, $B^2$, $B^3$, and $B^4$ comprises —CH(—$R^4$)—, wherein $R^4$ is selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

Aspect 59. The compound of any one of aspects 53 to 57, wherein two of $B^1$, $B^2$, $B^3$, and $B^4$ independently comprise —CH(—$R^4$)—, wherein $R^4$ is selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

Aspect 60. The compound of any one of aspects 53 to 57, wherein three of $B^1$, $B^2$, $B^3$, and $B^4$ independently comprise —CH(—$R^4$)—, wherein $R^4$ is selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

Aspect 61. The compound of any one of aspects 53 to 57, wherein each of $B^1$, $B^2$, $B^3$, and $B^4$ independently comprise —CH(—$R^4$)—, wherein $R^4$ is selected from —OH, —$NH_2$, —$NO_2$, $C_{1-3}$ alkyl, $C_{1-3}$ heteroalkyl, substituted $C_{1-3}$ alkyl, and substituted $C_{1-3}$ heteroalkyl.

Aspect 62. The compound of any one of aspects 53 to 61, wherein each n is independently selected from 1 and 2.

Aspect 63. The compound of any one of aspects 53 to 61, wherein each n is 1.

Aspect 64. The compound of any one of aspects 53 to 61, wherein, n in each of $B^1$ and $B^2$ is 1; and n in each of $B^3$ and $B^4$ is 2.

Aspect 65. The compound of any one of aspects 53 to 61, wherein, n in each of $B^1$ and $B^2$ is 2; and n in each of $B^3$ and $B^4$ is 1.

Aspect 66. The compound of any one of aspects 53 to 61, wherein, each n is 2.

Aspect 67. The compound of any one of aspects 53 to 61, wherein, each n is 1.

Aspect 68. The compound of any one of aspects 53 to 67, wherein D is methanediyl.

Aspect 69. The compound of any one of aspects 53 to 67, wherein D is ethanediyl.

Aspect 70. The compound of any one of aspects 53 to 67, wherein X is —O—.

Aspect 71. The compound of any one of aspects 53 to 67, wherein X is —CH(—OH)—.

Aspect 72. The compound of any one of aspects 53 to 67, wherein X is —$SO_2$—.

Aspect 73. The compound of any one of aspects 53 to 67, wherein X is —$NR^3$—.

Aspect 74. The compound of any one of aspects 53 to 67, wherein X is —$NR^3$—, and $R^3$ is selected from hydrogen, $C_{1-3}$ alkyl, $C_{1-3}$ heteroalkyl, substituted $C_{1-3}$ alkyl, and substituted $C_{1-3}$ heteroalkyl.

Aspect 75. The compound of any one of aspects 53 to 67, wherein X is —$NR^3$—, and $R^3$ is —C(=O)—$CH_3$.

Aspect 76. The compound of any one of aspects 53 to 67, wherein X is —$NR^3$—, and $R^3$ is —$CH_3$.

Aspect 77. The compound of aspect 53, wherein the compound is selected from:
N-(4-((2-oxa-6-azaspiro[3.3]heptan-6-yl)methyl)phenyl)-4-chlorobenzamide (3);

N-(4-((7-oxa-2-azaspiro[3.5]nonan-2-yl)methyl)phenyl)-4-chlorobenzamide (4);
N-(4-((8-oxa-2-azaspiro[4.5]decan-2-yl)methyl)phenyl)-4-chlorobenzamide (5);
N-(4-((1-oxa-7-azaspiro[4.4]nonan-7-yl)methyl)phenyl)-4-chlorobenzamide (6);
N-(4-(((1R,5S)-3-oxa-7-azabicyclo[3.3.1]nonan-7-yl)methyl)phenyl)-4-chlorobenzamide_(9); and
4-chloro-N-(4-(((3aR,6aS)-tetrahydro-1H-furo[3,4-c]pyrrol-5(3H)-yl)methyl)phenyl)benzamide (10);
or a pharmaceutically acceptable salt of any of the foregoing.

Aspect 78. A compound having the structure of Formula (1):

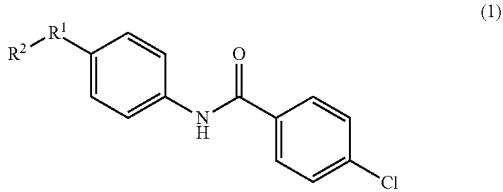

or a pharmaceutically acceptable salt thereof, wherein,
$R^1$ is selected from $C_{1-4}$ alkanediyl, $C_{1-4}$ heteroalkanediyl, substituted $C_{1-4}$ alkanediyl, and substituted $C_{1-4}$ heteroalkanediyl; and
$R^2$ is a moiety of Formula (2d):

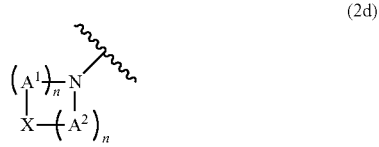

wherein,
each $A^1$ and $A^2$ is independently selected from —$CH_2$—, —CH(—$R^5$)—, and —C(=O)—, wherein, each $R^5$ is independently selected from —OH, —$NH_2$, —$NO_2$, $C_{1-6}$ alkyl, $C_{1-6}$ cycloalkyl, $C_6$ aryl, $C_{1-6}$ heteroalkyl, $C_{1-6}$ heterocycloalkyl, $C_{5-6}$ heteroaryl, substituted $C_{1-6}$ alkyl, substituted $C_{1-6}$ cycloalkyl, substituted $C_6$ aryl, substituted $C_{1-6}$ heteroalkyl, substituted $C_{1-6}$ heterocycloalkyl, and substituted $C_{5-6}$ heteroaryl;
one or more of $A^1$ and $A^2$ is independently selected from —CH(—$R^5$)— and —C(=O)—;
each n is independently selected from, 1, 2, 3, and 4; and
X is selected from —O—, —CH(—OH)—, —$NR^3$—, and —$SO_2$—, wherein $R^3$ is selected from hydrogen, $C_{1-6}$ alkyl, $C_{5-8}$ cycloalkyl, $C_6$ aryl, $C_{6-12}$ cycloalkylalkyl, $C_{7-10}$ arylalkyl, $C_{1-6}$ heteroalkyl, $C_{5-8}$ heterocycloalkyl, $C_{5-6}$ heteroaryl, $C_{6-12}$ heterocycloalkylalkyl, $C_{7-10}$ heteroarylalkyl, substituted $C_{1-6}$ alkyl, substituted $C_{5-8}$ cycloalkyl, substituted $C_6$ aryl, substituted $C_{6-12}$ cycloalkylalkyl, substituted $C_{7-10}$ arylalkyl, substituted $C_{1-6}$ heteroalkyl, substituted $C_{5-8}$ heterocycloalkyl, substituted $C_{5-6}$ heteroaryl, substituted $C_{6-12}$ heterocycloalkylalkyl, and substituted $C_{7-10}$ heteroarylalkyl.

Aspect 79. The compound of aspect 78, wherein $R^1$ is $C_{1-4}$ alkanediyl.

Aspect 80. The compound of aspect 78, wherein $R^1$ is ethanediyl.

Aspect 81. The compound of aspect 78, wherein $R^1$ is methanediyl.

Aspect 82. The compound of any one of aspects 78 to 81, wherein each n is independently selected from 1, 2, and 3.

Aspect 83. The compound of any one of aspects 78 to 81, wherein each n is 2.

Aspect 84. The compound of any one of aspects 78 to 81, wherein each n is 3.

Aspect 85. The compound of any one of aspects 78 to 81, wherein each n is 4.

Aspect 86. The compound of any one of aspects 78 to 81, wherein one or more of $A^1$ and $A^2$ is independently selected from —CH(—$R^5$)—, wherein $R^5$ is $C_{1-3}$ alkyl; and —C(=O)—.

Aspect 87. The compound of any one of aspects 78 to 81, wherein one or more of $A^1$ and $A^2$ is independently selected from —CH(—$R^5$)—, wherein $R^5$ is $C_{1-3}$ alkyl.

Aspect 88. The compound of any one of aspects 78 to 81, wherein one or more of $A^1$ and $A^2$ is —C(=O)—.

Aspect 89. The compound of any one of aspects 78 to 88, wherein X is —O—.

Aspect 90. The compound of any one of aspects 78 to 88, wherein X is —CH(—OH)—.

Aspect 91. The compound of any one of aspects 78 to 88, wherein X is —$SO_2$—.

Aspect 92. The compound of any one of aspects 78 to 88, wherein X is —$NR^3$—.

Aspect 93. The compound of any one of aspects 78 to 88, wherein X is —$NR^3$—, and $R^3$ is selected from hydrogen, $C_{1-3}$ alkyl, $C_{1-3}$ heteroalkyl, substituted $C_{1-3}$ alkyl, and substituted $C_{1-3}$ heteroalkyl.

Aspect 94. The compound of any one of aspects 78 to 88, wherein X is —$NR^3$—, and $R^3$ is —C(=O)—$CH_3$.

Aspect 95. The compound of any one of aspects 78 to 88, wherein X is —$NR^3$—, and $R^3$ is —$CH_3$.

Aspect 96. The compound of aspect 78, wherein the compound is selected from:
2-chloro-N-(4-(morpholinomethyl)phenyl)pyrimidine-5-carboxamide (1);
N-(4-((1,4-oxazepan-4-yl)methyl)phenyl)-4-chlorobenzamide (2);
4-chloro-N-(4-(((2S,6R)-2,6-dimethylmorpholino)methyl)phenyl)benzamide (7);
4-chloro-N-(4-(((2S,6S)-2,6-dimethylmorpholino)methyl)phenyl)benzamide (8);
4-chloro-N-(4-((4-hydroxypiperidin-1-yl)methyl)phenyl)benzamide (11);
4-chloro-N-(4-((3-hydroxypiperidin-1-yl)methyl)phenyl)benzamide (12);
4-chloro-N-(4-((3-hydroxypyrrolidin-1-yl)methyl)phenyl)benzamide (13);
N-(4-((4-acetylpiperazin-1-yl)methyl)phenyl)-4-chlorobenzamide (14);
4-chloro-N-(4-((3-oxopiperazin-1-yl)methyl)phenyl)benzamide (15);
4-chloro-N-(4-((4-methyl-3-oxopiperazin-1-yl)methyl)phenyl)benzamide (16); and
4-chloro-N-(4-((4-methylpiperazin-1-yl)methyl)phenyl)benzamide (17);
or a pharmaceutically acceptable salt of any of the foregoing.

Aspect 97. The compound of any one of aspects 1 to 96, wherein the compound inhibits the p38α MAPK receptor.

Aspect 98. The compound of any one of aspects 1 to 96, wherein the compound selectively inhibits the p38α MAPK receptor.

Aspect 99. The compound of any one of aspects 1 to 96, wherein the compound has a higher binding affinity to the p38α MAPK subunit than to the p38β MAPK subunit.

Aspect 100. The compound of any one of aspects 1 to 96, wherein the compound binds to a selective binding site of p38α MAPK, wherein the binding pocket is defined by pocket can be defined at least by residues R49, H107, L108, and K165 of p38α MAPK.

Aspect 101. The compound of any one of aspects 1 to 96, wherein the compound binds competitively binds to the selective binding site competitively with 4-chloro-N-(4-((1,1-dioxidothiomorpholino)methyl)phenyl)benzamide.

Aspect 102. The compound of any one of aspects 1 to 96, wherein the compound inhibits MK2 phosphorylation of in anisomycin-stimulated HeLa cells by 4-chloro-N-(4-((1,1-dioxidothiomorpholino)methyl)phenyl)benzamide.

Aspect 103. A pharmaceutical composition comprising the compound of any one of aspects 1 to 96 or a pharmaceutically acceptable salt thereof.

Aspect 104. The pharmaceutical composition of aspect 99, wherein the pharmaceutical composition comprises a therapeutically effective amount of the compound of any one of aspects 1 to 96 or a pharmaceutically acceptable salt thereof for treating a disease in a patient.

Aspect 105. The pharmaceutical composition of aspect 104, wherein the disease is treated by inhibiting the p38α MAPK receptor.

Aspect 106. The pharmaceutical composition of aspect 104, wherein the disease is cancer.

Aspect 107. The pharmaceutical composition of aspect 104, wherein the disease is an inflammatory disease.

Aspect 108. The pharmaceutical composition of aspect 104, wherein the disease is an autoimmune disease.

Aspect 109. The pharmaceutical composition of aspect 104, wherein the disease is selected from acute lung injury, acute respiratory distress syndrome (ARDS), and chronic obstructive pulmonary disease (COPD).

Aspect 110. A method of treating a disease in a patient comprising administering to a patient in need thereof a therapeutically effective of amount of the compound of any one of aspects 1 to 96 or a pharmaceutically acceptable salt thereof, wherein the disease is treated by inhibiting the p38α MAPK receptor.

Aspect 111. A method of treating a disease in a patient comprising administering to a patient in need thereof a therapeutically effective of amount of the compound of any one of aspects 1 to 96 or a pharmaceutically acceptable salt thereof, wherein the disease is cancer.

Aspect 112. The method of aspect 111, wherein the cancer is selected from breast cancer and melanoma.

Aspect 113. A method of treating a disease in a patient comprising administering to a patient in need thereof a therapeutically effective of amount of the compound of any one of aspects 1 to 96 or a pharmaceutically acceptable salt thereof, wherein the disease is an inflammatory disease.

Aspect 114. The method of aspect 113, wherein the inflammatory disease is selected from acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes, and rheumatoid arthritis.

Aspect 115. A method of treating a disease in a patient comprising administering to a patient in need thereof a therapeutically effective of amount of the compound of any one of aspects 1 to 96 or a pharmaceutically acceptable salt thereof, wherein the disease is an autoimmune disease.

Aspect 116. A method of treating a disease in a patient comprising administering to a patient in need thereof a therapeutically effective of amount of the compound of any one of aspects 1 to 96 or a pharmaceutically acceptable salt thereof, wherein the disease is an age-related disease.

Aspect 117. The method of aspect 116, wherein the age-related disease is selected from hearing loss, muscle degeneration, Werner's syndrome, cellular aging, and Alzheimer's disease.

Aspect 118. A method of treating a disease in a patient comprising administering to a patient in need thereof a therapeutically effective of amount of the compound of any one of aspects 1 to 96 or a pharmaceutically acceptable salt thereof, wherein the disease is selected from acute lung injury, acute respiratory distress syndrome (ARDS), and chronic obstructive pulmonary disease (COPD).

Aspect 119. A method of inhibiting the p38α MAPK receptor comprising contacting the p38α MAPK receptor with the compound of any one of aspects 1 to 96 or a pharmaceutically acceptable salt thereof.

Aspect 120. A method of inhibiting the p38α MAPK receptor in a patient comprising administering to a patient a pharmacologically effective amount of the compound of any one of aspects 1 to 96 or a pharmaceutically acceptable salt thereof.

Aspect 121. The method of aspect 120, wherein inhibiting the p38α MAPK receptor comprises selectively inhibiting the p38α MAPK receptor.

Aspect 122. The method of aspect 121, wherein inhibiting the p38α MAPK receptor does not result in loss of a p38α-dependent counterregulatory response.

Aspect 123. The method of aspect 122, wherein the p38α-dependent counterregulatory response relates to mitogen- and stress-activated protein kinase-1 (MSK1) or MSK2.

Aspect 124. The method of any one of aspects 119 to 123, wherein inhibiting the p38α MAPK receptor stabilizes an endothelial or epithelial barrier function.

Aspect 125. The method of any one of aspects 119 to 124, wherein inhibiting the p38α MAPK receptor reduces inflammation.

Aspect 126. The method of any one of aspects 119 to 125, wherein inhibiting the p38α MAPK receptor mitigates KPS-induced lung injury.

Aspect 127. The method of any one of aspects 119 to 126, wherein inhibiting the p38α MAPK receptor regulates leukocyte trafficking.

Aspect 128. The method of any one of aspects 119 to 127, wherein inhibiting the p38α MAPK receptor regulates cytokine expression.

Aspect 1A. The compound of aspect 8, wherein $B^1$ is $—(CH_2)_2—$; $B^2$ is $—CH_2—$; $B^3$ is $—(CH_2)_n—$ wherein n is selected from 0, 1, 2, and 3; $B^3$ is $—(CH_2)_{3n}—$; and X is O.

Aspect 2A. The compound of aspect 8, wherein the moiety of Formula (2a) is selected from a moiety of Formula (2a.1) to (2a.4):

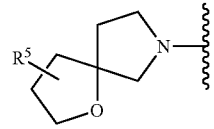

(2d.1)

-continued

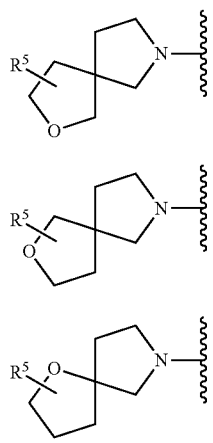

(2d.2)

(2d.3)

(2d.4)

where R⁵ is selected from hydrogen (unsubstituted), —OH, —NH₂, —NR₂ wherein each R is independently selected from hydrogen and $C_{1-3}$ alkyl, —NO₂, =O, $C_{1-3}$ alkoxy, and C(=O)—R where R is $C_{1-3}$ alkyl.

Aspect 3A. The compound of aspect 78, wherein $A^1$ is —(CH₂)$_n$— where n is an integer from 1 to 4; $A^2$ is —(CH₂)$_{5-n}$—; and X is O.

Aspect 4A. The compound of aspect 78, wherein the moiety of Formula (2d) can have the structure of Formula (2d.1) or Formula (2d.2):

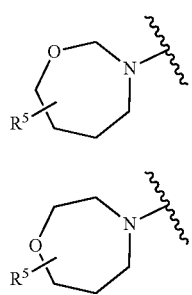

(2d.1)

(2d.2)

where R⁵ is selected from hydrogen (unsubstituted), —OH, —NH₂, —NR₂ wherein each R is independently selected from hydrogen and $C_{1-3}$ alkyl, —NO₂, =O, $C_{1-3}$ alkoxy, and C(=O)—R where R is $C_{1-3}$ alkyl.

Aspect 5A. The compound of aspect 78, wherein $A^1$ is —(CH₂)$_n$— where n is 1 or 2; $A^2$ is —(CH₂)$_{3-n}$—; and X is —N(—C(=O)—R⁶)— where R⁶ is selected from.

Aspect 6A. The compound of aspect 78, wherein the moiety of Formula (2d) is selected from a moiety of Formula (2d.3) and Formula (2d.4):

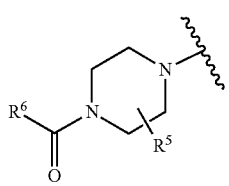

(2d.3)

-continued

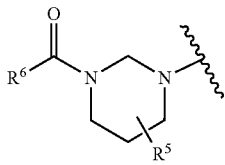

(2d.4)

where,

R⁵ is selected from hydrogen (unsubstituted), —OH, —NH₂, —NR₂ wherein each R is independently selected from hydrogen and $C_{1-3}$ alkyl, —NO₂, =O, $C_{1-3}$ alkoxy, and C(=O)—R where R is $C_{1-3}$ alkyl; and R⁶ is selected from $C_{1-6}$ alkyl and $C_{1-6}$ alkoxy.

Aspect 7A. The compound of aspect 78, wherein $A^1$ is —(CH₂)$_n$— where n is 1 or 2; $A^2$ is —(CH₂)$_{3-n}$—; and X is O, and is comprise 1 or 2 —CH₃ substituents.

Aspect 8A. The compound of aspect 78, wherein the moiety of Formula (2d) can have the structure of Formula (2d.5):

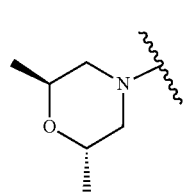

(2d.5)

Aspect 9A. A compound having the structure of Formula (1):

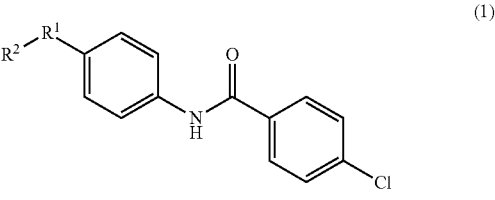

(1)

or a pharmaceutically acceptable salt thereof, where, $R^1$ is selected from $C_{1-4}$ alkanediyl; and $R^2$ is selected from a substituted or unsubstituted moiety of any one of Formula (2a.1) to (2a.4) and (2d.1) to (2d.5):

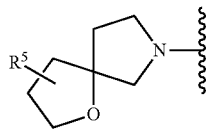

(2a.1)

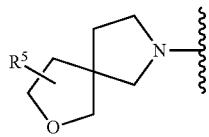

(2a.2)

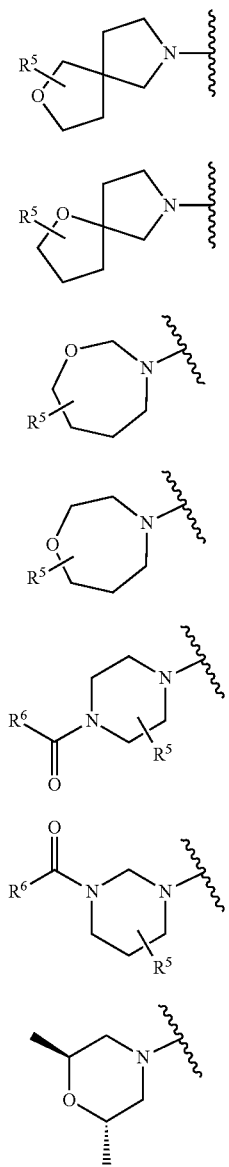

(2a.3)

(2a.4)

(2d.1)

(2d.2)

(2d.3)

(2d.4)

(2d.5)

wherein,

R⁵ is selected from hydrogen (unsubstituted), —OH, —NH₂, —NR₂ wherein each R is independently selected from hydrogen and $C_{1-3}$ alkyl, —NO₂, =O, $C_{1-3}$ alkoxy, and C(=O)—R where R is $C_{1-3}$ alkyl; and R⁶ is selected from $C_{1-6}$ alkyl and $C_{1-6}$ alkoxy.

Aspect 10A. The compound of aspect 9A, wherein R¹ is selected from methane-diyl, ethane-diyl, and n-propane-diyl.

Aspect 11A. The compound of aspect 9A, wherein R¹ is methane-diyl.

Aspect 12A. The compound of any one of aspects 9A to 11A, wherein R² is selected from an unsubstituted moiety of any one of Formula (2a.1) to (2a.4) and (2d.1) to (2d.5).

Aspect 13A. The compound of any one of aspects 9A to 11A, wherein R² is selected from a substituted moiety of any one of Formula (2a.1) to (2a.4) and (2d.1) to (2d.5).

Aspect 14A. The compound of any one of aspects 9A to 11A, wherein the substituted moiety can have the structure of any one of Formula (2a.1) to (2a.4) and (2d.1) to (2d.5):

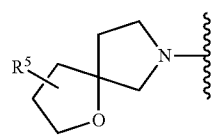

(2a.1)

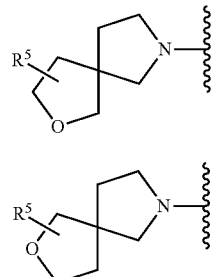

(2a.2)

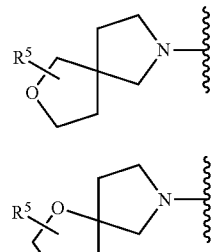

(2a.3)

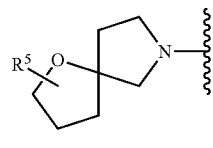

(2a.4)

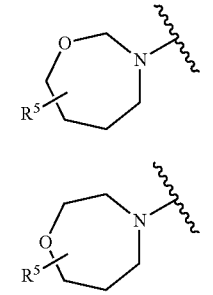

(2d.1)

(2d.2)

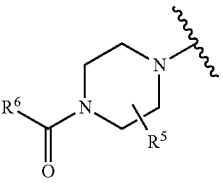

(2d.3)

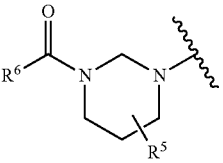

(2d.4)

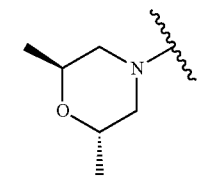

(2d.5)

wherein,

R⁵ is selected from —OH, —NH₂, —NR₂ wherein each R is independently selected from hydrogen and $C_{1-3}$ alkyl, —NO₂, =O, $C_{1-3}$ alkoxy, and C(=O)—R where R is $C_{1-3}$ alkyl; and R⁶ is selected from $C_{1-6}$ alkyl and $C_{1-6}$ alkoxy.

Aspect 15A. A pharmaceutical composition comprising the compound of any one of aspects 1A to 14A, or pharmaceutically acceptable salt thereof.

Aspect 16A. The pharmaceutical composition of aspect 15A, wherein the pharmaceutical composition comprises a therapeutically effective amount of the compound of any one of aspects 1A to 14A or a pharmaceutically acceptable salt thereof for treating a disease in a patient.

Aspect 17A. The pharmaceutical composition of aspect 16A, wherein the disease is treated by inhibiting the p38α MAPK receptor.

Aspect 18A. The pharmaceutical composition of aspect 16A, wherein the disease is cancer.

Aspect 19A. The pharmaceutical composition of aspect 16A, wherein the disease is an inflammatory disease.

Aspect 20A. The pharmaceutical composition of aspect 16A, wherein the disease is an autoimmune disease.

Aspect 21A. The pharmaceutical composition of aspect 16A, wherein the disease is selected from acute lung injury, acute respiratory distress syndrome (ARDS), chronic obstructive pulmonary disease (COPD), amyotrophic lateral sclerosis, an cystic fibrosis.

Aspect 22A. The pharmaceutical composition of aspect 16A, wherein the disease is selected from acute lung injury, acute respiratory distress syndrome (ARDS), and chronic obstructive pulmonary disease (COPD).

Aspect 23A. The pharmaceutical composition of aspect 16A, wherein the disease is a viral disease.

Aspect 24A. The pharmaceutical composition of aspect 16A, wherein the viral disease is selected from a coronavirus infection such as a MERS-CoV infection, a SARS-CoV infection, or a SARS-CoV-2 infection, pneumonia associated with a coronavirus infection, and a Human Respiratory Syndical infection.

Aspect 25A. A method of treating a disease in a patient comprising administering to a patient in need thereof a therapeutically effective of amount of the compound of any one of aspects 1A to 14A or a pharmaceutically acceptable salt thereof, wherein the disease is treated by inhibiting the p38α MAPK receptor.

Aspect 26A. A method of treating a disease in a patient comprising administering to a patient in need thereof a therapeutically effective of amount of the compound of any one of aspects 1A to 14A or a pharmaceutically acceptable salt thereof, wherein the disease is cancer.

Aspect 27A. The method of aspect 26A, wherein the cancer is selected from breast cancer and melanoma.

Aspect 28A. A method of treating a disease in a patient comprising administering to a patient in need thereof a therapeutically effective of amount of the compound of any one of aspects 1A to 14A or a pharmaceutically acceptable salt thereof, wherein the disease is an inflammatory disease.

Aspect 29A. The method of aspect 28A, wherein the inflammatory disease is selected from acute respiratory distress syndrome, focal segmental glomerulonephritis, atherosclerosis/acute coronary syndrome, chronic obstructive pulmonary disease, asthma, inflammatory bowel disease, Crohn's disease, psoriasis, lupus, multiple sclerosis, inflammation in hypercholesteremia, pain, diabetes, and rheumatoid arthritis.

Aspect 30A. A method of treating a disease in a patient comprising administering to a patient in need thereof a therapeutically effective of amount of the compound of any one of aspects 1A to 14A or a pharmaceutically acceptable salt thereof, wherein the disease is an autoimmune disease.

Aspect 31A. A method of treating a disease in a patient comprising administering to a patient in need thereof a therapeutically effective of amount of the compound of any one of aspects 1A to 14A or a pharmaceutically acceptable salt thereof, wherein the disease is an age-related disease.

Aspect 32A. The method of aspect 31A, wherein the age-related disease is selected from hearing loss, muscle degeneration, Werner's syndrome, cellular aging, and Alzheimer's disease.

Aspect 33A. A method of treating a disease in a patient comprising administering to a patient in need thereof a therapeutically effective of amount of the compound of any one of aspects 1A to 14A or a pharmaceutically acceptable salt thereof, wherein the disease is selected from acute lung injury, acute respiratory distress syndrome (ARDS), chronic obstructive pulmonary disease (COPD amyotrophic lateral sclerosis, an cystic fibrosis.

Aspect 34A. A method of inhibiting the p38α MAPK receptor comprising contacting the p38α MAPK receptor with the compound of any one of aspects 1A to 14A or a pharmaceutically acceptable salt thereof.

Aspect 35A. A method of inhibiting the p38α MAPK receptor in a patient comprising administering to a patient a pharmacologically effective amount of the compound of any one of aspects A1A to 14A or a pharmaceutically acceptable salt thereof.

Aspect 36A. The method of aspect 35A, wherein inhibiting the p38α MAPK receptor comprises selectively inhibiting the p38α MAPK receptor.

Aspect 37A. The method of aspect 36A, wherein inhibiting the p38α MAPK receptor does not result in loss of a p38α-dependent counterregulatory response.

Aspect 38A. The method of aspect 37A, wherein the p38α-dependent counterregulatory response relates to mitogen- and stress-activated protein kinase-1 (MSK1) or MSK2.

Aspect 39A. The method of any one of aspects 34A to 38A, wherein inhibiting the p38α MAPK receptor stabilizes an endothelial or epithelial barrier function.

Aspect 40A. The method of any one of aspects 34A to 39A, wherein inhibiting the p38α MAPK receptor reduces inflammation.

Aspect 41A. The method of any one of aspects 34A to 40A, wherein inhibiting the p38α MAPK receptor mitigates KPS-induced lung injury.

Aspect 42A. The method of any one of aspects 34A to 41A, wherein inhibiting the p38α MAPK receptor regulates leukocyte trafficking.

Aspect 43A. The method of any one of aspects 34A to 42A, wherein inhibiting the p38α MAPK receptor regulates cytokine expression.

Aspect 44A. The pharmaceutical composition of any one of aspects 103 to 104, wherein the disease is a viral disease.

Aspect 45A. The pharmaceutical composition of aspect 44A, wherein the viral disease is selected from coronavirus infection such as a MERS-CoV infection, a SARS-CoV infection, or a SARS-CoV-2 infection.

Aspect 46A. The method of aspect 111, wherein the disease is a viral disease.

Aspect 47A. The method of aspect 46A, wherein the viral disease is selected from coronavirus infection such as a MERS-CoV infection, a SARS-CoV infection, or a SARS-CoV-2 infection.

EXAMPLES

The following examples describe in detail the synthesis of compounds of Formula (1), the characterization of compounds of Formula (1), and uses of compounds of Formula

Example A

Synthesis of 4-chloro-N-(4-(hydroxymethyl)phenyl)benzamide (A)

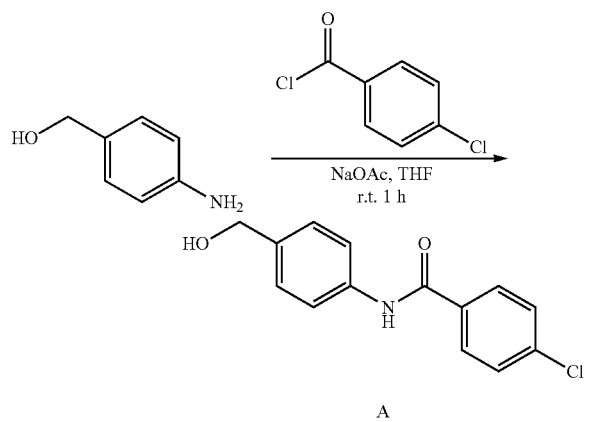

4-Chlorobenzoyl chloride (15.63 g, 89.32 mmol) was slowly added to a stirred solution of (4-aminophenyl)methanol (10 g, 81.2 mmol) and sodium acetate (10 g, 121.8 mmol) in THF (100 mL) at room temperature. Upon completion of adding, the reaction mixture was stirred at room temperature for 1.5 h. The reaction mixture was diluted with water (50 mL) and extracted with ethyl acetate (40 mL×3). The combined organic extracts were washed with water (100 mL×2) and saturated sodium chloride solution (100 mL), dried over anhydrous sodium sulfate, filtered and concentrated under reduced to dryness. The resulting residue was purified by silica gel column (DCM:MeOH=50:1, v/v) to afford 4-chloro-N-(4-(hydroxymethyl)phenyl)benzamide (A) (19.53 g, 91.9% yield) as a white solid. LCMS (Agilent): Rt=1.47 min; m/z calculated for [M+H]$^+$ 262.1, found 262.1. $^1$H-NMR (400 MHz, DMSO-d$_6$) δ 10.27 (s, 1H), 7.99-7.96 (m, 2H), 7.70 (d, J=8.4 Hz, 2H), 7.62-7.58 (m, 2H), 7.29 (dd, J=6.4, 2.0 Hz, 2H), 5.12 (t, J=5.2 Hz, 1H), 4.46 (d, J=5.2 Hz, 2H).

Example B

Synthesis of 4-chloro-N-(4-(chloromethyl)phenyl)benzaide (B)

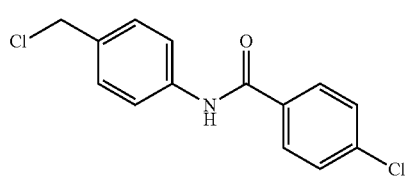 [SMILES: O=C(Nc1ccc(CCl)cc1)c1ccc(Cl)cc1]

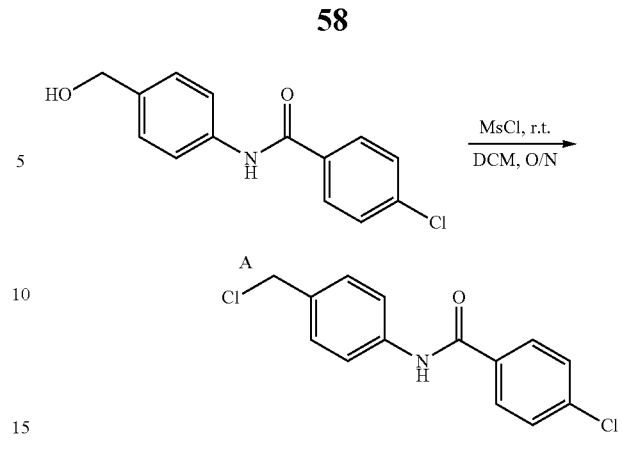

Methanesulfonyl chloride (1.75 g, 15.28 mmol) was added in a dropwise fashion to a stirred a solution of 4-chloro-N-(4-(hydroxymethyl)phenyl)benzamide (A) (2.00 g, 7.64 mmol) and triethylamine (1.53 g, 15.28 mmol) in DCM (25 mL) at room temperature. Upon completion of addition, the reaction mixture was stirred at room temperature for 2 h. The reaction mixture was diluted with H$_2$O (20 mL) and extracted with DCM (20 mL×3). The combined organic extracts were washed with H$_2$O (30 mL) and saturated sodium chloride solution (20 mL), dried over anhydrous sodium sulfate, filtered and concentrated to dryness under reduced pressure to afford the title compound (B) (627 mg, 29.3% yield) as a white solid. The structure was confirmed by LCMS and $^1$H-NMR. TLC: R$_f$=0.4 (silica gel, PE/EtOAc=3/1, v/v). LCMS (Agilent): Rt=2.30 min; m/z calculated for [M+H]$^+$ 280.0, found 280.0/282.1. $^1$H-NMR (400 MHz, DMSO-d$_6$) δ 10.39 (s, 1H), 7.98 (dd, J=6.4, 2.0 Hz, 2H), 7.77 (dd, J=6.4, 2.0 Hz, 2H), 7.61 (dd, J=6.8, 2.0 Hz, 2H), 7.42 (dd, J=6.8, 2.0 Hz, 2H), 4.75 (s, 2H).

Example 1

Synthesis of N-(4-((1,4-oxazepan-4-yl)methyl)phenyl)-4-chlorobenzamide (1)

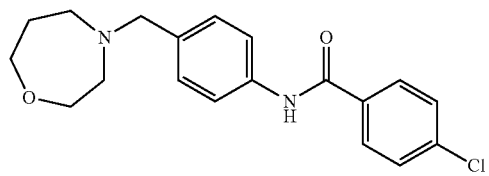 [SMILES: O=C(Nc1ccc(CN2CCCOCC2)cc1)c1ccc(Cl)cc1]

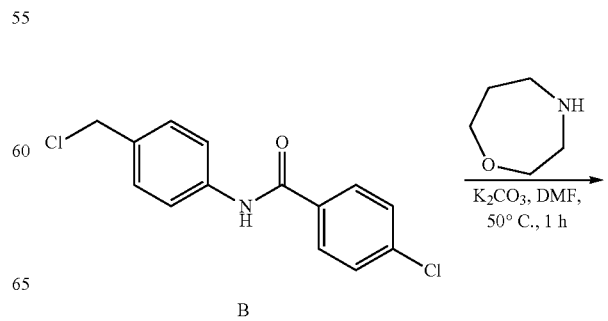

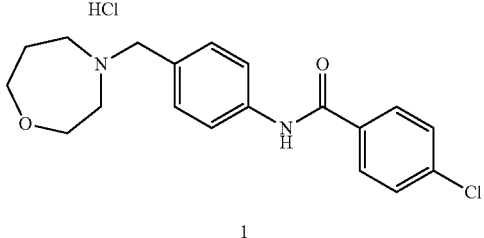

1

Anhydrous potassium carbonate (99 mg, 0.71 mmol) was added in one lot to a stirred solution of compound (B) (100 mg, 0.36 mmol) and 1,4-oxazepane (44 mg, 0.45 mmol) in DMF (2 mL) at 50° C. Upon completion of addition, the reaction mixture was stirred at 50° C. for 1 h. The reaction mixture was diluted with H$_2$O (10 mL) and filtered. The resulting solid filter cake was washed with small volume of DCM and dried under reduced pressure to afford the crude product. The crude product was subsequently acidified with 0.5M HCl (aq) and concentrated to dryness to afford the title compound (1) (100 mg, 81.1% yield) as a white solid. The structure was confirmed by LCMS and $^1$H-NMR. TLC: R$_f$=0.6 (silica gel; DCM/MeOH=20/1, v/v). LCMS (Agilent): Rt=0.86 min; m/z calculated for [M+H]$^+$ 345.1, found 345.1. $^1$H-NMR (400 MHz, DMSO-d$_6$) δ 10.95 (s, 1H), 10.51 (s, 1H), 8.1 (d, J=8.4 Hz, 2H), 7.86 (d, J=8.4 Hz, 2H), 7.63-7.60 (m, 4H), 4.33 (d, J=5.2 Hz, 2H), 3.81-3.86 (m, 2H), 3.64-3.75 (m, 2H), 3.41-3.46 (m, 1H), 3.29-3.45 (m, 1H), 3.08-3.21 (m, 2H), 2.29-3.32 (m, 1H), 1.96-2.03 (m, 1H).

Example 2

Synthesis of N-(4-((2-oxa-6-azaspiro[3.3]heptan-6-yl)methyl)phenyl)-4-chlorobenzamide (2)

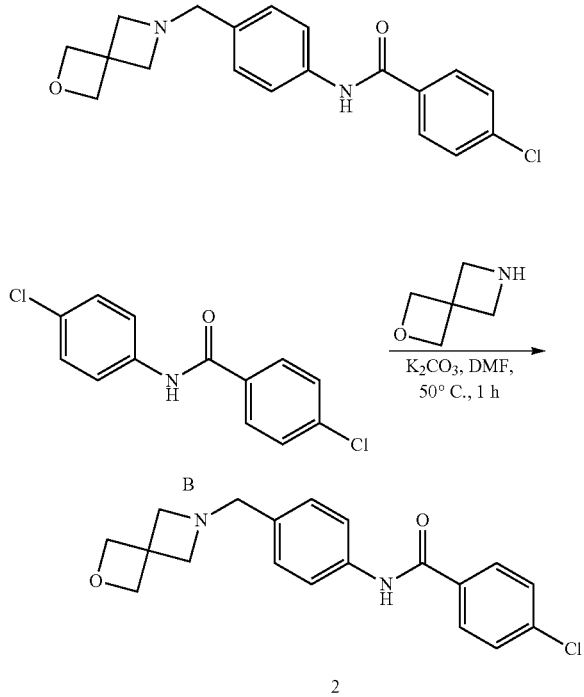

Anhydrous potassium carbonate (197.39 mg, 1.428 mmol) was added in one lot to a stirred mixture of compound (B) (200 mg, 0.714 mmol) and 2-oxa-6-azaspiro[3.3]heptane (84.95 mg, 0.857 mmol) in DMF (4 mL) at room temperature, and the heated to 50° C. After stirring at 50° C. for 2 h, the reaction mixture was diluted with H$_2$O (10 mL) and filtered. The collected solid was purified by preparative C18 reverse phase HPLC (eluting with 10% to 95% MeCN/H$_2$O) to afford the title compound (2) (109 mg, 44.5% yield) as a white solid. The structure was confirmed by LCMS and $^1$H-NMR. TLC: R$_f$=0.2 (silica gel; MeOH:DCM=1:10). LCMS (Agilent): Rt=0.81 min; m/z calculated for [M+H]$^+$ 343.1, found 343.1. $^1$H-NMR (400 MHz, DMSO-d$_6$) δ 10.40 (s, 1H), 8.01-7.97 (m, 2H), 7.77 (d, J=8.4 Hz, 2H), 7.63-7.59 (m, 2H), 7.35 (d, J=8 Hz, 2H), 4.63 (s, 4H), 3.85 (d, J=42.4 Hz, 4H), 3.33 (s, 2H).

Example 3

Synthesis of 2-chloro-N-(4-(morpholinomethyl)phenyl)pyrimidine-5-carboxamide (3)

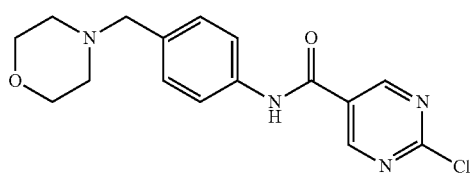 [SMILES: O=C(Nc1ccc(CN2CCOCC2)cc1)c1cnc(Cl)nc1]

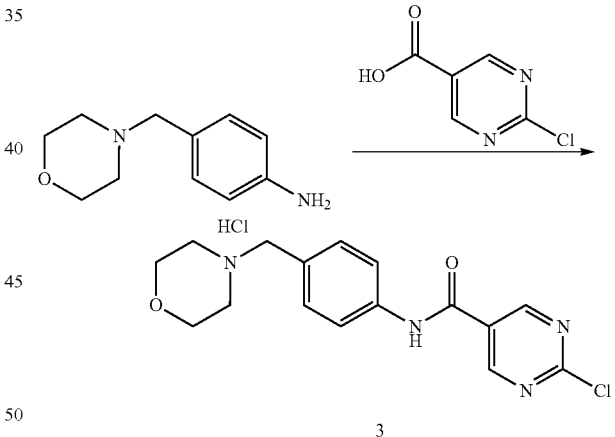

3

EEDQ (257 mg, 1.0 mmol) was added in one lot to a stirred solution of 4-(morpholinomethyl)aniline (200 mg, 1.0 mmol) and 2-chloropyrimidine-5-carboxylic acid (164 mg, 1.0 mmol) in DMF (4 mL) at room temperature. Upon completion of addition, the reaction mixture was stirred at room temperature for 40 hours and diluted with H$_2$O (10 mL). The resulting slurry was extracted with EtOAc (30 mL×3) and concentrated under reduced pressure to dryness. The resulting residue was purified by preparative C18 reverse phase-HPLC to afford the title compound (3) (130 mg, 37.6% yield) as a white solid. The structure was confirmed by LCMS and $^1$H-NMR. TLC: R$_f$=0.3 (silica gel, MeOH/DCM=1/15, v/v). LCMS (Agilent): Rt=0.49 min; m/z calculated for [M+Na]+333.1, found 333.0. $^1$H-NMR (400 MHz, DMSO-d$_6$) δ 11.06 (s, 1H), 10.92 (s, 1H), 9.27

(s, 2H), 7.88-7.81 (m, 2H), 7.61 (d, J=8.3 Hz, 2H), 4.30 (d, J=5.1 Hz, 2H), 3.94 (dd, J=13.0, 3.3 Hz, 2H), 3.78 (t, J=12.0 Hz, 2H), 3.22 (d, J=12.4 Hz, 2H), 3.07 (d, J=11.5 Hz, 2H).

Example 4

Synthesis of N-(4-((7-oxa-2-azaspiro[3.5]nonan-2-yl)methyl)phenyl)-4-chlorobenzamide (4)

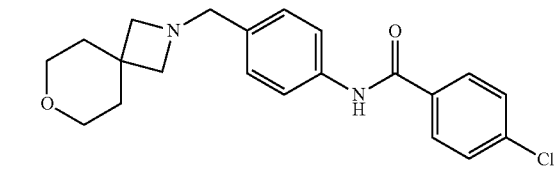 [SMILES: O=C(Nc1ccc(CN2CC3(CCOCC3)C2)cc1)c1ccc(Cl)cc1]

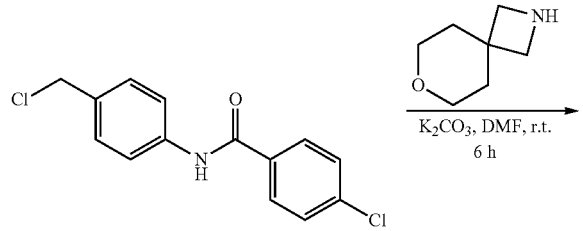
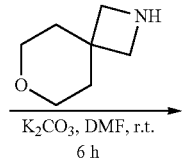

B

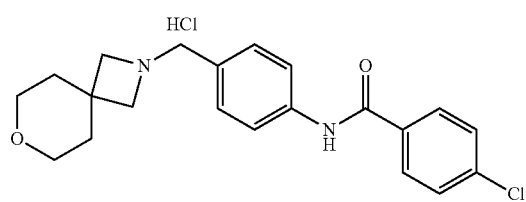

4

Anhydrous potassium carbonate (621 mg, 4.49 mmol) was added to a stirred solution of compound (A) (430 mg, 1.5 mmol) and 7-oxa-2-azaspiro[3.5]nonane (191 mg, 1.5 mmol) in DMF (5 mL) at room temperature. After stirring at room temperature for 6 h, the reaction mixture was diluted with H$_2$O (10 mL) and filtered. The resulting solid was dissolved with 2N HCl (2 mL) and DMSO (2 mL), and subsequently purified by reverse phase Biotage® column chromatography (C18 column, eluting with 10% to 95% MeCN/H$_2$O containing 0.1% hydrochloric acid) to afford the title compound (4) (80 mg, 14.4% yield) as a white solid. The structure was confirmed by LCMS and $^1$H-NMR. TLC: R$_f$=0.40 (silica gel, PE:EtOAc=1:1, v/v). LCMS (Agilent): Rt=2.00 min; m/z calculated for [M+H]$^+$ 371.2, found 371.2. $^1$H-NMR (400 MHz, DMSO-d$_6$) δ 10.43 (s, 1H), 7.99 (d, J=8.6 Hz, 2H), 7.80 (d, J=8.5 Hz, 2H), 7.62 (d, J=8.6 Hz, 2H), 7.50 (s, 2H), 4.19 (s, 2H), 3.69 (s, 4H), 3.48 (s, 4H), 1.77 (s, 4H).

Example 5

Synthesis of N-(4-((8-oxa-2-azaspiro[4.5]decan-2-yl)methyl)phenyl-4-chlorobenzamide (5)

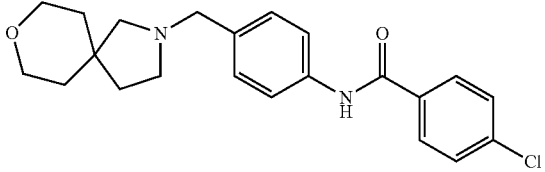 [SMILES: O=C(Nc1ccc(CN2CCC3(CCOCC3)C2)cc1)c1ccc(Cl)cc1]

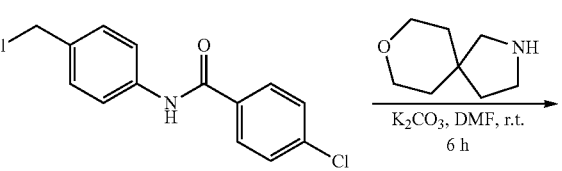
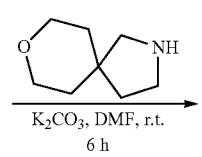

B

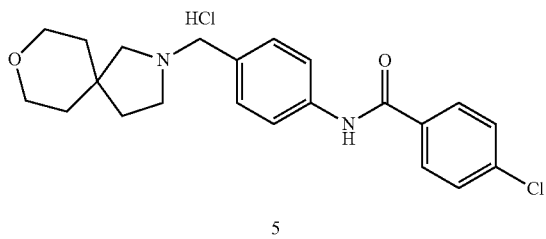

5

Anhydrous potassium carbonate (230 mg, 1.66 mmol) was added in one lot to a stirred solution of compound (B) (280 mg, 0.83 mmol) and 8-oxa-2-azaspiro[4.5]decane (142 mg, 1.0 mmol) in DMF (6 mL) at room temperature. After stirring at room temperature for 6 h, the reaction mixture was diluted with H$_2$O (10 mL) and filtered. The resulting filter cake was washed with small volume of DCM and dried under reduced pressure. The residue was subsequently purified by silica gel column (DCM/MeOH=50/1, v/v). The key fractions were concentrated under reduced pressure and the resulting solid was treated with 0.5N HCl (aq) and evaporated to dryness under reduced pressure to afford the title compound (5) (144.2 mg, 45.1% yield) as a white solid. The structure was confirmed by LCMS and $^1$H-NMR. TLC: R$_f$=0.4 silica gel; DCM:MeOH=20:1. LCMS (Agilent): Rt=1.96 min; m/z calculated for [M+H]$^+$ 385.1, find 385.1. $^1$H-NMR (400 MHz, DMSO-d$_6$) δ 11.37 (s, 1H), 10.51 (s, 1H), 8.01 (d, J=8.4 Hz, 2H), 7.84 (d, J=8.8 Hz, 2H), 7.63-7.60 (m, 4H), 4.35-4.25 (m, 2H), 3.58-3.47 (m, 4H), 4.45-3.37 (m, 1H), 3.25-3.14 (m, 2H), 2.95-2.89 (m, 1H), 2.01-1.95 (m, 1H), 1.91-1.84 (m, 1H), 1.67-1.80 (m, 3H), 1.55-1.50 (m, 1H).

Example 6

Synthesis of N-(4-((1-oxa-7-azaspiro[4.4]nonan-7-yl)methyl)phenyl)-4-chlorobenzamide (6)

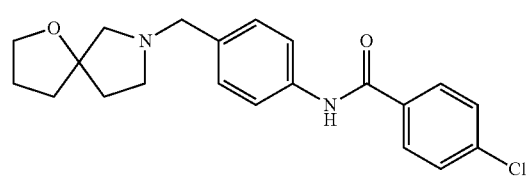 [SMILES: O=C(Nc1ccc(CN2CCC3(CCCO3)C2)cc1)c1ccc(Cl)cc1]

Examples 7 and 8

Synthesis of 4-chloro-N-(4-(((2S,6R)-2,6-dimethylmorpholino)methyl)phenyl)benzamide (7)

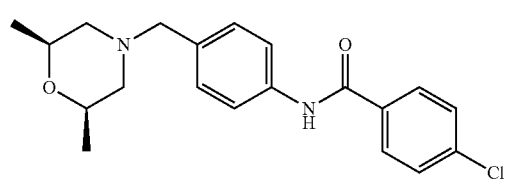 [SMILES: C[C@@H]1CN(Cc2ccc(NC(=O)c3ccc(Cl)cc3)cc2)C[C@H](C)O1]

Synthesis of 4-chloro-N-(4-(((2S,6S)-2,6-dimethylmorpholino)methyl)phenyl)benzamide (8)

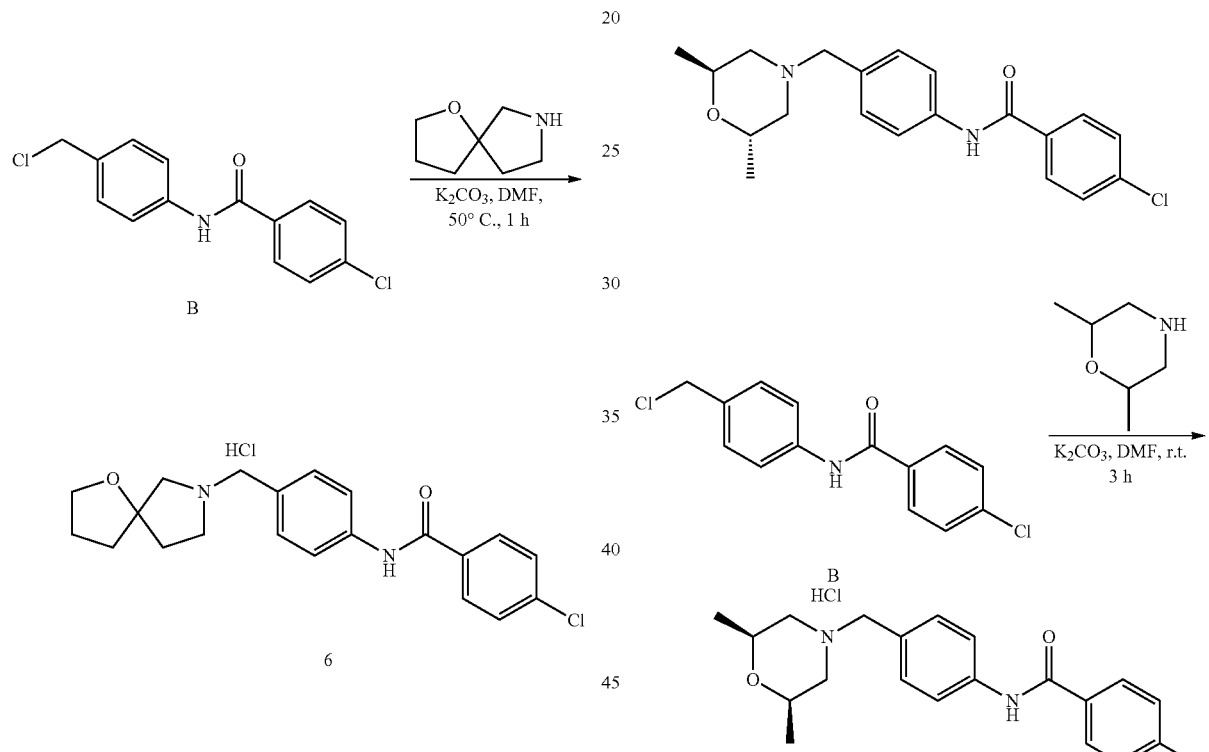

Anhydrous potassium carbonate (444 mg, 3.21 mmol) was added in one lot to a solution of compound (B) (300 mg, 1.07 mmol) and 1-oxa-7-azaspiro[4.4]nonane (210 mg, 1.28 mmol) in DMF (5.6 mL) at 50° C. After stirring at 50° C. for 1 h, the reaction mixture was diluted with H$_2$O (20 mL) and filtered. The resulting filter cake was washed with small volume of DCM and dried under reduced pressure. The residue was purified by silica gel column chromatography (DCM/MeOH=50/1, v/v), and the desired fractions were evaporated under reduced pressure. The resulting residue was acidified with 0.5M HCl (aq) and concentrated under reduced pressure to afford the title compound (6) (100 mg, 25.2% yield) as a white solid. The structure was confirmed by LCMS and $^1$H-NMR. LCMS (Agilent): Rt=1.93 min; m/z calculated for [M+H]$^+$=371.1, find [M+H]$^+$=371.1. $^1$H-NMR (400 MHz, DMSO-d$_6$) δ 10.55 (d, J=13.6 Hz, 1H), 8.01-8.04 (m, 2H), 7.87-7.83 (m, 2H), 7.62-7.57 (m, 4H), 4.34-4.26 (m, 2H), 3.80-3.68 (m, 2H), 3.47-3.08 (m, 4H), 2.02-1.86 (m, 6H).

Anhydrous potassium carbonate (296 mg, 2.14 mmol) was added in one lot to a stirred solution of compound (B) (300 mg, 1.07 mmol) and 2,6-dimethylmorpholine (147 mg, 1.28 mmol) in DMF (5 mL) at 50° C. After stirring at 50° C. for 1 h, the reaction mixture was diluted with H$_2$O (20 mL) and extracted with EtOAc (30 mL×4). The combined extracts were concentrated to dryness. The residue was purified by C18 reverse phase preparative-HPLC (eluting with 10% to 95% MeCN/H$_2$O). The key fractions were concentrated under reduced pressure and the resulting solid was treated with 0.5N HCl (aq) and evaporated to dryness under reduced pressure to afford the cis isomer (7) (105 mg, 27.3%) and the trans isomer (8) (40 mg, 10.4%). The structure was confirmed by LCMS and $^1$H-NMR.

Cis Isomer (7). TLC: R$_f$=0.4 silica gel; neat EtOAc. LCMS (Agilent): Rt=1.92 min; m/z calculated for

[M+H]⁺=359.1, find [M+H]⁺=359.1. ¹H-NMR (400 MHz, DMSO-d₆) δ 10.50 (s, 1H), 8.02-7.99 (m, 2H), 7.87-7.85 (m, 2H), 7.63-7.58 (m, 4H), 4.26-4.25 (m, 2H), 4.02-3.98 (m, 2H), 3.23-3.20 (m, 2H), 2.66-2.58 (m, 2H), 1.11 (d, J=6.0 Hz, 6H).

Trans isomer (8). TLC: R_f=0.5 silica gel; neat EtOAc. LCMS (Agilent): Rt=1.92 min; m/z calculated for [M+H]⁺=359.1, find [M+H]⁺=359.1. ¹H-NMR (400 MHz, DMSO-d₆) δ 10.95 (s, 1H), 10.52 (s, 1H), 8.01-7.99 (m, 2H), 7.87-7.85 (m, 2H), 7.64-7.61 (m, 4H), 4.34-4.12 (m, 4H), 3.28-3.25 (m, 1H), 3.08-2.93 (m, 2H), 2.67-2.59 (m, 1H), 1.40 (d, J=6.8 Hz, 3H), 1.09 (d, J=6.0 Hz, 3H).

Example 9

Synthesis of N-(4-(((1R,5S)-3-oxa-7-azabicyclo[3.3.1]nonan-7-yl)methyl)phenyl)-4-chlorobenzamide (9)

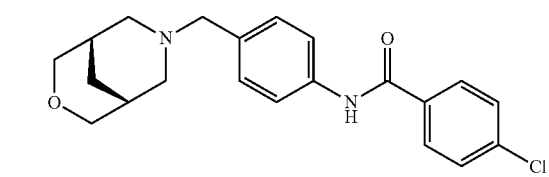 [SMILES: O=C(Nc1ccc(CN2C[C@@H]3COC[C@@H](C3)C2)cc1)c1ccc(Cl)cc1]

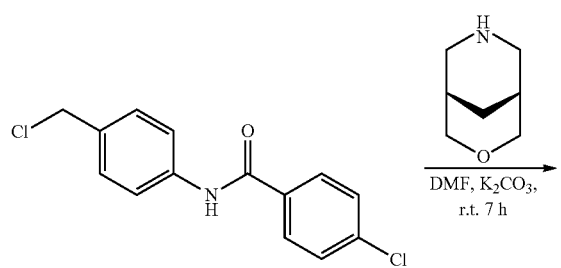

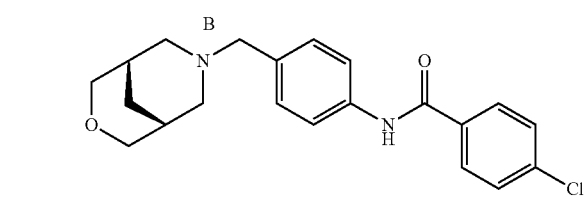

Anhydrous potassium carbonate (625 mg, 4.52 mmol) was added in one lot to a stirred solution of compound (B) (512 mg, 1.81 mmol) and 3-oxa-7-azabicyclo[3.3.1]nonane (230 mg, 1.81 mmol) in DMF (6 mL) at room temperature. After stirring at room temperature for 7 h, the reaction mixture was treated with H₂O (30 mL) and filtered. The resulting filter cake was washed with small volume of DCM and dried under reduced pressure. The residue was acidified with 0.5N HCl (aq) and concentrated to dryness to afford the title compound (9) (437 mg, 78.2% yield) as a white solid. The structure was confirmed by LCMS and ¹H-NMR. TLC: R_f=0.4 silica gel; PE:EtOAc=1:1. LCMS (Shimadzu): Rt=2.32 min; m/z calculated for [M+H]⁺=371.2, find [M+H]⁺=371.2. ¹H-NMR (400 MHz, DMSO-d₆) δ 10.58 (s, 1H), 8.65 (s, 1H), 8.04-8.00 (m, 2H), 7.92-7.88 (m, 2H), 7.64-7.57 (m, 4H), 4.22 (d, J=5.3 Hz, 2H), 3.97 (d, J=11.3 Hz, 2H), 3.69-3.64 (m, 2H), 3.48-3.42 (m, 2H), 3.27 (t, J=11.2 Hz, 2H), 2.01 (s, 2H), 1.94-1.78 (m, 2H).

Example 10

Synthesis of 4-chloro-N-(4-(((3aR,6aS)-tetrahydro-1H-furo[3,4-c]pyrrol-5(3H)—1)methyl)phenyl)benzamide (10)

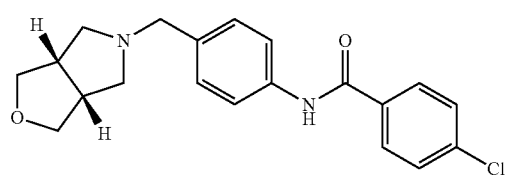 [SMILES: O=C(Nc1ccc(CN2C[C@H]3COC[C@H]3C2)cc1)c1ccc(Cl)cc1]

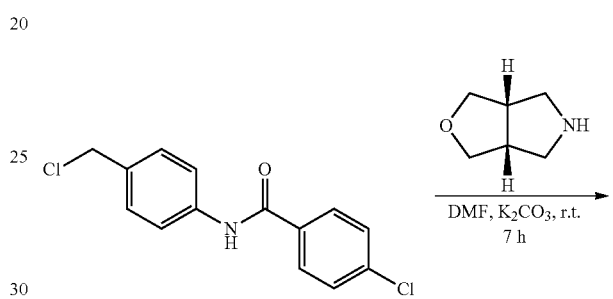

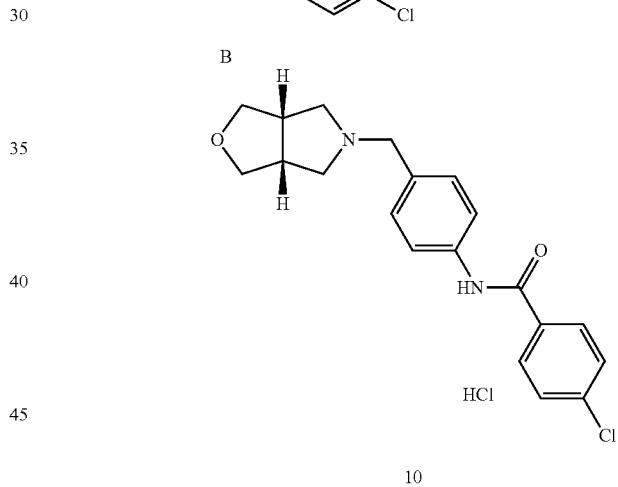

Anhydrous potassium carbonate (531 mg, 3.84 mmol) was added in one lot to a stirred solution of compound (B) (435 mg, 1.28 mmol) and (3aR,6aS)-hexahydro-1H-furo[3,4-c]pyrrole (230 mg, 1.54 mmol) in DMF (6.5 mL) at room temperature. The reaction mixture was stirred at room temperature for 7 h. The reaction mixture was treated with H₂O (60 mL), filtered, the resulting solid was washed with petroleum ether/ethyl acetate=3/1 and purified by C18 reverse phase preparative-HPLC (eluting with 10% to 95% MeCN/H₂O). The key fractions were concentrated under reduced pressure and the resulting solid was treated with 0.5N HCl (aq) and evaporated to dryness under reduced pressure to afford the title compound (10) (194.5 mg, 42.6% yield) as a white solid. The structure was confirmed by LCMS and ¹H-NMR. TLC: R_f=0.30 (silica gel, DCM/MeOH=20/1, v/v). LCMS (Shimadzu): Rt=2.25 min; m/z calculated for [M+H]⁺=357.2, find [M+H]⁺=357.2. ¹H-NMR (400 MHz, DMSO-d₆) δ 10.95 (d, J=78.2 Hz, 1H), 10.51 (d, J=6.3 Hz, 1H), 8.04-7.98 (m, 2H), 7.85 (dd, J=8.5, 6.2 Hz, 2H), 7.65-7.52 (m, 4H), 4.28 (dd, J=21.3, 5.6 Hz, 2H), 3.75 (t, J=9.5 Hz, 2H), 3.67-3.55 (m, 2H), 3.37 (ddd, J=38.9, 11.0, 5.8 Hz, 2H), 3.20-2.91 (m, 3H), 2.73-2.67 (m, 1H).

Example 11

Synthesis of 4-chloro-N-(4-((4-hydroxypiperidin-1-yl)methyl)phenyl)benzamide (11)

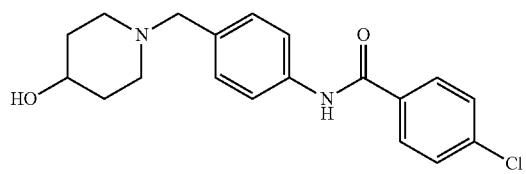 [SMILES: O=C(Nc1ccc(CN2CCC(O)CC2)cc1)c1ccc(Cl)cc1]

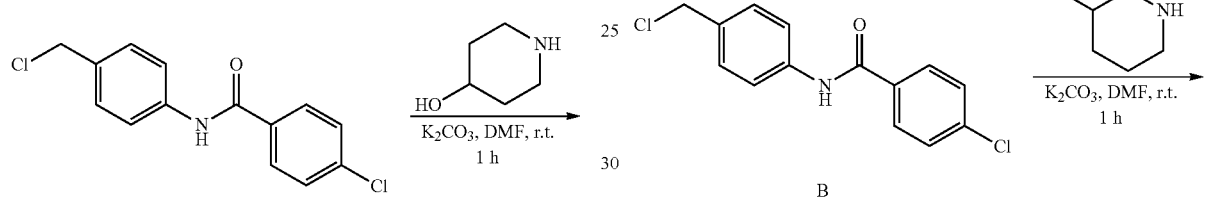

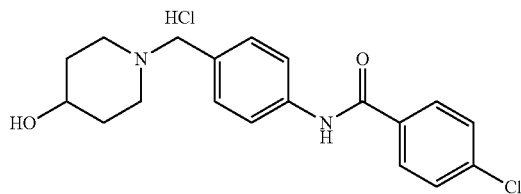

11

Anhydrous potassium carbonate (50.2 mg, 0.363 mmol) was added in one lot to a stirred solution of compound (B) (100.0 mg, 0.29 mmol) and piperidin-4-ol (35.4 mg, 0.35 mmol) in DMF (2 mL) at room temperature. After stirring at room temperature for 1 h, the reaction mixture was diluted with H$_2$O (10 mL) and filtered. The resulting filter cake was washed with small volume of DCM and dried under reduced pressure to afford crude product. The crude product was acidified by 0.5M HCl and subsequently concentrated at reduced pressure to afford the title compound (11) (90 mg, 90.0% yield) as a white solid. The structure was confirmed by LCMS and $^1$H-NMR. TLC: R$_f$=0.1 silica gel; DCM:MeOH=10:1. LCMS (Agilent): Rt=1.72 min; m/z calculated for [M+H]$^+$=345.1, find [M+H]$^+$=345.1. $^1$H-NMR (400 MHz, DMSO-d$_6$) δ 10.76 (s, 1H), 10.54 (s, 1H), 8.02 (d, J=8.4 Hz, 2H), 7.84 (d, $^1$H-NMR=8.8 Hz, 2H), 7.60 (m, J=4.5 Hz, 4H), 4.22 (m, J=5.2 Hz, 2H), 3.92 (s, 1H), 3.61 (m, J=5.6 Hz, 1H), 3.26 (d, J=12.4 Hz, 1H), 3.08 (m, J=6.8 Hz, 2H), 2.89 (m, J=8.2 Hz, 1H), 1.95 (m, J=14.0 Hz, 2H), 1.73 (m, J=14.0 Hz, 2H).

Example 12

Synthesis of 4-chloro-N-(4-((3-hydroxypiperidin-1-yl)methyl)phenyl)benzamide (12)

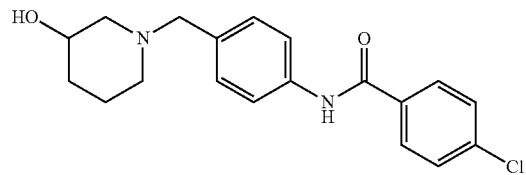 [SMILES: O=C(Nc1ccc(CN2CCCC(O)C2)cc1)c1ccc(Cl)cc1]

4-chloro-N-(4-((3-hydroxypiperidin-1-yl)methyl)phenyl)benzamide

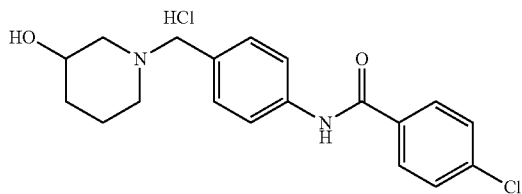

12

Anhydrous potassium carbonate (160.4 mg, 1.16 mmol) was added in one lot to a stirred solution of compound (B) (200 mg, 0.58 mmol) and piperidin-3-ol (70.8 mg, 0.70 mmol) in DMF (4 mL) at room temperature. After stirring at room temperature for 1 h, the reaction mixture was diluted with H$_2$O (20 mL) and filtered. The resulting filter cake was washed with small volume of DCM and dried under reduced pressure to afford crude product. The crude product was acidified by 0.5M HCl (aq) and concentrated to dryness under reduced pressure to afford the title compound (12) (122.5 mg, 61.25% yield) as a white solid. The structure was confirmed by LCMS and $^1$H-NMR. TLC: R$_f$=0.2 silica gel; DCM:MeOH=10:1. LCMS (Agilent): Rt=1.77 min; m/z calculated for [M+H]$^+$=345.1, find [M+H]$^+$=345.1. $^1$H-NMR (400 MHz, DMSO-d$_6$) δ 10.99 (s, 0.57H), 10.55 (d, J=11.6 Hz, 1H), 9.59 (s, 0.35H), 8.04-8.00 (m, 2H), 7.88-7.85 (m, 2H), 7.64-7.52 (m, 4H), 4.30-4.12 (m, 2H), 4.01 (s, 0.39H), 3.86 (s, 0.59H), 3.34-3.16 (m, 2H), 3.00-2.87 (m, 1H), 2.72 (s, 0.69H), 2.08-2.01 (m, 0.47H), 1.92-1.81 (m, 2H), 1.69-1.51 (m, 1H), 1.28-1.18 (m, 1H).

Example 13

Synthesis of 4-chloro-N-(4-((3-hydroxypyrrolidin-1-yl)methyl)phenyl)benzamide (13)

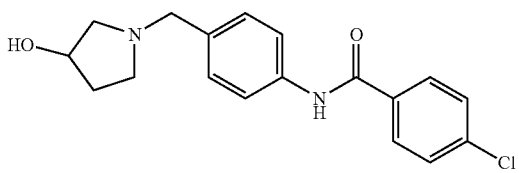 [SMILES: O=C(Nc1ccc(CN2CCC(O)C2)cc1)c1ccc(Cl)cc1]

4-chloro-N-(4-((3-hydroxypyrrolidin-1-yl)methyl)phenyl)benzamide

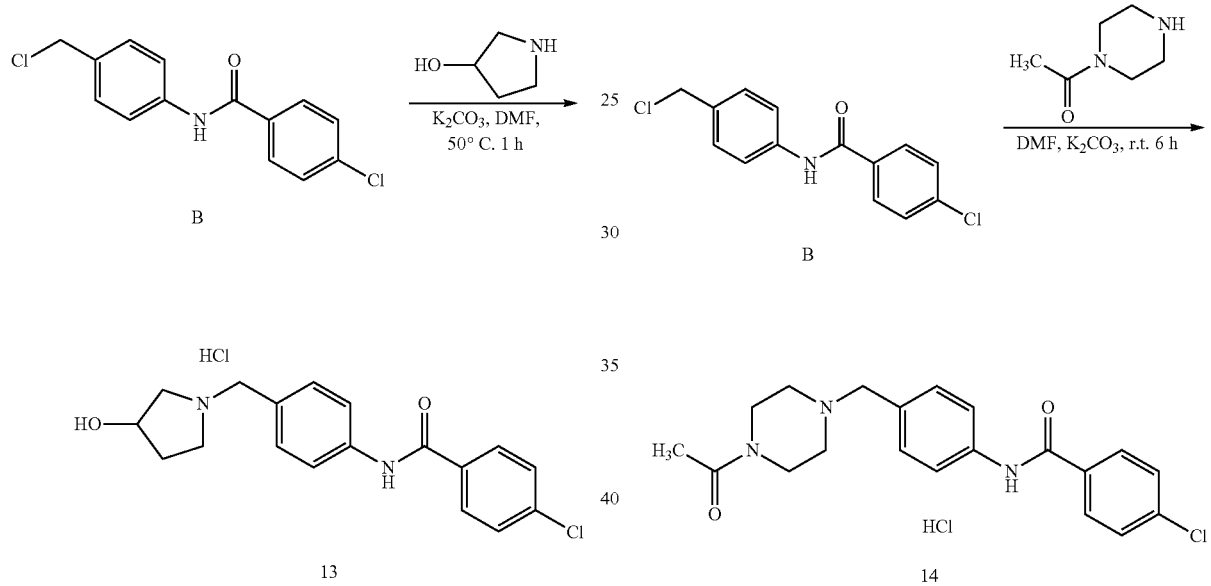

Anhydrous potassium carbonate (197.4 mg, 1.428 mmol) was added in one lot to a stirred solution of compound (B) (200 mg, 0.72 mmol) and pyrrolidin-3-ol (74.6 mg, 0.86 mmol) in DMF (4 mL) at room temperature. After stirring at 50° C. for 6 hours, the reaction mixture was diluted with H$_2$O (20 mL) and filtered. The resulting filter cake was washed with small volume of DCM and dried under reduced pressure to afford crude product. The crude product was acidified by 0.5M HCl (aq) and concentrated to dryness under reduced pressure to afford the title compound (13) (230 mg, 87.71% yield) as a white solid. The structure was confirmed by LCMS and $^1$H-NMR. TLC: R$_f$=0.25 silica gel; DCM:MeOH=10:1. LCMS (Agilent): Rt=1.82 min; m/z calculated for [M+H]$^+$=333.1, find [M+H]$^+$=333.1. $^1$H-NMR (400 MHz, DMSO-d$_6$) δ 11.79 (s, 0.45H), 10.78 (s, 0.40H), 10.51 (d, J=7.6 Hz, 1H), 8.02-7.99 (m, 2H), 7.86-7.93 (m, 2H), 7.63-7.55 (m, 4H), 4.45-4.24 (m, 3H), 3.50-3.44 (m, 1H), 3.40-3.33 (m, 0.52H), 3.27-3.09 (m, 2H), 2.98-2.93 (m, 0.50H), 2.33-2.23 (m, 0.44H), 2.07-1.81 (m, 1.61H).

Example 14

Synthesis of N-(4-((4-acetylpiperazin-1-yl)methyl)phenyl)-4-chlorobenzamide (14)

Anhydrous potassium carbonate (414 mg, 2.99 mmol) was added in one lot to a stirred solution of compound (B) (340 mg, 1.0 mmol) and 1-(piperazin-1-yl)ethan-1-one (128 mg, 1.0 mmol) in DMF (4 mL) at room temperature. After stirring at room temperature for 6 h, the reaction mixture was diluted with H$_2$O (20 mL) and filtered. The resulting solid was dissolved by 2N HCl (2 mL) and DMSO (2 mL), and purified by reverse phase Biotage® chromatography (C18 column, eluting with 10% to 95% MeCN/H$_2$O containing 0.1% hydrochloric acid) to afford the title compound (14) (130 mg, 35.0% yield) as a white solid. The structure was confirmed by LCMS and $^1$H-NMR. TLC: R$_f$=0.4 silica gel; DCM:MeOH=10:1. LCMS (Agilent): Rt=0.87 min; m/z calculated for [M+H]$^+$=372.0, find [M+H]$^+$=372.0. $^1$H-NMR (400 MHz, DMSO-d$_6$) δ 11.58 (s, 1H), 10.55 (s, 1H), 8.05-7.98 (m, 2H), 7.87 (d, J=8.5 Hz, 2H), 7.60 (t, J=8.8 Hz, 4H), 4.41 (d, J=14.1 Hz, 1H), 4.27 (d, J=4.3 Hz, 2H), 3.98 (d, J=14.4 Hz, 1H), 3.59 (t, J=13.3 Hz, 1H), 3.28 (d, J=12.1 Hz, 2H), 3.06 (dt, J=20.9, 12.0 Hz, 2H), 2.87 (d, J=11.6 Hz, 1H), 2.03 (s, 3H).

Example 15

Synthesis of 4-chloro-N-(4-((3-oxopiperazin-1-yl)methyl)phenyl)benzamide (15)

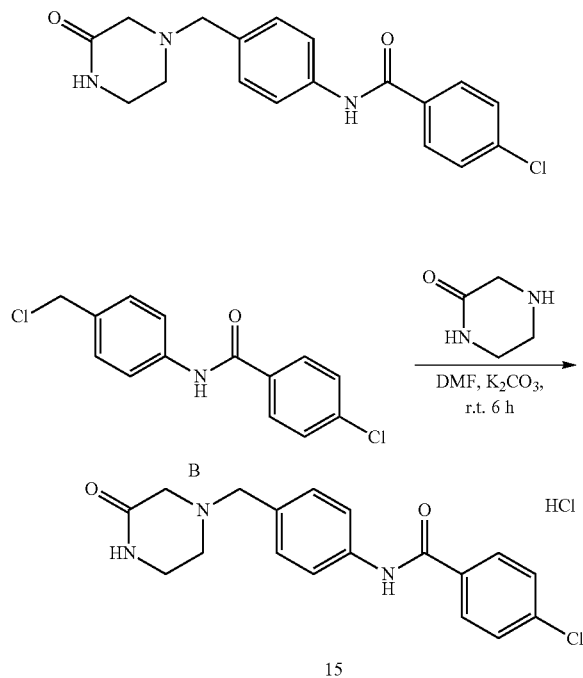

Anhydrous potassium carbonate (414 mg, 2.88 mmol) was added in one lot to a stirred solution of compound (B) (280 mg, 1.0 mmol) and piperazin-2-one (100 mg, 1.0 mmol) in DMF (4 mL) room temperature. After stirring at room temperature for 6 h, the reaction mixture was diluted with H$_2$O (20 mL) and filtered. The resulting solid was dissolved using 2N HCl (2 mL) and DMSO (2 mL), and subsequently purified by Biotage® reverse phase column chromatography (C18 column, eluting with 10% to 95% MeCN/H$_2$O containing 0.1% hydrochloric acid) to afford the title compound (15) (108 mg, 31.5% yield) as a white solid. The structure was confirmed by LCMS and $^1$H-NMR. TLC: R$_f$=0.3 silica gel; PE:EtOAc=1:1. LCMS (Agilent): Rt=0.85 min; m/z calculated for [M+H]$^+$=344.1, find [M+H]$^+$=344.1. $^1$H-NMR (400 MHz, DMSO-d$_6$) δ 11.93 (s, 1H), 10.55 (s, 1H), 8.39 (s, 1H), 8.06-7.98 (m, 2H), 7.92-7.83 (m, 2H), 7.61 (dd, J=8.4, 6.0 Hz, 4H), 4.34 (s, 2H), 3.78-3.40 (m, 5H), 3.19 (d, J=21.8 Hz, 1H).

Example 16

Synthesis of 4-chloro-N-(4-((4-methyl-3-oxopiperazin-1-yl)methyl)phenyl)benzamide (16)

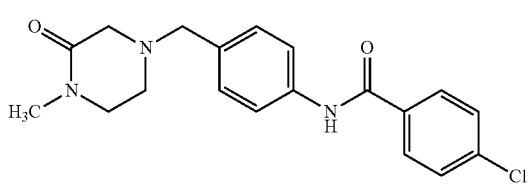 [SMILES: CN1CCN(Cc2ccc(NC(=O)c3ccc(Cl)cc3)cc2)CC1=O]

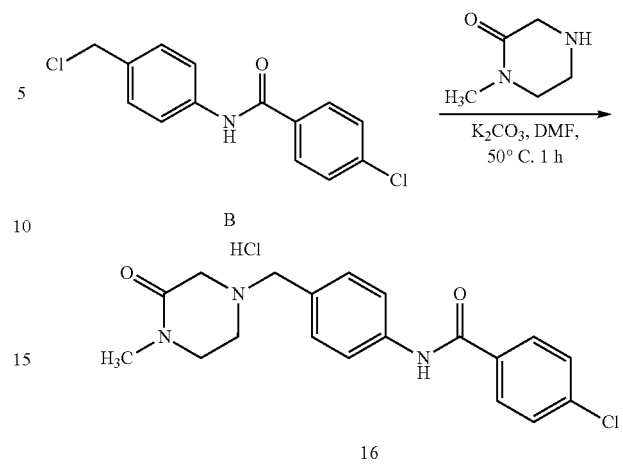

Anhydrous potassium (296 mg, 2.14 mmol) was added in one lot to a stirred solution of compound (B) (300 mg, 1.07 mmol) and 1-methylpiperazin-2-one (146 mg, 1.28 mmol) in DMF (5 mL) at 50° C. After stirring at 50° C. for 1 h, the reaction mixture was diluted with H$_2$O (10 mL) and filtered. The resulting filter cake was washed with small volume of DCM and dried under pressure to afford crude product. The crude product was acidified by 0.5M HCl and concentrated to dryness under reduced pressure to afford the title compound (16) (121 mg, 31.6% yield) as a white solid. The structure was confirmed by LCMS and $^1$H-NMR. TLC: R$_f$=0.4 silica gel; DCM:MeOH=20:1. LCMS (Agilent): Rt=1.81 min; m/z calculated for [M+H]$^+$=358.1, find [M+H]$^+$=358.1. $^1$H-NMR (400 MHz, DMSO-d$_6$) δ 10.36 (s, 1H), 8.01-7.99 (m, 2H), 7.75 (d, J=8.0 Hz, 2H), 7.62-7.59 (m, 2H), 7.30-7.28 (m, 2H), 3.50 (s, 1H), 3.25 (t, J=5.6 Hz, 2H), 2.94 (s, 2H), 2.81 (s, 3H), 2.83-2.62 (m, 2H).

Example 17

Synthesis of 4-chloro-N-(4-((4-methylpiperazin-1-yl)methyl)phenyl)benzamide (17)

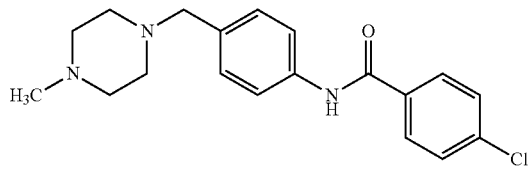 [SMILES: CN1CCN(Cc2ccc(NC(=O)c3ccc(Cl)cc3)cc2)CC1]

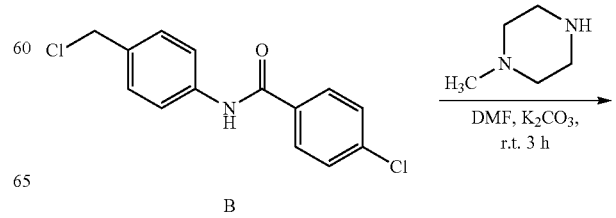

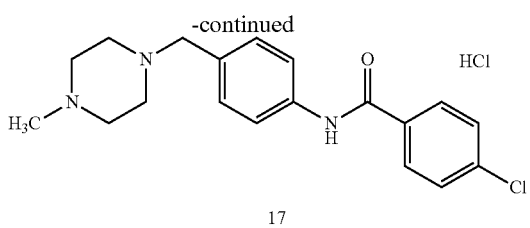

17

Anhydrous potassium carbonate (290 mg, 2.1 mmol) was added in one lot to a stirred solution of compound (B) (200 mg, 0.7 mmol) and 1-methylpiperazine (74 mg, 0.7 mmol) in DMF (4 mL) at room temperature. After stirring at room temperature for 3 h, the reaction mixture was diluted with H$_2$O (10 mL) and filtered. The resulting filter cake was purified by C18 reverse phase preparative HPLC, (eluting with 10% to 95% MeCN/H$_2$O containing 0.1% hydrochloric acid) to afford the title compound (17) (110 mg, 43.4% yield) as a white solid. The structure was confirmed by LCMS and $^1$H-NMR. TLC: R$_f$=0.3 silica gel; MeOH: DCM=1:15. LCMS (Agilent): Rt=0.83 min; m/z calculated for [M+H]$^+$=344.1, find [M+H]$^+$=344.1. $^1$H-NMR (400 MHz, DMSO-d$_6$) δ 10.39 (s, 1H), 8.03-7.95 (m, 2H), 7.80 (d, J=8.5 Hz, 2H), 7.66-7.56 (m, 2H), 7.38 (d, J=8.3 Hz, 2H), 5.75 (s, 2H), 3.91 (s, 2H), 3.29 (d, J=97.6 Hz, 6H), 2.80 (s, 3H).

Example 18

Expression and Purification Pf p38 MAPK Proteins

Human p38α and β MAP kinase isoforms will be expressed in *E. coli* and purified using protocols described in Shah et al., *Journal of Immunology*, 2017, 198, 3296-3306.

Mouse anti-human p38α and rabbit anti-phospho-MK2 (T222) and phospho-STAT-1 (S727) are obtained from Cell Signaling Technologies (Danvers, Mass.). The coding sequences for human p38α variant 2 and p38β (with N-terminal hemagglutinin tag) are amplified by PCR and cloned into pRSetA (Thermo Fisher Scientific, Waltham, Mass.). Mutations are introduced into p38α using Quikchange® (Stratagene) and are confirmed by bidirectional sequencing. To generate activated dual-phosphorylated p38α for in vitro kinase assays, p38α variant 2 is amplified by PCR and cloned into a first multicloning site of pETDuet™ (EMD-Millipore) in-frame with an N-terminal His tag sequence. A gene block containing the optimized sequence for the constitutively active human MKK6 S207G/T211G mutant is synthesized (Genscript, Piscataway, N.J.) and cloned into the second multicloning site of pETDuet™-p38α. Plasmids are transformed in *Escherichia coli* BL21 and proteins are purified using cobalt columns (TALON; Clontech Laboratories, Mountain View, Calif.), and confirmed by SDS-PAGE and immunoblotting. The p38α protein expressed from the pETDuet™ plasmid is confirmed to be about 80% dual-phosphorylated as determined by MALDI.

Example 19

Differential Scanning Fluorimetry (DSF) Assays

Binding of certain compounds of Formula (1) to p38α MAPK and p38β MAPK isoforms was evaluated using differential scanning fluorimetry (DSF), which evaluates changes in the target protein melting temperature (ΔT$_m$) due to interactions with a test compound. SYPRO orange (Thermo Fischer Scientific) diluted 1:1000 in 10 mM HEPES, 150 mM NaCl (pH 7.5), and 1 µM unphosphorylated recombinant human p38α were added to 96-well PCR plates. Test compounds (50 nm to 200 nM) dissolved in 100% DMSO (2% final DMSO concentration) were added, the plates mixed, sealed, centrifuged at 1,000 rpm for 1 min, and melting curves determined using an Applied Biosystems StepOne™ real-time PCR instrument. The melting point is determined from the first derivative curve.

All compounds were tested at 100 µM initially for interactions with p38α or p38β by DSF. Control ATP-competitive p38 inhibitors were tested at 10 µM. The compounds that showed selectivity for p38α were then re-tested for dose response (1, 3, 10, 30, 100 µM). Each compound was tested in 3 technical replicates per experiment and each experiment was repeated 3 times.

Compounds 1, 6, 8, and 14 exhibited a ΔTm greater than 0.1 at a concentration of 100 µM. SB203580 exhibited a ΔTm greater than 10 at a concentration of 10 µM.

Example 20

Surface Plasmon Resonance (SPR) Assays

The compounds that showed selectivity for p38α in DSF assays was tested for binding affinity by SPR using a Biacore T200 instrument. Binding affinity (K$_D$) to p38α or p38β was determined from the association and dissociation curves generated at various doses of test compound (e. g. 1, 3, 10, 30, 100 µM). Controls were used to confirm binding of ATP-competitive p38 inhibitors. Each experiment will be repeated 3 times.

Compounds (1), (6), (8), and (14) exhibited a K$_D$ of less than 1E-8 M for binding to p38β at pH 4.

Example 21

Plasma Stability Assay

Human, mouse, rat and monkey plasma (by default K2 EDTA) were obtained from Bioreclamation. 10 µM of each test compound was incubated at 37° C. in the presence of plasma. At 0, 30, 60 and 240 minutes, samples were quenched with organic solvent, vortexed, and centrifuged. The supernatant was transferred to fresh plates for LC/MS/MS analysis using an AB Sciex API 4000™ instrument, coupled to a Shimadzu LC-20AD LC Pump system. Analytical samples were separated using a Waters Atlantis T3 C18 reverse phase HPLC column (20 mm×2.1 mm) at a flow rate of 0.5 mL/min. The mobile phase included of 0.1% formic acid in water (solvent A) and 0.1% formic acid in 100% acetonitrile (solvent B).

The extent of metabolism was calculated as the disappearance of the test compound, compared to the 0-min control reaction incubation. Propantheline was included as a positive control to verify assay performance.

Compounds 1, 6, 8, 10, and 14 were stable in human, monkey, and rat plasma for at least 4 hours.

Example 22

SARS-CoVID-19 Anti-Viral Efficacy

A549-ACE2 cells were cultured in DMEM supplemented with 10% FBS and maintained at 37° C. with 5% CO2. HEK293T-ACE2 cells (ATCC, CRL-3216) were maintained in DMEM (Corning) supplemented with 10% FB (Peak Serum) and Penicillin/Streptomycin (Corning) at 37° C. and 5% $CO_2$. hACE2 ectopically expressed cells were generated by transducing with a lentiviral vector expressing human ACE2. Puromycin resistant cells with hACE2 surface expression were sorted after staining with Alexa Fluor® 647-conjugated goat anti-hACE2 antibodies. Cells were then single-cell-cloned and screened for their ability to support SARS-CoV-2 replication. All cell lines used in this study were regularly screened for *Mycoplasma* contamination using the Universal Detection Kit (ATCC, 30-1012K).

The SARS-CoV-2 isolate BetaCoV/France/IDF0372/2020 (SARS-CoV-2 Paris) was supplied by the National Reference Centre for Respiratory Viruses hosted by Institute Pasteur (Paris, France). The isolate was supplied through the European Virus Archive goes Global (EVAg) platform. Viral stocks were prepared by propagation in Vero E6 cells in DMEM supplemented with 2% FBS. Viral titers were determined by plaque assay in Minimum Essential Media (MEM) supplemented with 2% (v/v) FBS (Invitrogen) and 0.05% agarose. All experiments involving live SARS-CoV-2 were performed in compliance with Institute Pasteur Paris's guidelines for Biosafety Level 3 (BSL-3) containment procedures in approved laboratories.

The SARS-CoV-2, isolate USA-WA1/2020 (NR-52281) (SARS-CoV-2 New York), which shares 99.983% sequence identity with the BetaCoV/France/IDF0372/2020 isolate, was deposited by the Center for Disease Control and Prevention and obtained through BEI Resources, NIAID, NIH. SARS-CoV-2 was propagated in Vero E6 cells in DMEM supplemented with 2% FBS, 4.5 g/L D-glucose, 4 mM L-glutamine, 10 mM Non-Essential Amino Acids, 1 mM Sodium Pyruvate and 10 mM HEPES. All work involving live SARS-CoV-2 was performed in the CDC/USDA-approved BSL-3 facility of the Global Health and Emerging Pathogens Institute at the Icahn School of Medicine at Mount Sinai in accordance with institutional biosafety requirements.

Two hours before infection, the medium was replaced with DMEM (2% FBS) containing the compound of interest at concentrations 50% greater than those indicated, including a DMSO control. Plates were then transferred into the BSL-3 facility and the same volume of SARS-CoV-2 was added in DMEM (2% FBS), bringing the final compound concentration to those indicated. Plates were then incubated for 48 hours at 37° C. All assays were performed in biologically independent triplicates.

Detection of viral genomes was performed by RT-qPCR, directly from the inactivated supernatant. SARS-CoV-2 specific primers targeting the N gene region: 5'-TAATCAGACAAGGAACTGATTA-3' (SEQ ID NO: 1) (Forward) and 5'-CGAAGGTGTGACTTCCATG-3' (SEQ ID NO: 2) (Reverse) were used with the Luna® Universal One-Step RT-qPCR Kit (NEB) in an *Applied Biosystems* QuantStudio™ 7 thermocycler, with the following cycling conditions: 55° C. for 10 minutes, 95° C. for 1 minute, and 40 cycles of 95° C. for 10 s, followed by 60° C. for 1 minute. The number of viral genomes is expressed as PFU equivalents/mL and was calculated by performing a standard curve with RNA derived from a viral stock with a known viral titer.

Viral quantification via plaque assay in Paris. Cells were seeded in 24-well plates at a concentration of $7.5 \times 10^4$ cells/well. The following day, serial dilutions were performed in serum-free MEM media. After 1 hour, absorption at 37° C., 2× overlay media was added to the inoculum to give a final concentration of 2% (v/v) FBS/MEM media and 0.05% (w/v) agarose (all Thermo Fisher Scientific) to achieve a semi-solid overlay. Plaque assays were incubated at 37° C. for 3 days. Samples were fixed using 4% formalin (Sigma Aldrich) and plaques were visualized using crystal Violet solution (Sigma Aldrich).

Cell viability Paris. Cell viability was measured using the CellTiter-Glo® luminescent cell viability assay (Promega) following the manufacturer's instructions, and luminescence measured in a Tecan Infinite® 2000 plate reader. Cytotoxicity was performed in uninfected cells with same compound dilutions and concurrent with viral replication assay. Percent viability was calculated relative to untreated cells (100% viability) and cells lysed with 20% ethanol (0% viability).

Viral quantification via N-protein staining in New York. After infection, supernatants were removed, and cells were fixed with 4% formaldehyde for 24 hours prior to being removed from the BSL-3 facility. The cells were then immunostained for the viral NP protein (1:10,000) with a DAPI counterstain. Infected (488 nM) and total cells (DAPI) were quantified using the Celigo (Nexcelcom) imaging cytometer. Infectivity was measured by the accumulation of viral NP protein in the nucleus of the cells (fluorescence accumulation). Percent infection was quantified as ((Infected cells/Total cells)−Background)×100 and the DMSO control was then set to 100% infection for analysis.

Cell viability New York. Cytotoxicity was also performed using the MTT assay (Roche), according to the manufacturer's instructions. Cytotoxicity was performed in uninfected cells with same compound dilutions and concurrent with viral replication assay. Percent viability was calculated relative to untreated cells (100% viability).

Data analysis and IC50 calculation. A Hill function was fit to each dose response curve using the lsqcurvefit function in MATLAB (R2018a). IC50 (virus) values were defined as the concentration at which the percent measure (virus or cell viability quantification) crossed the 50% mark. If the fit curve did not begin above 50% and cross to below 50% throughout the dose response, an IC50 value was marked as greater than the maximum tested concentration.

Compounds (1), (2), (3), (4), (6), (8), (1), (11), (13), and (17) exhibited an IC50 for anti-SARS-CoVID-19 activity less than 1E-5 M. The results are presented in Table 1.

TABLE 1

| | Anti-viral activity. | | |
|---|---|---|---|
| Compound | Anti-Viral Paris IC50 (µM) | Anti-Viral NY IC50 (µM) | Plaque IC50 (µM) |
| 1 | 0.6 | 0.7 | 1.8 |
| 2 | 7.8 | 1.2 | [1]— |
| 3 | 9.4 | 1.2 | — |
| 4 | 2.1 | 0.7 | 1.4 |
| 5 | — | — | — |
| 6 | 2.9 | 6.4 | — |
| 7 | — | — | — |
| 8 | — | — | — |
| 9 | 3.1 | — | — |
| 10 | 1.3 | 0.2 | 2.8 |
| 11 | 1.6 | 0.2 | 2.1 |
| 12 | — | — | — |
| 13 | 3.4 | | |
| 14 | — | — | — |
| 15 | — | — | — |
| 16 | — | — | — |
| 17 | 3.6 | 0.7 | 2.7 |

[1]Not measured.

Finally, it should be noted that there are alternative ways of implementing the embodiments disclosed herein. Accord-

What is claimed is:

1. A compound having the structure of Formula (1):

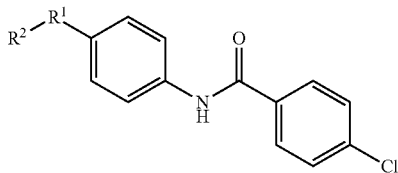

or a pharmaceutically acceptable salt thereof, wherein,
$R^1$ is selected from $C_{1-4}$ alkanediyl and $C_{1-4}$ heteroalkanediyl; and
$R^2$ is a moiety having the structure of Formula (2d):

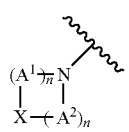

wherein,
each of $A^1$ and $A^2$ is independently selected from —CH2— and —C(=O)—;
each n is independently selected from 1, 2, and 3; and
X is —$NR^3$— and $R^3$ is —C(=O)—CH3.

2. The compound of claim 1, wherein $R^1$ is $C_{1-4}$ alkanediyl.

3. The compound of claim 1, wherein $R^1$ is selected from methanediyl and ethanediyl.

4. The compound of claim 1, wherein one n is 1 and the other n is selected from 2 and 3.

5. The compound of claim 1, wherein each n is 2 or each n is 3.

6. A pharmaceutical composition comprising the compound of claim 1 or a pharmaceutically acceptable salt thereof.

7. The pharmaceutical composition of claim 6, wherein the pharmaceutical composition comprises a therapeutically effective amount of the compound or a pharmaceutically acceptable salt thereof for treating a disease in a patient, wherein the etiology of the disease is associated with up-regulation of the p38α MAPK protein, with the down-regulation of the p38α MAPK protein, or with both the up-regulation and the down-regulation of the p38α MAPK protein.

8. The pharmaceutical composition of claim 6, wherein the pharmaceutical composition comprises a therapeutically effective amount of the compound or a pharmaceutically acceptable salt thereof for treating a disease in a patient, wherein the disease is selected from cancer, an inflammatory disease, and autoimmune disease, and a viral disease.

9. The pharmaceutical composition of claim 6, wherein the pharmaceutical composition comprises a therapeutically effective amount of the compound or a pharmaceutically acceptable salt thereof for treating a disease in a patient, wherein the disease is selected from acute lung injury, acute respiratory distress syndrome (ARDS), chronic obstructive pulmonary disease (COPD), amyotrophic lateral sclerosis, and cystic fibrosis.

10. A method of treating a disease in a patient comprising administering to a patient in need thereof a therapeutically effective of amount of the compound of claim 1 or a pharmaceutically acceptable salt thereof, wherein the disease is selected from cancer, an inflammatory disease, an autoimmune disease, and a viral disease.

11. A method of treating a disease in a patient comprising administering to a patient in need thereof a therapeutically effective of amount of the pharmaceutical composition of claim 6, wherein the disease is selected from cancer, an inflammatory disease, an autoimmune disease, and a viral disease.

12. A compound having the structure of Formula (1):

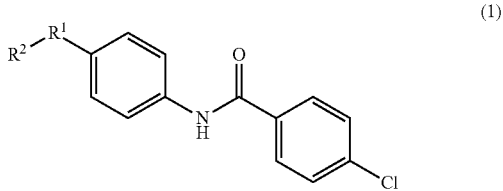

(1)

or a pharmaceutically acceptable salt thereof, wherein,
$R^1$ is $C_{1-4}$ alkanediyl; and
$R^2$ is a moiety having the structure of Formula(2d

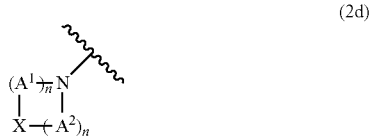

(2d)

wherein,
each n is independently selected from, 1, 2, and 3;
each of $A^1$ and $A^2$ is independently selected from —CH$_2$— and —C(=O)—,
and at least one of $A^1$ and $A^2$ is —C(=O)—; and
X is —NR$^3$—, wherein R$^3$ is selected from hydrogen, $C_{1-6}$ alkyl, and substituted $C_{1-6}$ alkyl.

13. The compound of claim 12, wherein each substituent is selected from —OH and =o.

14. The compound of claim 12, wherein $R^1$ is selected from methanediyl and ethanediyl.

15. A compound having the structure of Formula (1):

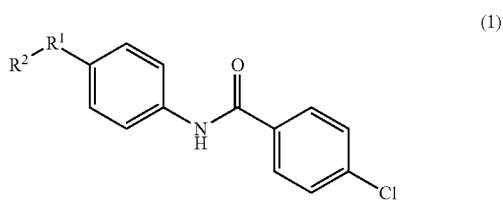

(1)

or a pharmaceutically acceptable salt thereof, wherein,
$R^1$ is selected from $C_{1-4}$ alkanediyl, $C_{1-4}$ heteroalkanediyl, substituted $C_{1-4}$ alkanediyl, and substituted $C_{1-4}$ heteroalkanediyl; and
$R^2$ is a moiety having the structure of Formula (2d):

(2d)

wherein,
one n is 1 and the other n is selected from 2 and 3;
each of $A^1$ and $A^2$ is independently selected from —CH$_2$— and —C(=O)—, and at least one of $A^1$ and $A^2$ is —C(=O)—; and X is —NR$^3$—, wherein R$^3$ is selected from hydrogen, $C_{1-6}$ alkyl, and substituted $C_{1-6}$ alkyl.

16. The compound of claim 12, wherein each n is 2 or each n is 3.

17. The compound of claim 12, wherein the compound is selected from:
4-chloro-N-(4-((3-oxopiperazin-1-yl)methyl)phenyl)benzamide (15); and
4-chloro-N-(4-((4-methyl-3-oxopiperazin-1-yl)methyl)phenyl)benzamide (16);
or a pharmaceutically acceptable salt of any of the foregoing.

18. A pharmaceutical composition comprising the compound of claim 12 or a pharmaceutically acceptable salt thereof.

19. The pharmaceutical composition of claim 18, wherein the pharmaceutical composition comprises a therapeutically effective amount of the compound or a pharmaceutically acceptable salt thereof for treating a disease in a patient, wherein the etiology of the disease is associated with up-regulation of the p38α MAPK protein, with the down-regulation of the p38α MAPK protein, or with both the up-regulation and the down-regulation of the p38α MAPK protein.

20. The pharmaceutical composition of claim 18, wherein the pharmaceutical composition comprises a therapeutically effective amount of the compound or a pharmaceutically acceptable salt thereof for treating a disease in a patient, wherein the disease is selected from cancer, an inflammatory disease, and autoimmune disease, and a viral disease.

21. The pharmaceutical composition of claim 18, wherein the pharmaceutical composition comprises a therapeutically effective amount of the compound or a pharmaceutically acceptable salt thereof for treating a disease in a patient, wherein the disease is selected from acute lung injury, acute respiratory distress syndrome (ARDS), chronic obstructive pulmonary disease (COPD), amyotrophic lateral sclerosis, and cystic fibrosis.

22. A method of treating a disease in a patient comprising administering to a patient in need thereof a therapeutically effective of amount of the compound of claim 12, or a pharmaceutically acceptable salt thereof, wherein the disease is selected from cancer, an inflammatory disease, an autoimmune disease, and a viral disease.

23. A method of treating a disease in a patient comprising administering to a patient in need thereof a therapeutically effective of amount of the pharmaceutical composition of claim 18, wherein the disease is selected from cancer, an inflammatory disease, an autoimmune disease, and a viral disease.

24. A pharmaceutical composition comprising the compound of claim 15 or a pharmaceutically acceptable salt thereof.

25. The pharmaceutical composition of claim 24, wherein the pharmaceutical composition comprises a therapeutically effective amount of the compound or a pharmaceutically acceptable salt thereof for treating a disease in a patient, wherein the etiology of the disease is associated with up-regulation of the p38α MAPK protein, with the down-regulation of the p38α MAPK protein, or with both the up-regulation and the down-regulation of the p38α MAPK protein.

26. The pharmaceutical composition of claim 24, wherein the pharmaceutical composition comprises a therapeutically effective amount of the compound or a pharmaceutically acceptable salt thereof for treating a disease in a patient, wherein the disease is selected from cancer, an inflammatory disease, and autoimmune disease, and a viral disease.

27. The pharmaceutical composition of claim 24, wherein the pharmaceutical composition comprises a therapeutically effective amount of the compound or a pharmaceutically acceptable salt thereof for treating a disease in a patient, wherein the disease is selected from acute lung injury, acute respiratory distress syndrome (ARDS), chronic obstructive pulmonary disease (COPD), amyotrophic lateral sclerosis, and cystic fibrosis.

28. A method of treating a disease in a patient comprising administering to a patient in need thereof a therapeutically effective of amount of the compound of claim 15, or a pharmaceutically acceptable salt thereof, wherein the disease is selected from cancer, an inflammatory disease, an autoimmune disease, and a viral disease.

29. A method of treating a disease in a patient comprising administering to a patient in need thereof a therapeutically effective of amount of the pharmaceutical composition of claim 15, wherein the disease is selected from cancer, an inflammatory disease, an autoimmune disease, and a viral disease.

* * * * *

UNITED STATES PATENT AND TRADEMARK OFFICE
CERTIFICATE OF CORRECTION

| | |
|---|---|
| PATENT NO. | : 11,440,918 B2 |
| APPLICATION NO. | : 17/667898 |
| DATED | : September 13, 2022 |
| INVENTOR(S) | : Adam Galan, Wendy Luo and Ritu Lal |

Page 1 of 1

It is certified that error appears in the above-identified patent and that said Letters Patent is hereby corrected as shown below:

In the Claims

Column 77, Claim 1, Line 60 that reads "–CH2–" should read - –$CH_2$– -

Column 77, Claim 1, Line 62 that reads "–C(=O)–CH3." should read - –C(=O)–$CH_3$. -

Column 79, Claim 13, Line 35 that reads "=o." should read - =O. -

Signed and Sealed this
Twenty-fifth Day of October, 2022

Katherine Kelly Vidal
*Director of the United States Patent and Trademark Office*